(12) United States Patent
Kramer

(10) Patent No.: US 7,846,686 B2
(45) Date of Patent: Dec. 7, 2010

(54) **MICROGININ PRODUCING PROTEINS AND NUCLEIC ACIDS ENCODING A MICROGININ GENE CLUSTER AS WELL AS METHODS FOR CREATING NOVEL MICROGININ

MICROGININ PRODUCING PROTEINS AND NUCLEIC ACIDS ENCODING A MICROGININ GENE CLUSTER AS WELL AS METHODS FOR CREATING NOVEL MICROGININS

CROSS REFERENCE TO RELATED APPLICATION

This application is a 35 U.S.C. 371 National Phase Entry Application from PCT/EP2006/011563, filed Dec. 1, 2006, which claims the benefit of European Patent Application No. 05026396.1 filed on Dec. 2, 2005, the disclosure of which is incorporated herein in its entirety by reference.

TECHNICAL FIELD

The present invention relates to the fields of chemistry, biology, biochemistry, molecular biology. The invention provides for novel nucleic acid molecules enabling the synthesis of microginin and microginin analogues. Microginin finds an application in therapeutics. The invention thus extends into the field of mammalian therapeutics and drug development.

INTRODUCTION

Cyanobacteria and Microginin

Cyanbacteria are gram-negative bacteria. Due to their ability to perform photosynthesis they were long thought to belong to the plant kingdom and were formerly classified as blue-green algae. Cyanbacteria have adapted to almost all ecological niches. Most of strains known up to date are found in fresh water lakes and oceans. In the last few years cyanobacteria have been recognised as a source for biologically active natural compounds.

Cyanobacteria are a group of microscopic organisms somewhere "in between" algae and bacteria and they are found in freshwater and marine areas throughout the world. Scientifically, they are considered to be bacteria, but because they can perform photosynthesis, they also used to be classified as "blue-green algae".

Cyanobacterial peptides (cyanopeptides) are among the most ubiquitously found potentially hazardous natural products in surface waters used by humans. Though these substances are natural in origin, eutrophication (i.e. excessive loading with fertilising nutrients) has caused massive cyanobacterial proliferation throughout Europe. Thus, cyanopeptides now occur with unnatural frequency and concentration.

A large group among the diverse cyanopeptides are the oligopeptides (peptides with a molecular weight of <2 KD). But while specific cyanopeptides—e.g. microcystins and nodularins—are well studied and recognised as being causative for many animal poisonings and human illness, a substantial and increasing body of evidence points toward a decisive role of other potentially toxic cyanopeptides in the causation of both acute and chronic human illnesses.

Freshwater and marine cyanobacteria are known to produce a variety of bioactive compounds, among them potent hepatotoxins and neurotoxins. Many of the toxic species of cyanobacteria tend to massive proliferation in eutrophicated water bodies and thus have been the cause for considerable hazards for animal and human health. One of the most widespread bloom-forming cyanobacteria is the genus *Microcystis*, a well-known producer of the hepatotoxic peptide microcystin. Microcystins are a group of closely related cyclic heptapeptides sharing the common structure. So far, more than 80 derivatives of microcystins have been identified, varying largely by the degree of methylation, peptide sequence, and toxicity.

The traditional botanical code describes the genus *Microcystis* as a coccal, unicellular cyanobacterium that grows as mucilaginous colonies of irregularly arranged cells (under natural conditions, while strain cultures usually grow as single cells). According to this tradition, morphological criteria such as size of the individual cells, colony morphology, and mucilage characteristics are used for species delimitation within *Microcystis* (i.e., morphospecies). Microcystin-producing strains as well as strains that do not synthesize microcystin have been reported for all species within the genus *Microcystis*. However, whereas most field samples and strains of *Microcystis aeruginosa* and *Microcystis viridis* studied to date were found to contain microcystins, strains of *M. wesenbergii, M. novaceckii*, and *M. ichthyoblabe* have only sporadically been reported to contain microcystins.

Beside microcystins, various other linear and cyclic oligopeptides such as anabaenopeptins, aeruginosins, microginins and cyanopeptolins are found within the genus *Microcystis* (Namikoshi, M., and K. L. Rinehart. 1996. Bioactive compounds produced by cyanobacteria. J. Ind. Microbiol. 17:373-384.).

Similar to microcystins, these peptides possess unusual amino acids like 3-amino-6-hydroxy-2-piperidone (Ahp) in cyanopeptolins, 2-carboxy-6-hydroxyoctahydroindol (Choi) in aeruginosin-type molecules or 3-amino-2 hydroxy-decanoic acid (Ahda) in microginins and numerous structural variants also exist within these groups. These peptides show diverse bioactivities, frequently protease inhibition (Namikoshi, M., and K. L. Rinehart. 1996. Bioactive compounds produced by cyanobacteria. J. Ind. Microbiol. 17:373-384).

The occurrence of both microcystins and other oligopeptides such as anabaenopeptins, microginins and cyanopeptolins in natural *Microcystis* populations was recently demonstrated. It is well known that the species and genotype composition in natural *Microcystis* populations is heterogeneous, and both microcystin- and non-microcystin-containing strains have been isolated from the same sample. Just as strains producing microginin and strains not producing microginin have been found. These results suggest a considerable diversity of genotypes with different oligopeptide patterns in natural *Microcystis* populations.

By typing single *Microcystis* colonies, it was possible in 1999 to show for the first time that the actual peptide diversity in a natural population of this genus is extremely high. Many of the substances detected belong to well-known groups of cyanobacterial peptides like microcystins, anabaenopeptins, microginins, cyanopeptolins, and aeruginosins, of which many have been discovered in *Microcystis* spp. In addition, numerous unknown components have been detected in such colonies. However, the origin of these unknown components has yet to be investigated, since besides the observed epiphytic cyanobacteria and algae, heterotrophic bacteria are also known to be present in *Microcystis* colonies. Chemical screening of cyanobacterial samples (both from field samples and from culture strains) has demonstrated a wide variety of substances: e.g. an almost monospecific bloom of *Planktothrix agardhii* contained as many as 255 different substances, most of which were oligopeptides.

Thus, it may be concluded, that the situation with respect to the assignment of the capability of microginin production to certain species and strains, i.e. also a true understanding of the genotypes and species involved as well as their evolution has to date, not been possible. In fact PEPCY a research project supported by the European Commission concluded that present information shows that one species or "morphotype" (i.e. individuals with the same morphological characteristics) may comprise a range of genotypes that encode for different "chemotypes" (i.e. morphologically indistinguishable individuals containing different cyanopeptides).

ACE Inhibitors and Microginin

ACE catalyses the conversion of angiotensin I into angiotensin II within the mammalian renin-angiotensin system, leading to arterial stenosis, which in turn causes an increase of blood pressure. ACE inhibitors counteract this process and therefore play a role in human medicine as blood pressure lowering agents. Microginin is an important drug candidate for ACE inhibition. So far only 30 structural variants of microginin are known, making clinical development difficult.

Microginins are characterized by a decanoic acid derivate, 3-amino-2-hydroxy-decanoic acid (Ahda) at the N-terminus and a predominance of two tyrosine units at the C-terminus. They vary in length from 4 to 6 amino acids with the variability occurring at the C-terminal end (Microginins, zinc metalloprotease inhibitors from the cyanobacterium *Microcystis aeruginosa*, 2000, Tetrahedron 56:8643-8656). In the past it has only been possible by means of synthesis of 3-amino-2-hydroxy-decanoic acid to chemically generate microginin variants (J Org. Chem. 1999 Apr. 16; 64(8):2852-2859. Acylnitrene Route to Vicinal Amino Alcohols. Application to the Synthesis of (−)-Bestatin and Analogues. Bergmeier S C, Stanchina D M.) Alternatively cyanobacterial strains were screened for microginin activity, which was tedious and time consuming. It has so far not been possible to screen for strains efficiently due to the lack of species understanding and a methodology of efficiently distinguishing microginin producers from non-producers (see above). Further it was not possible to easily and efficiently alter and thus develop microginins in order to provide for a variety of lead compounds from which better ACE-inhibitors may be developed.

BRIEF DESCRIPTION OF THE INVENTION

From *Microcystis aeruginosa* a cluster of genes, spanning about 30 kbps has been isolated encoding a hybrid synthetase composed of non-ribosomal peptide synthetases (NRPS), polyketide synthases (PKS) and tailoring enzyme which as the inventors show is responsible for the biosynthesis of microginin. The strain from which this nucleic acid was first isolated by G. C. Kürzinger from Lake Pehlitz 1977].

The inventors provide for a biological system enabling not only the production of micoginins, the heterologous expression of microginin, but also a system for modifying microginin and thus developing so far unknown variants of microginin. The invention further provides for nucleic acids and methods for identifying strains which have the ability to produce microginin.

In particular the invention relates to one or more nucleic acids encoding a microginin synthetase enzyme complex with the following activities: an adenylation domain (A*) wherein, the adenylation domain comprises a peptide sequence according to SEQ ID NO. 1, an acyl carrier protein (ACP), an elongation module (EM) of polyketide synthases (PKS) comprising the following activities: (i) ketoacylsynthase (KS), (ii) acyl transferase (AT) (iii) acyl carrier protein (ACP2), an aminotransferase (AMT), three to five elongation modules (EM) of non-ribosomal peptide synthetases (NRPS) comprising the following activities: (i) condensation domain (C), (ii) adenylation domain (A), (iii) thiolation domain (T) and a thioesterase (TE).

DETAILED DESCRIPTION OF THE INVENTION

Figure 1:
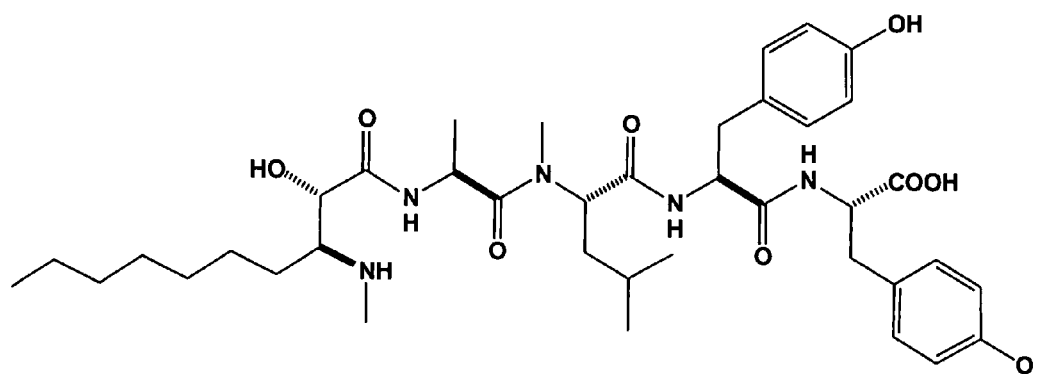

As outlined above the invention in particular relates to one or more nucleic acids encoding a microginin synthetase enzyme complex with the following activities: an adenylation domain (A*) wherein, the adenylation domain comprises a peptide sequence according to SEQ ID NO. 1, an acyl carrier protein (ACP), an elongation module (EM) of polyketide synthases (PKS) comprising the following activities: (i) ketoacylsynthase (KS), (ii) acyl transferase (AT) (iii) acyl carrier protein (ACP 2), an aminotransferase (AMT), three to five elongation modules (EM) of non-ribosomal peptide synthetases (NRPS) comprising the following activities: (i) condensation domain (C), (ii) adenylation domain (A), (iii) thiolation domain (T) and a thioesterase (TE).

The inventors have found that microginin is the product of non-ribosomal synthesis. It is important to understand that microginin as previously identified in nature may also in part have been the product of ribosomal synthesis and further processed via various enzymatic reactions.

It is important to note that the nucleic acid claimed herein, i.e. a microginin synthetase enzyme complex may also be present in organisms other organisms than *Microcystis* sp., such as Nostoc, Anabaena, Plankthotrix or Oscillatoria. The term microginin shall thus not limit the invention to such nucleic acids producing synthetase enzyme complexes resulting in peptides officially termed "microginin".

Herein, an adenylation domain (A*) is understood to activate octanoic acid as an acyl adenylate and an acyl carrier protein (ACP) is understood to bind the octanoic acid adenylate as a thioester.

An elongation module (EM) of polyketide synthases (PKS) is also known e.g. from the Jamaicamide synthetase gene cluster isolated from *Lyngbya majuscula* (Chem. Biol. Vol. 11, 2004 pp 817-833. Structure and Biosynthesis of the Jamaicamides, new mixed polyketide-peptide neurotoxin from the marine cyanobacterium *Lyngbya majuscula*) herein comprises at least the following activities: (i) ketoacylsynthase (KS), (ii) acyl transferase (AT) and (iii) acyl carrier protein (ACP2). The AT is responsible for the recognition of malonyl-CoA, the KS is responsible for the Claisen-type-condensation of the activated octanoic acid adenylate with malonyl-CoA and the ACP2 is responsible for binding of the resulting decanoic acid. An aminotransferase (AMT) performs the β-amination of the decanoic acid.

The nucleic acid according to the invention may have three to five elongation modules (EM) of non-ribosomal peptide synthetases (NRPS) comprising at least the following activities: (i) condensation domain (C), (ii) adenylation domain (A), (iii) thiolation domain (T). The A is responsible for the activation of carboxyl groups of amino acids, the T is responsible for the binding and the transport of the activated intermediate, the C is responsible for the condensation of the activated amino acids with the growing peptide chain.

Finally the nucleic acid according to the invention shall contain a thioesterase (TE) activity which performs the clevage of the final product from the synthetase complex.

One may envision that the nucleic acid according to the invention is present in a vector or a bacterial chromosome, in which case one may envision that the portions designated above while being in one cell need not all, be in, or on, one molecule. It is essential to the invention however, that a cell meant to produce microginin synthetase enzyme complex contains the activities designated above in order to produce an enzyme complex according to the invention which in turn may produce a microginin. Thus, the invention also encompasses derivatives of the nucleic acid molecule as outlined above having the function of a microginin synthetase enzyme complex.

The molecule is characterized by a special adenylation domain (A*) which is unusual in that it is not similar to known adenylation domains found in other molecules encoding non-ribosomal enzyme complexes such as the microcystin synthetase gene cluster (Chem. Biol. Vol. 7 2000, pp 753-764: Structural organisation of microcystin synthesis in *Microcys-*

*tis aeruginosa* PCC 7806: In integrated peptide-polyketide-synthetase system) Molecules encompassed herein are those which carry this adenylation domain (A*) as depicted in SEQ ID NO. 1 and at least an ACP whereby this ACP may stem from another known non-ribosomal enzyme complex, at least one EM of PKS whereby this EM may stem from another known non-ribosomal enzyme complex comprising at least the following activities: (i) KS, (ii) AT (iii) ACP, an AMT whereby this AMT may stem from another known non-ribosomal enzyme complex three to five EMs comprising at least the following activities: (i) C, (ii) A, (iii) T whereby these EMs may stem from another known non-ribosomal enzyme complex and a TE whereby this TE may stem from another known non-ribosomal enzyme complex. Chimeras whereby parts of the above are on one or more vectors and or integrated in chromosomes are equally encompassed by the invention as long as all the components are in one cell.

The invention also pertains to isolated nucleic acid molecules encoding a microginin synthetase enzyme complex comprising an adenylation domain which is 85% identical to SEQ ID NO. 1, more preferred 90% identical to SEQ ID NO. 1 most preferred 95% identical to SEQ ID NO. 1. Sequence identity herein is in percent of total sequence of the adenylation domains when aligned with conventional nucleotide alignment software, such as the best fit and or pileup programs of the GCG package The invention also pertains to a microginin synthetase enzyme protein complex with the following activities: an adenylation domain (A*) wherein, the adenylation domain comprises a peptide sequence according to SEQ ID NO. 1, an acyl carrier protein (ACP), an elongation module (EM) of polyketide synthases (PKS) comprising the following activities: (i) ketoacylsynthase (KS), (ii) acyl transferase (AT) (iii) acyl carrier protein (ACP 2), an aminotransferase (AMT), three to five elongation modules (EM) of non-ribosomal peptide synthetases (NRPS) comprising the following activities: (i) condensation domain (C), (ii) adenylation domain (A), (iii) thiolation domain (T) and a thioesterase (TE).

The invention in particular also relates to a nucleic acid molecule encoding an adenylation domain (A*) wherein, the adenylation domain comprises a peptide sequence according to SEQ ID NO. 1.

The invention in particular also relates to a peptide molecule, an adenylation domain (A*) wherein, the molecule comprises a peptide sequence according to SEQ ID NO. 1.

The invention in particular also relates to a nucleic acid molecule encoding an adenylation domain (A*) wherein, the molecule comprises a nucleic acid sequence according to SEQ ID NO. 25.

In a preferred embodiment of the invention the nucleic acid additionally and optionally comprises sequences encoding the following activities or domains: a monooxygenase (MO), an integrated N-methyltransferase domain (MT) within one or more elongation modules (EM) of NRPS, a non-integrated N-methyltrasferase (MT), a modifying activity (MA) wherein, said MA is selected from the group comprising the following activities: halogenase, sulfatase, glycosylase, racemase, O-methyltransferase and C-methyltransferase, two or more peptide repeat spacer sequences (SP) consisting of one or more repeats of being either glycine rich or proline and leucine rich, located adjacently upstream and downstream of the MO and/or another MA.

Herein MO is an enzyme catalyzing the hydroxylation of the decanoic acid, an integrated N-methyltransferase domain (MT) within one or more elongation modules (EM) of NRPS catalyses the methylation of the amide bond by the respective module and a non-integrated N-methyltrasferase (MT) catalyzes the methylation of an amino group of the microginin. The term modifying enzyme stands for numerous enzymes such enzymes may add groups or create bonds, in a preferred embodiment MA is selected from the group comprising the following activities: halogenase, sulfatase, glycosylase, racemase, O-methyltransferase and C-methyltransferase.

Nucleic acids encoding two or more peptide repeat spacer sequences (SP) consisting of one or more repeats being either glycine rich or proline and leucine rich have astonishingly been found by the inventors to aid in integration of novel MAs into existing microginin synthetase enzyme complexes. By means of placing such SPs adjacently to MAs the inventors are able to create microginin synthetase enzyme complexes (MSEC) comprising activities previously not found in MSECs. This in turn allows for the creation of novel microginins with potentially novel therapeutic properties. Thus the invention relates to nucleic acids encoding two or more peptide repeat spacer sequences (SP) consisting of one or more repeats being either glycine rich or proline and leucine rich may be positioned adjacently to a MA such as but not limited to a halogenase, a sulfatase, a glycosylase, a racemase, an O-methyltransferase or a C-methyltransferase. These SPs aid in ensuring that the "foreign" activity "works" in the enzyme complex. The inventors have found, that this is due to the lack of secondary structures in the SP peptide chains.

The nucleic acid according to the invention in a preferred embodiment optionally comprises the following sequences, nucleic acid sequences encoding protein sequences as follows:

An adenylation domain (A*) according to SEQ ID NO. 1, an acyl carrier protein (ACP) according to SEQ ID NO. 2, an elongation module of polyketide synthases responsible for the activation and the condensation of malonyl-Co A: (i) ketoacylsynthase domain (KS) according to SEQ ID NO. 3, (ii) acyl transferase domain (AT) according to SEQ ID NO. 4, an acyl carrier protein domain (ACP 2) according to SEQ ID NO. 5, an aminotransferase (AMT) according to SEQ ID NO. 6, an elongation modules of non-ribosomal peptide synthetases responsible for the activation and condensation of alanin: (i) condensation domain (C) according to SEQ ID NO. 7, (ii) adenylation domain (A) according to SEQ ID NO. 8, (iii) thiolation domains (T) according to SEQ ID NO. 9, an elongation modules of non-ribosomal peptide synthetases responsible for the activation and condensation of leucin: (i) condensation domain (C2) according to SEQ ID NO. 10, (ii) adenylation domain (A 2) according to SEQ ID NO. 11, (iii) thiolation domain (T 2) according to SEQ ID NO. 12, an elongation modules of non-ribosomal peptide synthetases responsible for the activation and condensation of tyrosine 1: (i) condensation domain (C 3) according to SEQ ID NO. 13, (ii) adenylation domain (A 3) according to SEQ ID NO. 14 (iii) thiolation domain (T 3) according to SEQ ID NO. 15, an elongation modules of non-ribosomal peptide synthetases responsible for the activation and condensation of tyrosine 2: (i) condensation domain (C4) according to SEQ ID NO. 16, (ii) adenylation domain (A 4) according to SEQ ID NO. 17, (iii) thiolation domain (T 4) according to SEQ ID NO. 18, a thioesterase (TE) according to SEQ ID NO. 19, a monooxygenase (MO) according to SEQ ID NO. 20, two or more peptide repeat spacer sequences (SP1/SP2) according to SEQ ID NO. 21 and 22, an integrated N-methyltransferase domain (MT) within the elongation module (EM) of the NRPS responsible for the activation and condensation of leucin according to SEQ ID 23 and a non-integrated N-methyltrasferase (MT 2) according to SEQ ID NO. 24.

As outlined above, the minimal requirement according to the invention is a nucleic acid encoding a microginin synthetase enzyme complex with the following activities: an adenylation domain (A*) wherein, the adenylation domain comprises a peptide sequence according to SEQ ID NO. 1, an ACP according to SEQ ID NO. 2, an elongation module (EM) of polyketide synthases (PKS) comprising the following activities: (i) ketoacylsynthase (KS) according to SEQ ID NO. 3, (ii) acyl transferase (AT) according to SEQ ID NO 4, (iii) acyl carrier protein (ACP 2) according to SEQ ID NO. 5, an aminotransferase (AMT) according to SEQ ID NO. 6, three to five elongation modules (EM) of non-ribosomal peptide synthetases (NRPS) comprising the following activities: (i) condensation domain (C) according to SEQ ID NO. 7, (ii) adenylation domain (A) according to SEQ ID NO. 8, (iii) thiolation domain (T) according to SEQ ID NO. 9 and a thioesterase (TE) according to SEQ ID NO. 10. A molecule comprising the above sequences is preferred herein.

The invention explicitly also relates to analogs hereto, additionally comprising, e.g. other activities and/or spacer regions both transcribed and non-transcribed.

It is apparent to those skilled in the art, that amino acids may be exchanged maintaining the enzymatic activity required. Thus, the invention also relates to molecules with sequences which are not identical to those outlined above however, altered only in so far as the enzymatic activity desired is retained.

The nucleic acid according to the invention may contain nucleic acids selected from the group comprising: an adenylation domain (A*) according to SEQ ID NO. 25, an acyl carrier protein (ACP) according to SEQ ID NO. 26, an elongation module of polyketide synthases encoding for the activation and the condensation of malonyl-Co A: (i) ketoacyl-synthase domain (KS) according to SEQ ID NO. 27, (ii) acyl transferase domain (AT) according to SEQ ID NO. 28, (iii) acyl carrier protein domain (ACP 2) according to SEQ ID NO. 29, an aminotransferase (AMT) according to SEQ ID NO. 30, an elongation modules of non-ribosomal peptide synthetases encoding for the activation and condensation of alanin: (i) condensation domain (c) according to SEQ ID NO. 31, (ii) adenylation domain (A) according to SEQ ID NO. 32, (iii) thiolation domain (T) according to SEQ ID NO. 33, an elongation modules of non-ribosomal peptide synthetases encoding for the activation and condensation of leucin: (i) condensation domain (C 2) according to SEQ ID NO. 34, (ii) adenylation domain (A 2) according to SEQ ID NO. 35, (iii) thiolation domain (T 2) according to SEQ ID NO. 36, elongation modules of non-ribosomal peptide synthetases encoding for the activation and condensation of tyrosine 1: (i) condensation domains (C3) according to SEQ ID NO. 37, (ii) adenylation domains (A 3) according to SEQ ID NO. 38, (iii) thiolation domains (T 3) according to SEQ ID NO. 39, elongation modules of non-ribosomal peptide synthetases encoding for the activation and condensation of tyrosine 2: (i) condensation domains (C4) according to SEQ ID NO. 40, (ii) adenylation domains (A 4) according to SEQ ID NO. 41, (iii) thiolation domains (T 4) according to SEQ ID NO. 42, a thioesterase (TE) according to SEQ ID NO. 43, a monooxygenase (MO) according to SEQ ID NO. 44, two or more peptide repeat spacer sequences (SP1/2) according to SEQ ID NO. 45 and 46, an integrated N-methyltransferase domain (MT) within the elongation module (EM) of the NRPS encoding for the activation and condensation of leucin according to SEQ ID 47 and a non-integrated N-methyltrasferase (MT 2) according to SEQ ID NO. 48.

As outlined above, the minimal requirement according to the invention is a nucleic acid encoding a microginin synthetase enzyme complex with the following activities: an adenylation domain (A*) wherein, the adenylation domain is a nucleic acid sequence according to SEQ ID NO. 25, an ACP with a nucleic acid sequence according to SEQ ID NO. 26, an elongation module (EM) of polyketide synthases (PKS) comprising the following activities: (i) ketoacylsynthase (KS) with a nucleic acid sequence according to SEQ ID NO. 27, (ii) acyl transferase (AT) with a nucleic acid sequence according to SEQ ID NO 28, (iii) acyl carrier protein (ACP 2) with a nucleic acid sequence according to SEQ ID NO. 29, an aminotransferase (AMT) with a nucleic acid sequence according to SEQ ID NO. 30, three to five elongation modules (EM) of non-ribosomal peptide synthetases (NRPS) comprising the following activities: (i) condensation domain (C) with a nucleic acid sequence according to SEQ ID NO. 31, (ii) adenylation domain (A) with a nucleic acid sequence according to SEQ ID NO. 32, (iii) thiolation domain (T) with a nucleic acid sequence according to SEQ ID NO. 33 and a thioesterase (TE) with a nucleic acid sequence according to SEQ ID NO. 43. A molecule comprising the above sequences is preferred herein.

The invention also relates to nucleic acid molecules with sequences which are not identical to those outlined above however, altered only in so far as the enzymatic activity desired is retained. I particular one skilled in the art will know that positions in nucleic acid triplets may "wobble" and these positions may thus be altered with no influence on the peptide sequence. Further multiple amino acids are encoded by more than one DNA triplet. One skilled in the art will know that one may alter such triplets maintaining the amino acid sequence. Thus said sequences are equally encompassed by the invention.

The invention also pertains to isolated nucleic acid molecules encoding a microginin synthetase enzyme complex comprising an adenylation domain which is 85% identical to SEQ ID NO. 25, more preferred 90% identical to SEQ ID NO. 1 most preferred 95% identical to SEQ ID NO. 1. Sequence identity herein is in percent of total sequence of the adenylation domains when aligned with a conventional amino acid alignment software such as the best fit and or pileup programs of the GCG package.

In a preferred embodiment the one or more nucleic acids according to the invention are organized in sequence parts encoding the microginin synthetase enzyme complex in an upstream to downstream manner as depicted in FIG. 1. In a particularly preferred embodiment the activities and domains are arranged as shown and on one molecule.

The nucleic acid molecule may be part of a vector. Such vectors are in particular, bacterial artificial chromosomes (BAC), Cosmids or Fosmids, and Lambda vectors. Preferred plasmid vectors which are able to replicate autonomously in cyanobacteria are derived from the pVZ vectors. Preferred fosmid vectors which are able to replicate autonomously in cyanobacteria are derived from the pCC1FOS™ and pCC2FOS™ vectors (Epicentre Biotechnologies). The integration of the nucleic acid according to the invention into the vector is a procedure known to those skilled in the art (Molecular Cloning: A Laboratory manual, 1989, Cold Spring Harbour Labaratory Press) or in the manuals of manufactures of kits for creation of genomic libraries (e.g. Epicenter Biotechnologies).

In a preferred embodiment the invention concerns a microorganism transformed with a nucleic acid according to the invention. The nucleic acid according to the invention may integrated into the chromosome of the host organism or may present on a separate vector (see also examples). It is preferred that the phototrophic cyanobacterial host organism is selected for the group comprising: Synechocystis sp., Synechococcus sp., Anabaena sp., Nostoc sp., Spirulina sp., Microcystis sp . . . . Cells are cultured as follows:

Media: Bg 11 (for cultivation of cyanobacteria)

Aeration: air containing 0.3-3.0% carbon dioxide

Light intensity: 40-100 $\mu E/m^2*s$ (diameter of illuminated culture vessels of photobioreactor d=4-12 cm)

Cell density at harvest: $OD_{750}$ 1-2

And if the host is Microcystis aeruginosa:

Light quality: Additional red light illumination with 25 $\mu E/m^2*s$ for 24-48 hours before harvesting.

It is preferred that the heterotrophic host organism is selected for the group comprising: *E. coli* and *Bacillus* sp. due to a more suitable GC content and codon usage than other heterotrophic bacteria.

In case of using *E. coli* for the heterologues expression of the microginin synthetase a phosphopanthetein transferase (Ppt) has to be co-expressed in order to enable the synthesis of microginin. The co-expression of the Ppt from a microginin producing strain would be preferred. Other Ppt's with a broad specificity even from heterotophic organisms like *Bacillus* sp. are also suitable.

In one embodiment of the invention the invention relates to a method of producing a microginin, comprising culturing a cell under conditions under which the cell will produce microginin, wherein said cell comprises a nucleic acid encoding a recombinant microginin, according to the invention, and wherein said cell does not produce the microginin in the absence of said nucleic acid.

The inventors have identified nucleic acid sequences which for the first time make it possible to detect nucleic acids encoding a microginin synthetase enzyme complex. This has been extremely difficult, due to the fact that other gene clusters which encode non-ribosomal protein producing complexes share sequence similarity with the present cluster claimed herein. Such primers or probes according to the invention are selected from the group of, a) nucleic acid according to SEQ ID NO. 49 (Primer A), b) nucleic acid according to SEQ ID NO. 50 (Primer B), c) nucleic acid according to SEQ ID NO. 51 (Primer C), d) nucleic acid according to SEQ ID NO. 52 (Primer D), e) nucleic acid according to SEQ ID NO. 53 (Primer E), f) nucleic acid according to SEQ ID NO. 54 (Primer F), g) nucleic acid according to SEQ ID NO. 55 (Primer G), h) nucleic acid according to SEQ ID NO. 56 (Primer H), i) nucleic acid according to SEQ ID NO. 57 (Primer I) and j) nucleic acid according to SEQ ID NO. 58 (Primer J). It is known to one skilled in the art that such primers or probes may be altered slightly and still accomplishes the task of specifically detecting the desired target sequence. Such alterations in sequence are equally encompassed by the invention. The primers or probes according to the invention may be applied in hybridization reactions and/or amplification reactions. Such reactions are known to one skilled in the art.

The invention also concerns a method for detecting a microginin synthetase gene cluster in a sample wherein, one or more of the nucleic acids according to the invention are, applied in an amplification and/or a hybridization reaction.

In a preferred embodiment of the method according to the invention primers D and F or H and J or E and I or E and A are added to a PCR reaction mixture comprising a sample and wherein, presence of an amplification product represents presence of microginin synthetase gene cluster and absence of an amplification product represents absence of a microginin synthetase gene cluster. As can be seen from the examples (example 3 below), certain combinations are preferred. Samples may be isolated DNA, prokaryotic cells stemming from plates or liquid cultures.

When performing an amplification reaction with primers D and F the most preferred amplification conditions are as follows: a) denaturing, b) 48° C. annealing and c) elongation (product size: 675 bp). These temperatures may vary a bit in the range of 2-8 degrees C.

When performing an amplification reaction with primers H and J the most preferred amplification conditions are as follows: a) denaturing, b) 54° C. annealing and c) elongation (product size: 1174 bp). These temperatures may vary a bit in the range of 2-8 degrees C.

When performing an amplification reaction with primers E and I the most preferred amplification conditions are as follows: a) denaturing, b) 56° C. annealing and c) elongation (product size: 1279 bp). These temperatures may vary a bit in the range of 2-8 degrees C.

When performing an amplification reaction with primers E and A the most preferred amplification conditions are as follows: a) denaturing, b) 57° C. annealing and c) elongation (product size: 621 bp). These temperatures may vary a bit in the range of 2-8 degrees C. Molarity is most commonly 0.2-1.0 µM for the primers. Buffers and other reagents depending on polymerase used.

When performing hybridisation reactions the above nucleic acids are usually labeled. Such labels may be radioactive or non-radioactive, such as fluorescent. The nucleic acid primers or probes may be applied, e.g. for the screening of libraries.

The invention also relates to antibodies against a peptide according to SEQ ID NO. 1 (A*).

The creation of such antibodies is known to one skilled in the art. The antibodies may be polyclonal or monoclonal. Such antibodies may be labeled or non-labeled, they may also be altered in other form, such as humanized.

The inventors have astonishingly found that newly identified peptide repeat spacer sequences (SP) may be placed adjacently to MAs I in order to create novel hybrid gene clusters. These SPs act by spacing the novel activity or domain so that it is functionally active in the microginin synthetase enzyme complex.

The invention thus, further relates to nucleic acids encoding a peptide repeat spacer sequence (SP) wherein, the peptide sequence comprises at least 4 glycin amino acids per single repeat unit (SRU) or, at least 5 proline and/or leucin amino acids per SRU. A SRU within the SP is between 7 and 15 amino acids in length and, the SP comprises between 2 and 10 SRUs.

The invention further relates to peptides of a peptide repeat spacer sequence (SP) wherein, the peptide sequence comprises at least 4 glycin amino acids or, at least 5 proline and/or leucin amino acids, the single repeat unit (SRU) within the SP is between 7 and 15 amino acids in length and, the SP comprises between 2 and 10 SRU. In a preferred embodiment of the invention the SRU is between 9 and 13 amino acids in length in a particularly preferred embodiment the SRU is eleven amino acids in length. In a preferred embodiment the SP comprises between 3 and 9 SRU.

In a preferred embodiment the nucleic acid encoding the peptide repeat spacer sequence (SP) according to the invention, encodes a peptide SRU as shown in SEQ ID NO. 20 or SEQ ID NO. 21. In a further embodiment the peptide repeat spacer sequence (SP) according to the invention, comprises or contains a sequence as shown in SEQ ID NO. 20 or SEQ ID NO. 21. In a further embodiment the nucleic acid according to the invention has a sequence as laid down in SEQ ID NO. 43 or SEQ ID NO. 44.

Not only by means of the above mentioned SPs but in particular because of these the inventors are able to create enzyme complexes resulting in microginin variants which may not be found in nature. This is an essential aspect of the present invention. The invention provides for, for the first time a simple method of producing recombinant microginin variants comprising, modifying the nucleic acid according to the invention in vitro or in vivo, growing a recombinant cell comprising said recombinantly modified nucleic acid encoding a microginin synthetase under conditions which lead to synthesis of a microginin and, recovering the synthesized microginin.

In a preferred embodiment of said method according to the invention, said modifying of said nucleic acid may be an action selected from the group of one or more of the following actions: a) inactivation of one or more of the MTs present, b) substitution of one or more of the MTs present with a halogenase, a sulfatase, a glycosylase, a racemase, an O-methyltransferase or a C-methyltransferase, c) inactivation of the MO, d) substitution of the MO with a halogenase, a sulfatase, a glycosylase, a racemase, an O-methyltransferase or a C-methyltransferase, e) inactivation of the AMT, f) substitution of the AMT with a halogenase, a sulfatase, a glycosylase, a racemase, an O-methyltransferase or a C-methyltransferase, g) inactivation of the PKS module, h) substitution of the entire PKS module with an alternative PKS module and/or substitution of one or more of the domains (KS, AT, ACP) therein, i) inactivation of the A* domain, j) substitution of the A* domain with alternative A domains, k) inactivation of one or more of the NRPS modules and l) substitution of one or more of the NRPS modules with alternative NRPS modules and/or substitution of one or more of the domains (C, A, T) therein.

Halogenases, sulfatases, glycosylases, racemases, O-methyltransferases or C-methyltransferases are known from prokaryotes. These enzymes are encoded by genes of the secondary metabolism in particular NRPS/PKS systems.

Alternative PKS-systems, entire modules as well as single domains (KS, AT, ACP) are found in cyanobacteria as well as Actinomycetes, Myxobacteria, *Bacillus* among the bacteria.

Alternative NRPS-systems, entire modules as well as single domains (C, A, T) are found in cyanobacteria as well as Actinomycetes, Myxobacteria, *Bacillus* among the bacteria.

In a preferred embodiment the above are from cyanobacteria.

It is important to note, that said inactivation and/or substitution may done in many ways, e.g. inactivation may imply deleting the complete activity or domain, or may imply inactivation by means of a single nucleotide exchange.

The methods are known to those skilled in the art and comprise basic molecular biological methods such as DNA isolation, restriction digestion, ligation, transformation, amplification etc.

In a preferred embodiment said alternative modules or domains which are used for substitution of the original module or domain, additionally may comprise one or more SP nucleic acids according to the invention located adjacently upstream of the module or domain used for substitution and one or more SP nucleic acids according the invention located adjacently downstream of the module or domain used for substitution. Thus, in this embodiment of the invention a construct is made comprising the domain which is to be entered into the original nucleic acid according to the invention, further comprising one or more SPs located adjacently in an upstream and downstream manner. This construct is then ligated into the original microginin synthetase encoding nucleic acid. The resultant construct is then brought into a host by means of transformation for either a) integration into the host chromosome or b) with a self-replicating vector.

The polypeptides, i.e. proteins can be any of those described above but with not more than 10 (e.g., not more than: 10, nine, eight, seven, six, five, four, three, two, or one) conservative substitutions. Conservative substitutions are known in the art and typically include substitution of, e.g. one polar amino acid with another polar amino acid and one acidic amino acid with another acidic amino acid. Accordingly, conservative substitutions preferably include substitutions within the following groups of amino acids: glycine, alanine, valine, proline, isoleucine, and leucine (non polar, aliphatic side chain); aspartic acid and glutamic acid (negatively charged side chain); asparagine, glutamine, methionine, cysteine, serine and threonine (polar uncharged side chain); lysine, histidine and arginine; and phenylalanine, tryptophane and tyrosine (aromatic side chain); and lysine, arginine an histidine (positively charged side chain). It is well known in the art how to determine the effect of a given substitution, e.g. on $pK_1$ etc. All that is required of a polypeptide having one or more conservative substitutions is that it has at least 50% (e.g., at least: 55%; 60%; 65%, 70%; 75%; 80%; 85%; 90%; 95%; 98%; 99%; 99.5%; or 100% or more) of the ability of the unaltered protein according to the invention.

In preferred embodiments the polynucleotides, i.e. nucleic acids of the present invention also comprise nucleic acid molecules which are at least 85%, preferably 86%, 87%, 88%, 89%, 90%, 91%, 92%, 93%, 94%, 95%, 96%, 97%, 98%, or 99% identical to those claimed herein.

The determination of percent identity between two sequences is accomplished using the mathematical algorithm of Karlin and Altschul (1993) *Proc. Natl. Acad. Sci. USA* 90: 5873-5877. Such an algorithm is incorporated into the BLASTN and BLASTP programs of Altschul et al. (1990) J. Mol. Biol. 215: 403-410. BLAST nucleotide searches are performed with the BLASTN program, score=100, word length=12, to obtain nucleotide sequences homologous to the nucleic acids according to the invention. BLAST protein searches are performed with the BLASTP program, score=50, wordlength=3, to obtain amino acid sequences homologous to the EPO variant polypeptide, respectively. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used.

FIGURES

Figure 2:
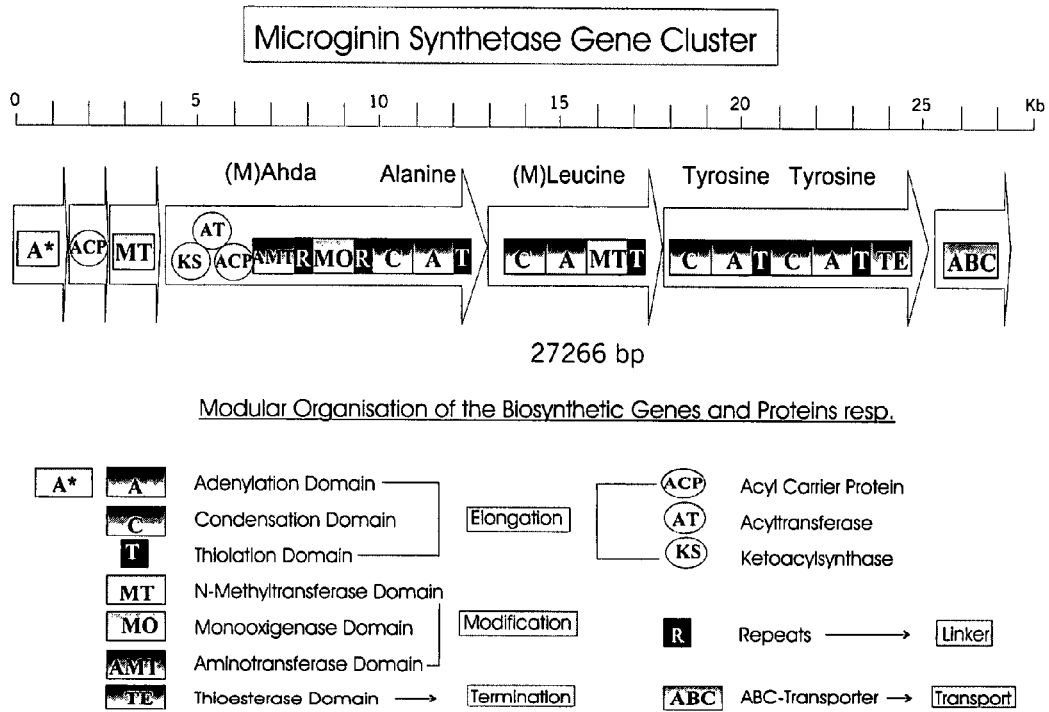
Figure 2:
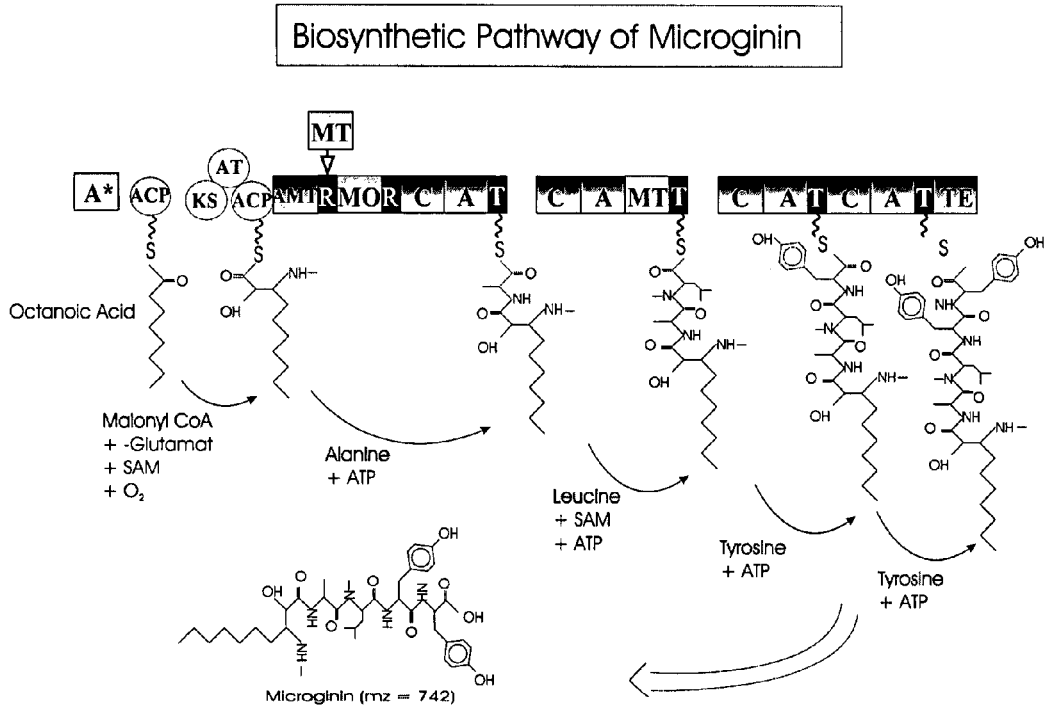

FIG. 1 depicts the structure of microginin.
FIG. 2 depicts the microginin synthetase gene cluster and the biosynthetic pathway of microginin.

EXAMPLES

Example 1

Method for Detecting Gene Clusters According to the Invention

Strains carrying a gene cluster encoding a microginin synthetase complex can be distinguished from strains not carrying such a gene cluster performing a PCR reaction using RedTaq ReadyMix PCR Reaction Mix with $MgCl_2$ (Sigma) and primer pairs and the corresponding annealing temperatures as described. In particular the PCR conditions are as follows: an initial denaturation for 1 minutes at 95° C., followed by 30 cycles of denaturation at 95° C. for 30 seconds, elongation at said annealing temperatures for 30 seconds and extension at 72° C. for 1 kb of product size.

Example 2

Method for Optimised Cultivation of Microginin Producing *Microcystis* spp

Strains. Media: Bg 11 (for cultivation of cyanobacteria)

Aeration: air containing 0.3-3.0% carbon dioxide

Light intensity: 40-100 $pE/m^2 \cdot s$ (diameter of illuminated culture vessels of photobioreactor d=4-12 cm)

Light quality: Additional red light illumination with 25 $\mu E/m^2 \cdot S$ for 24-48 hours before harvesting.

Cell density at harvest: $OD_{750nm}$ 1-2

Tables

TABLE 1

| | |
|---|---|
| SEQ ID NO. 1 A* | MTINYGDLQEPFNKFSTLVELLRYRASSQPERLAYIFLRDGEIE EARLTYGELDQKARAIAAYLQSLEAEGERGLLLYPPGLDFISAF FGCLYAGVVAIPAYPPPRRNQNLLRLQAIIADSQARFTFTNAALF PSLKNQWAKDPELGAMEWIVTDEIDHHLREDWLEPTLEKNSLAF LQYTSGSTGTPKGVMVSHHNLLINSADLDRGWGHDQDSVMVTWL PTPHDMGLIYGVIQPLYKGFLCYMMSPASFMERPLRWLQALSDK KATHSAAPNFAYDLCVRKIPPEKRATLDLSHWCMALNGAEPVRA EVLKKFAEAFQVSGFKATALCPGYGLAEATLKVTAVSYDSPPYF YPVQANALEKNKIVGATETDTNVQTLVGCGWTTIDTQIVIVNPE TLKPCSPEIVGEIWVSGSTIAQGYWGKPQETQETFQAYLADTGA GPFLRTGDLGFIKDGELFITGRLKEIILIRGRNNYPQDIELTVQ NSHPALRPSCGAAFTVENKGEEKLVVVQEVERTWLRKVDIDEVK RAIRKAVVQEYDLQVYAIALIRTGSLPKTSSGKIQRRSCRAKFL EGSLEILG |
| SEQ ID NO. 2 ACP | MSTEIPNDKKQPTLTKIQNWLVAYMTEMMEVDEDEIDLSVPFDE YGLDSSMAVALIADLEDWLRRDLHRTLIYDYPTLEKLAKQVSEP |
| SEQ ID NO. 3 KS | MEPIAIIGLACRFPGADNPEAFWQLMRNGVDAIADIPPERWDIE RFYDPTPATAKKMYSRQGGFLKNVDQFDPQFFRISPLEATYLDP QQRLLLEVTWEALENAAIVPETLAGSQSGVFIGISDVDYHRLAY QSPTNLTAYVGTGNSTSIAANRLSYLFDLRGPSLAVDTACSSSL VAVHLACQSLQSQESNLCLVGGVNLILSPETTVVFSQARMIAPD SRCKTFDARADGYVRSEGCGVVVLKRLRDAIQDGDRILAVIEGS AVNQDGLSNGLTAPNGPAQQAVIRQALANAQVKPAQISYVEAHG TGTELGDPIEVKSLKAVLGEKRSLDQTCWLGSVKTNIGHLEAAA GMAGLIKVVLCLQHQEIPPNLHFQTLNPYISLADTAFAIPTQAQ PWRTKPPKSGENGVERRLAGLSSFGFGGTNSHVIL |
| SEQ ID NO. 4 AT | VFLFAGQGSQYVGMGRQLYETQPIFRQTLDRCAEILRPHLDQPL LEILYPADPEAETASFYLEQTAYTQPTLFAFEYALAQLWRSWGI EPAAVIGHSVGEYVAATVAGALSLEEGLTLIAKRAKLMQSLPKN GTMIAVFAAEERVKAVIEPYRTDVAIAAVNGPENFVISGKAPII AEIIIHLTAAGIEVRLPKVSHAFHSHLLEPILDSLEQEAAAIS YQPLQIPLVANLTGEVLPEGATIEARYWRNHARNPVQFYGSIQT LIEQKFSLFLEVSPKPTLSRLGQQCCPERSTTWLFSLALPPQEE EQSLLNSLAILYDSQGAE |
| SEQ ID NO. 5 ACP 2 | ITLQTLVGNLLQLSPADVNVHTPFLEMGADSIVMVEAVRRIENT YNVKIAMRQLFEELSTLDALATYL |
| SEQ ID NO. 6 AMT | KEMLYPIVAVQRSQGSRIWDVDGNEYIDMTMGQGVTLFGHQPDFI MSALQSQLTEGIHLNPRSPIVGEVAALICELTGAERACFCNSGT EAVMAAIRIARATTGRSKIALFEGSYHGHADGTLFRNQIIDNQL HSFPPLALGVPPSLSSDVVVLDYGSAEALNYLQTQGQDLAAVLVE PIQSGNPLLQPQQFLQSLRQITSQMGEILFDEMITGFRSHPGG AQALFGVQADIATYGKVVAGGMPIGVIAGKAHYLDSIDGGMWRY GDKSYPGVDRTFFGGTFNQHPLAMVAARAVLTHLKEQGPGLQQQ LTERTAALADTLNHYFQAEEVPIKIEQFSSFFRRFALSGNLDLLF YHMVEKGIYVWEWRKHFLSTAHTEADLAQFVQAVKDSITELR |
| SEQ ID NO. 7 C | GGDQVPLTEAQRQLWILAQLGDNGSVAYNQSVTLQLSGPLNPVA MNQAIQQISDRHEALRTKINAQGDSQEILPQVEINCPILDFSLD QASAQQQAEQWLKEESEKPFDLSQGSLVRWHLLKLEPELHLLVL TAHHIISDGWSMGVILRELGELYSAKCQGVTANLKTPKQFRELI EWQSQPSQGEELKKQQAYWLATLADPPVLNLPTDKPRPALPSYQ ANRRSLTLDSQFTEKLKQFSRKQGCTLLMTLLSVYNILVHRLTG QDDILVGLPASGRGLLDSEGMVGYCTHFLPIRSQLA |
| SEQ ID NO. 8 A | TYSELNCRANQLALHYLQKLGVGPEVLVGILVERSLEMIVGLLG ILKAGGAYVPLDPDYPPERLQFMLEDSQFFLLLTQQHLLESFAQ SSETATPKIICLDSDYQIISQANNINPENSVTTSNLAYVIYTSG STGKPKGVMNNHVAISNKLLWVQDTYPLTTEDCILQKTPFSFDV SVWELFWPLLNGARLVFAKPNGHKDASYLVNLIQEQQVTTLHFV SSMLQLFLTEKDVEKCNSLKRVICSGEALSLELQERFFARLVCE LHNLYGPTEAAIHVTFWQCQSDSNLKTVPIGRPIANIQIYILDS HLQPVPIGVIGELHIGGVGLARGYLNRPELTAEKFIANPFASLD PPLTPLDKGGDESYKTFKKGGEQPSRLYKTGDLARYLPDGKIEY LGRIDNQVKIRGFRIELGEIEAVLLSHPQVREAVV |
| SEQ ID NO. 9 T | EAIAAIFGQVLKLEKVGIYDNFFEIGGNSLQATQVISRLRESFA LELPLRRLFEQPTVADLALAV |
| SEQ ID NO. 10 C2 | PRDGQLPLSFAQSRLWFLYQLEGATGTYNMTGALSLSGPLQVEA LKQALRTIIQRHEPLRTSFQSVDGVPVQVINPYPVWELAMVDLT GKETEAEKLAYQESQTPFDLTNSPLLRVTLLKLQPEKHILLINM HHIISDGWSIGVFVRELSHLYRAFVAGKEPTLPILPIQYADFAV WQREWLQGKVLAAQLEYWKRQLADAPPLLELPTDRPRPAIQTFQ GKTERFELDRKLTQELKALSQQSGCTLFMTLLAAFGVVLSRYSG QTDIVIGSAIANRNRQDIEGLIGFFVNTLALRLDLS |
| SEQ ID NO. 11 A2 | TYGELNHRANQLAHYLQSLGVTKEQIVGVYLERSLEMAIGFLGI LKAGAAYLPIDPEYPSVRTQFILEDTQLSLLLTQAELAEKLPQT QNKIICLDRDWPEITSQPQTNLDLKIEPNNLAYCIYTSGSTGKP KGVLISHQALLNLIFWHQQAFEIGPLHKATQVAGIAFDATVWEL WPYLTTGACINLVPQNILLSPTDLRDWLLNREITMSFVPTPLAE KLLSLDWPNHSCLKTLLLGGDKLHFYPAASLPFQVINNYGPTEN TVVATSGLVKSSSSHHFGTPTIGRPIANVQIYLLDQNLQPVPIG VPGELHLGGAGLAQGYLNRPELTAEKFIANPFDPPLTPLDKGGE EPSKLYKTGDLARYLPDGNVEFLGRIDNQVKIRGFRIETGEIEA VLSQYFLLAESVV |
| SEQ ID NO. 12 T2 | AQLTQIWSEVLGLERIGVKDNFFELGGHSLLATQVLSRINSAFG LDLSVQIMFESPTIAGIAGYI |
| SEQ ID NO. 13 C3 | ARDGHLPLSFAQQRLWFLHYLSPDSRSYNTLEILQIDGNLNLTV LEQSLGELINRHEIFRTTFPTVSGEPIQKIALPSRFQLKVDNYQ DLDENEQSAKIQQVAELEAGQAFDLTVGPLIQFKLLQLSPQKSV LLLKMHHIIYDGWSFGLIRELSALYEAFLKNLANPLPALSIGY ADFAVWQRQYLSGEVLDKQLNYWQEQLATVSPVLTLPTDRPRPA IQTFQGGVERFQLDQNVTQGLKKLGQDQVATLFMTLLAGFGVLL SRYSGQSDLMVGSPIANRNQAAIEPLIGFFANTLALRINLS |
| SEQ ID NO. 14 A3 | TYTELNHRANQLAHYLQTLGVGAEVLVGISLERSLEMIIGGLLI LKVGGAYLPLDPDYPTERLQLMLEDSQVPFLITHSSLLAKLPPS QATLICLDHIQEQISQYSPDNLQCQLTPANLANVIYTSGSTGKP KGVMVEHKGLVNLALAQIQSFAVHNHNSRVLQFASFSFDACISEI LMTFGSGATLYLAQKDALLPGQPLIERLVKNGITHVTLPPSALV VLPQEPLRNLETLIVAGEACSLDLVKQWSIDRNFFNAYGPTEAS VCATIGQCYQDDLKVTIGKAIANVQIYILDAFLQPVPVGVSGEL YIGGVGVARGYLNRPELTQEKFIANPFSNDPSRLYKTGDLARY LPDGNIEYLGRIDNQVKIRGFRIELGEIEAVLSQCPDVQNTAV |
| SEQ ID NO. 15 T3 | EILAQIWGQVLKIERVSREDNFFELGGHSLLATQVMSRLRETFQ VELPLRSLFTAPTIAELALTI |
| SEQ ID NO. 16 C4 | NDSANLPLSFAQQRLWFLDQLEPNSAFYHVGGAVRLEGTLNITA LEQSLKEIINRHEALRTNFITIDGQATQIIHPTINWRLSVVDCQ NLTDTQSLEIAEAEKPFNLAQDCLFRATLFVRSPLEYHLLVTMH HIVSDGWSIGVFFQELTHLYAVYNQGLPSSLTPIKIQYADFAVW QRNWLQGEILSNQLNYWREQLANAPAFLPLPTDRPRPAIQTFIG SHQEFKLSQPLSQKLNQLSQKHGVTLFMTLLAAFATLLYRYTGQ ADILVGSPIANRNRKEIEGLIGFFVNTLVLRLSLD |
| SEQ ID NO. 17 A4 | TYAELNHQANQLVHYLQTLGIGPEVLVAISVERSLEMIIGGLLAI LKACGAYLPLAPDYPTERLQFMLEDSQASFLITHSSLLEKLPSS QATLICLDHIQEQISQYSPDNLQSELTPSNLANVIYTSGSTGKP KGVMVEHRGLVNLASSQIQSFAVKNNSRVLQFASFSFDACISEI LMTFGSGATLYLAQKNDLLPGQPLMERLEKNKITHVTLPPSALA VLPKKPLPNLQTLIVAGEACPLDLVKQWSVGRNFFNAYGPTETS VCATIGQCYQDDLKVTIGKAIANVQIYILDAFLQPVPIGVPGEL YIGGVGVARGYLNRPELTAERFIPNPFDPPLTPLKKGGDKSYET FKKGEEQPSKLYKTGDLARYLPDGNIEYLGRIDNQVKIRGFRIE LGEIEAVLSQCPDVQNTAV |
| SEQ ID NO. 18 T4 | LQLAQIWSEILGINNIGIQENFFELGGHSLLAVSLINRIEQKLD KRLPLTSLFQNGTIASLAQLL |
| SEQ ID NO. 19 TE | TPFFAVHPIGGNVLCYADLARNLGTKQPFYGLQSLGLSELEKTV ASIEEMAMIYIEAIQTVQASGPYYLGGWSMGGVIAFEIAQQLLT QGQEVALLALIDSYSPSLLNSVNREKNSANSLTEEFNEDINIAY SFIRDLASIFNQEISFSGSELAHFTSDELLDKFITWSQETNLLP SDFGKQQVKTWFKVFQINHQALSSYSPKTYLGRSVFLGAEDSSI KNPGWHQ |

TABLE 1-continued

SEQ ID NO. 20 MO
FSLYYFGSYEAEFNPNKYNLLFEGAKFGDRAGFTALWIPERHFH
AFGGFSPNPSVLAAALARETKQIQLRSGSVVLPLHNSIRVAEEW
AVVDNLSQGRVGIAFASGWHPQDFVLAYQSFGQHRELMFQEIET
VQKLWRGEAITVPDGKGQRVEVKTYPQPMQSQLPSWITIVNNPD
TYIRAGAIGANILTNLMGQSVEDLARNIALYRQSLAEHGYDPAS
GTVTVLLHTFVGKDLEQVREQARQPFGQYLTSSVGLLQNMVKSQ
GMKVDFEQLRDEDRDFLLASAYKRYTETSALIGTPESCRQIIDH
LQSIGVDEVACFIDFGVDEQTVLANLPYLQSLKDLYQ

SEQ ID NO. 21 SP 1
IDPPLTPLDKGIDPPLTPLDKGIDPPLTPLDKG

SEQ ID NO. 22 SP 2
PYQGGLGGDQSPYQGGLGGDQSPYQGGLGGDQSPYQGGLGGDQS
PYQGGLGGDQSPYQGELGGDQSPYQGGLGGDQV

SEQ ID NO. 23 MT
PASEMREWVENTVSRILAFQPERGLEIGCGTGLLLSRVAKHCLE
YWATDYSQGAIQYVERVCNAVEGLEQVKLRCQMADNFEGIALHQ
FDTVVLNSIIQYFPSVDYLLQVLEGAINVIGERGQIFVGDVRSL
PLLEPYHAAVQLAQASDSKTVEQWQQQVRQSVAGEEELVIDPTL
FLALKQHFPQISWVEIQPKRGVAHNELTQFRYDVTLHLETINNQ
ALLSGNPTVITWLNWQLDQLSLTQIKDKLLTDKPELWGIRGIPN
QRVEEALKIWEWVENAPDVETVEQLKLLKQQVDTGINPEQVWQ
LAESLGYTAHLSWWESSQDGSFDVIFQRNSEAEDSKKLTLSKLA
FWDEKPFKIKPWSDYTNNPLRGKLVQKLIP

SEQ ID NO. 24 MT 2
MTNYGKSMSHYYDLVVGHKGYNKDYATEVEFIHNLVETYTTEAK
SILYLGCGTGYHAALLAQKGYSVHGVDLSAEMLEQAKTRIEDET
IASNLSFSQGNICEIRLNRQFNVVLALPHVVNYQTTNQNLLATF
ATVKNHLKAGGIFICDVSYGSYVLGEFKSRPTASILRLEDNSNG
NEVTYISELNFLTHENIVEVTHNLWVTMQENQLLENSRETHLQR
YLFKPEVELLADACELTVLDAMPWLEQRPLTNIPCPSVCFVIGH
KTTHSA

SEQ ID NO. 25 A* nucl acid
ATGACTATTAACTATGGTGATCTGCAAGAACCCTTTAATAAATT
CTCAACCCTAGTTGAATTACTCCGTTATCGGGCAAGCAGTCAAC
CGGAACGCCTCGCCTATATTTTCTGCGAGACGGAGAAATCGAA
GAAGCTCGTTTAACCTATGGGGAACTGGATCAAAAGGCTAGGGC
GATC
GCCGCTTATCTACAATCCTTAGAAGCCGAGGGCGAAAGGGGTTT
ACTGCTCTATCCCCCAGGACTAGATTTTATTTCAGCTTTTTTG
GTTGTTTATATGCGGGAGTCGTTGCCATTCCCGCCTATCCACCC
CGACGGAATCAAACCTTTTCGCGTTTACAGGCGATTATTGCCGA
TTCTCAAGCCCGATTTACCTTCACCAATGCCGCTCTATTTCCCA
GTTTAAAAAACCAATGGGCTAAAGACCCTGAATTAGGAGCAATG
GAATGGATTGTTACCGATGAAATTGACCATCACCTCAGGGAGGA
TTGGCTAGAACCAACCCTCGAAAAAACAGTCTCGCTTTTCTAC
AATACACCTCTGGTTCAACGGGAACTCCAAAGGGAGTAATGGTC
AGTCACCATAATTTGTTGATTAATTCAGCCGATTTAGATCGTGG
TTGGGGCCATGATCAAGATAGCGTAATGGTCACTTGGCTACCGA
CCTTCCATGATATGGGTCTGATTTATGGGTTATTCAGCCTTTG
TACAAAGGATTTCTTTGTTACATGATGTCCCCTGCCAGCTTTAT
GGAACGACCGTTACGTTGGTTACAGGCCCTTTCTGATAAAAAG
CAACCCATAGTGCGGCCCCAACTTTGCCTACGATCTTTGTGTG
CGGAAAATTCCCCCTGAAAAACGGGCTAGGTTAGACTTAAGCCA
TTGGTGCATGGCCTTAAATGGGGCCGAACCCGTCAGAGCGGAGG
TACTTAAAAAGTTTGCGGAGGCTTTTCAAGTTTCTGGTTTCAAA
GCCACAGCCCTTTGTCCTGGCTACGGTTTAGCAGAAGCCACCCT
GAAAGTTACGGCGGTTAGTTATGACAGTCCCCCTTACTTTTATC
CCGTTCAGGCTAATGCTTTAGAAAAAAAAATAAGATTGTGGGAGCC
ACTGAAACCGATACCAATGTGCAGACCCTCGTGGGC
TGCGGCTGGACAACGATTGATACTCAAATCGTCATTGTCAATCC
TGAAACCCTGAAACCTTGCTCCCCTGAAATTGTCGGCGAAATTT
GGGTATCAGGTTCAACAATCGCCCAAGGCTATTGGGAAAACCT
CAAGAGACTCAGGAAACCTTTCAAGCTTATTGGCAGATACAGG
AGCC
GGGCCTTTTCTGCGAACAGGAGACTTGGGCTTCATTAAAGATGG
TGAATTGTTTATCACAGGTCGGCTCAAGGAAATTATTCTGATTC
GAGGACGCAATAATTATCCCCAGGATATTGAATTAACCGTCCAA
AATAGTCATCCCGCTCTGCGTCCCAGTTGTGGGGCTGCTTTTAC
CGTTGAAAATAAGGGCGAAGAAAAGCTCGTGGTCGTTCAGGAAG
TGGAGCGCACCTGGCTCCGT
AAGGTAGATATAGATGAGGTAAAAAGAGCCATTCGTAAAGCTGT
TGTCCAGGAATATGAT
TTACAGGTTTATGCGATCGCGCTGATCAGGACTGGCAGTTTACC
AAAAACCTCTAGCGGTAAAATTCAGCGTCGTAGCTGTCGGGCCA
AATTTTTAGAGGGAAGCCTGGAAATTTTGGGCTAA SEQ ID NO. 26 ACP nucl acid
ATGTCCACAGAAATCCCAAACGACAAAAAACAACCGACCCTAAC
GAAAATTCAAACTGG
TTAGTGCATTACATGACAGAGATGATGGAAGTGGACGAAGATGA
GATTGATCTGAGCGTTCCCTTTGATGAATATGGTCTCGATTCTT
CTATGGCAGTTGCTTTGATCGCTGATCTAGAGGATTGGTTACGA
CGAGATTTACATCGCACCCTGATCTACGATTATCCAACTCTAGA
AAAGTTGGCTAAACAGGTTAGTGAACCCTGA SEQ ID NO. 27 KS nucl acid
ATGGAACCCATCGCAATTATTGGTCTTGCTTGCCGCTTTCCAGG
GGCTGACAATCCAGAAGCTTTCTGGCAACTCATGCGAAATGGGG
TGGATGCGATCGCCGATATTCCTCCTGAACGTTGGGATATTGAG
CGTTTCTACGATCCCACACCTGCCACTGCCAAGAAGATGTATAG
TCGCCAGGGCGGTTTTCTAAAAAATGTCGATCAATTTGACCCTC
AATTTTTCCGAATTTCTCCCCTAGAAGCCACCTATCTAGATCCT
CAACAAAGACTGCTACTGGAAGTCACCTGGGAAGCCTTAGAAAA
TGCTGCCATTGTGCCTGAAACCTTAGCTGGTAGCCAATCAGGGG
TTTTTATTGGTATCAGTGATGTGGATTATCATCGTTTGGCTTAT
CAAAGTCCTACTAACTTGACCGCCTATGTGGGTACAGGCAACAG
CACCAGTATTGCGGCTAACCGTTTATCATATCTGTTTGATTTGC
GTGGCCCCAGTTTGGCCGTAGATACCGCTTGCTCTTCTTCCCTC
GTCGCCGTTCACTTGGCCTGTCAGAGTTTGCAAAGTCAAGAATC
GAACCCTCTGCTTAGTGGGGGGAGTTAATCCATTTTGTCGCCAG
AGACAACCGTTGTTTTTTCCCAAGCGAGAATGATCGCCCCGAC
AGTCGTTGTAAAACCTTTGACGCGAGGGCCGAGTTGTATGTGCG
CTCGGAAGGCTGTGGAGTAGTCGTACTTAAACGTCTTAGGGATG
CCATTCAGGACGGCGATCGCATTTTAGCAGTGATTGAAGGTTCC
GCGGTGAATCAGGATGGTTTAAGTAATGGACTCACGGCCCCTAA
TGGCCCTGCTCAACAGGCGGTGATTCGTCAGGCCCTGGCAAATG
CCCAGGTAAAACCGGCCCAG
ATTAGCTATGTCGAAGCCCATGGCACGGGGACAGAATTGGGGGA
TCCGATCGAAGTTAAA
TCTCTGAAAGCGGTTTTGGGTGAAAAGCGATCGCTCGATCAAAC
CTGTTGGTCGGTTCTGTGAAAACCAACATTGGTCATTTAGAAG
CGGCGGCGGGAATGGCGGGTCTGATTAAAGTC
GTTCTCTGCCTACAACACCAAGAAATTCCCCCTAATCTCCACTT
TCAAACCCTTAATCCCTATATTTCCCTAGCTGACACAGCTTTTG
CGATTCCCACTCAGGCTCAACCCTGGCGGACCAAACCCCCTAAG
TCTGGTGAAAACGGTGTCGAACGACGTTTAGCAGGACTCAGTTC
CTTTGGGTTTGGGGGACAAATTCCCATGTGATTCTC SEQ ID NO. 28 AT nucl acid
GTTTTTCTATTTGCCGGTCAAGGTTCTCAATATGTAGGTATGGG
TCGTCAACTGTACGAAACCCAACCCATCTTTCGCAAACCTTGG
ATCGCTGTGCTGAAATCCTGCGACCCCATTTGATCAACCCCTC
TTAGAATTCTTTATCCTGTGACCCAGAAGCCGAAACAGCCAG
TTTTTACCTAGAGCAGACTGCCTATACCCAACCACTTTATTCG
CATTCGAGTATGCCCTAGCACAGTTATGGCGTTCCTGGGGAATA
GAACCGGCGGCAGTAATTGGTCACAGTGTCGGTGAATATGTGGC
GGCCACCGTTGCCGGAGCCTTAAGTCTAGAAGAAGGATTAACGC
TAATTGCCAAACGGGCAAAACTGATGCAGTCTCTCCCCAAGAAT
GGGACAATGATGGCCGTTTTTGCCGCAGAAGAGCGGGTTAAAGC
TGTTATTGAGCCTTATAGGACTGATGTAGCGATCGCTGCTGTTA
ATGGACAGAAAATTTTGTTATTTCAGGAAAAGCGCCGATTATT
GCTGAGATTATCATTAACGGCAGCAGAATAGAAGTTCG
TCCTCTCAAAGTTTCCCATGCTTTTCACTCGCACCTGTTGGAGC
CAATTTTAGATTCCTTAGAACAGGAAGCTGCTGCTATTTCCTAC
CAACCCCTGCAAATTCCCTTAGTTGCTAATTTAACGGGGAAGT
TCTACCAGAAGGAGCAATTGAGGCTCGTTACTGGCGAAATC
ATGCACGCAACCCTGTACAATTTTATGGGAGTATCCAAACGCTG
ATCGAGCAGAAATTCAGTCTTTTTTTAGAAGTTAGCCCTAAACC
GACTTTATCTCGATTGGGTCAACAATGTTGTCCAGAAAGATCGA
CCACTTGGCTATTTTCCCTCGCCCCTCCTCAAGAAGAAGAACAA
AGCCTACTAAATAGTTTGGCGATTCTCTATGATTCCCAAGGAGC
CGAA SEQ ID NO. 29 ACP 2 nucl acid
ATCACATTGCAAACCCTAGTGGGAAATTTACTGCAATTGTCCCC
TGCTGATGTCAATGTTCATACACCTTTCCTGGAGATGGGGCAG
ATTCCATTGTCATGGTTGAGGCGGTCAGACGGATTGAGAATACC
TATAACGTTAAAATTGCTATGCGTCAGTTATTTGAGGAGTATCC
TACTTTAGATGCTTTAGCTACTTATTTA SEQ ID NO. 30 AMT nucl acid
AAAGAGATGCTTTATCCCATTGTGCCCAACGTTCTCAAGGATC
AAGAATTTGGGATGTGGACGGTAATGAATATATTGATATGACGA
TGGGGCAAGGGGTAACGCTGTTTGGGCATCAA
CCAGACTTCATTATGTCGGCCCTACAAAGCCAACTCACTGAAGG
CATTCATCTCAATCCGCGATCGCCAATTGTGGGAGAAGTGGCCG
CCCTTAATTTGTGAACTAACAGGAGCCGAACGA
GCTTGTTTTGCAACTCTGGAACCGAAGCCGTAATGGCCGCTAT
TCGTATCGCCAGGGCAACAACAGGTCGGAGTAAAATTGCCCTCT TABLE 1-continued

```
              TTGAAGGCTCCTATCATGGACATGCGGACGGAACCCTTTTTAGG
              AACCAAATTATTGATAACCAACTCCACTCTTTTCCCCTAGCTCT
              AGGCGTTCCCCCCAGCCTTAGTTCCGATGTGGTGGTATTGGACT
              ATGGCAGTGCGGAAGCTCTGAACTATTTACAAACCCAGGGGCAG
              GATTTAGCGGCGGTCTTAGTAGAACCAATTCAAAGTGGCAATCC
              TCTACTCCAACCCCAACAATTTCTCCAAAGTCTGCGCACAAATTA
              CCAGTCAAATGGGCATTGCCCTGATTTTTGATGAAATGATTACG
              GGTTTTCGATCGCACCCAGGGGGAGCGCAAGCTTTATTTGGAGT
              ACAGGCGGATATTGCCACCTATGGCAAAGTAGTTGCGGGAGGAA
              TGCCCATTGGAGTTATTGCAGGTAAGGCCCATTATCTGGACAGC
              ATTGACGGGGAATGTGCGTTATGGCGATAAATCCTATCCTGG
              GGTGGACAGAACCTTTTTTGGGGGAACCTTTAATCAGCATCCGT
              TAGCAATGGTAGCGGCTAGGGCTGTCCTGACCCATTTAAAGGAG
              CAGGGGCCAGGTCTGCAACAACAATTAACTGAACGCACTGCGGC
              CTTAGCCGATACACTG
              AATCATTATTTTCAAGCCGAAGAAGTTCCTATTAAAATCGAACA
              GTTTAGTTCTTTCTTCCGGTTTGCCCTCTCTGGCAATTTGGATT
              TACTTTTCTATCACATGGTAGAAAAAGGTATTTATGTCTGGGAA
              TGGCGTAAACATTTTCTTTCAACCGCCCATACGGAAGCCGATCT
              TGCCCAATTTGTCCAAGCGGTTAAGGATAGCATCACAGAATTGC
              GT

SEQ ID        GGGGGGGATCAAGTCCCTCTCACCGAAGCCCAACGACAACTGTG
NO. 31        GATTTTGGCTCAATTAGGAGACAACGGCTCTGTGGCCTATAACC
C nucl        AATCAGTGACATTGCAATTAAGTGGCCCATTAAATCCCGTCGCA
acid          ATGAATCAAGCTATTCAACAAATCAGCGATCGCCATGAAGCGTT
              ACGAACCAAAATTAATGCCCAGGGAGATAGTCAAGAAATCCTGC
              CCCAGGTCGAAATTAACTGC
              CCTATCTTAGACTTCAGTCTTGACCAAGCTTCGGCCCAACAGCA
              AGCAGAACAATGGTTAAAGGAAGAAAGTGAAAAACCCTTTGATT
              TGAGCCAGGGTTCTCTCGTGCGTTGGCATCTACTCAAATTAGAA
              CCAGAATTACATTTGTTAGTATTAACGGCCCATCACATTATCAG
              TGACGGTTGGTCAATGGGGGTAATCCTTCGGGAATTAGGAGAGT
              TATATTCAGCCAAATGTCAGGGTGTTACGGCTAATCTTAAAACC
              CCAAAACAGTTTCGAGAATTGATTGAATGGCAAAGCCAGCCAAG
              CCAAGGGGAAGAACTGAAAAAACAGCAAGCCTATTGGTTAGCAA
              CCCTTGCC
              GATCCCCCTGTTTTGAATTTACCCACTGACAAACCTCGTCCAGC
              TTTACCCAGTTACCAAGCTAATCGTCGAAGTCTAACTTTAGATA
              GCCAATTTACAGAAAAACTAAAGCAATTTAGTCGTAAACAGGGC
              TGTACCTTGCTGATGACCCTGTTATCGGTTATAACATTCTCGT
              TCATCGTTTGACGGGACAGGATGATATTCTGGTGGGTCTGCCAG
              CCTCTGGACGGGGCTTTTAGATAGTGAAGGTATGGTGGGTTAT
              TGCACCCATTTTTTACCAATTCGCAGTCAATTAGCA SEQ ID        ACTTACAGTGAATTAAATTGTCGAGCCAATCAGTTAGCACATTA
NO. 32        TTTACAAAAATTAGGAGTTGGGCCAGAGGTCTTAGTCGGTATTT
A nucl        TGGTCGAACGTTCTTTAGAAATGATTGTCGAGTTGTTAGGGATT
acid          CTCAAGGCTGGGGGAGCCTATGTACCTCTTGATCCTGACTATCC
              CCCTGAACGTCTTCAATTTATGTTAGAAGATAGTCAATTTTTTC
              TCCTCTTAACCCAACAGCATTTACTGGAATCTTTTGCTCAGTCT
              TCAGAAACGGCTACTCCCAAGATTATTTGTTTGGATAGCGACTA
              CCAAATTATTTCCCAGGCAAAGAATATTAATCCCGAAAATTCAG
              TCACAACGAGTAATCTCTATGTAATTTATACCTCTGGTTCA
              ACAGGTAAACCGAAGGGCGTGATGAATAATCATGTTGCTATTAG
              TAATAAATTGTTATGGGTACAAGACACTTATCCTCTAACCACAG
              AAGACTGTATTTTACAAAAAACTCCCTTTAGTTTTGATGTTTCA
              GTGTGGGAATTATCTGGCCCCTACTAAACGGAGCGCGTTTGGT
              TTTTGCCAAGCCGAATGGCCATAAAGATGCCAGTTACTTAGTCA
              ATCTGATTCAAGAGCAACATAACAACGCTACATTTTGTGTCT
              TCTATGCTACAGCTTTTTCTGACAGAAAAGACGTAGAAAAATG
              TAATAGTCTTAAACGAGTCATTTGTAGTGGTGAAGCCCTTTCTT
              TAGAGCTTCAAGAACGTTTTTTGCTCGTTTAGTCTGTGAATTA
              CACATCTTTATGGACCGACAGAACCGCTACTTACATGTCACATT
              TTGGCAATGTCAATCAGATAGCAATTTGAAAACAGTACCCATTG
              GTCGGCCGATCGCTAATATCCAAATTTACATTTTAGACTCTCAT
              TTCAGCCAGTACCTATTGGAGTAATCGGAGAATTGCACATTGGT
              GGGGTTGGTTTGGCGCGGGGTTATTTAAACAGGCCTGAGTTAAC
              GGCGGAGAAATTTATTGCAAATCCGTTTGCTTCCCTTGATCCCC
              CCTAACCCCCCTTGATAAGGGGGAGATGAGAGCTATAAAACT
              TTTAAAAAGGGGGAGAGCAACCATCAAGATTGTATAAA
              ACGGGAGATTTAGCTCGTTATTTACCCGATGGCAAGATTGAGTA
              TCTAGGGCGCATTGATAATCAGGTAAAAATTCGCGGTTTCCGGA
              TTGAATTGGGGGAAATTGAAGCGGTTTTGCTATCCCATCCCCAG
              GTACGAGAAGCGGTCGTT
```

```
SEQ ID        GAGGCGATCGCCGCTATTTTTGGTCAAGTTTTAAAACTGGAAAA
NO. 33        AGTGGGAATTTATGATAACTTTTTTGAGATCGGCGGTAATTCTT
T nucl        TGCAAGCCACTCAAGTTATTTCACGCTTACGAGAAAGTTTTGCC
acid          CTAGAGTTTGCCCTTGCGTCGCCTGTTTGAACAACCGACTGTGGC
              GGATTTGGCTTTAGCCGTA SEQ ID        CCTCGTGATGGCCAATTACCCCTCTCCTTTGCCCAGTCGCGACT
NO. 34        CTGGTTCTTGTATCAATTAGAAGGAGCCACGGGAACCTATAACA
C2            TGACAGGGGCCTTGAGTTTAAGCGGGCCTCTTCAGGTCGAAGCC
nucl          CTCAAACAAGCCCTAAGAACTATCATTCAACGCCATGAGCCATT
acid          GCGTACCAGTTTCCAATCGGTTGACGGGGTTCCAGTGCAGGTGA
              TTAATCCCTATCTGTTTGGGAATTAGCGATGGTTGATTTGACA
              GGAAAGGAGACAGAAGCAGAAAAATTGGCCTATCAG
              GAATCCCAAACCCCGTTTGATTTGACCAATAGTCCTTTGTTGAG
              GGTAACGCTCCTCAAATTACAGCCAGAAAAGCATATTTTATTAA
              TTAATATGCACCATATTATTTCCGATGGCTGGTCAATCGGTGTT
              TTTGTTCGTGAATTGTCCCATCTCTATAGGGCTTTTGTGGCGGG
              TAAAGAACCAACTTTACCGATTTTACCAATTCAGTATGCGGATT
              TTGCCGTTTGGCAGCGAGAGTGGTTACAGGGTAAGGTTTTAGCG
              GCTCAATTGGAATATTGGAAGCGACAATTGGCAGATGCTCCTCC
              TCTGCTGGAACTGCCCACTGATCGCCCTCGTCCCGCAATCCAAA
              CCTTTCAAGGCAAGACAGAAAGATTTGAGCTAGATAGGAAACTG
              ACCCAAGAATTAAAGGCATTAAGT
              CAACAGTCGGGTTGTACTTTATTTATGACTTTGTTGGCCGCTTT
              TGGGGTGGTTTTATCCCGTTATAGTGGCCAGACTGATATCGTCA
              TTGGTTCGGCGATCGCCAACCGTAATCGCCAAGCATTGAGGGG
              TTAATTGGCTTTTTTGTTAACACTTTGGCGTTGAGGTTAGATTT
              ATCA SEQ ID        ACCTATGGAGAATTAAACCATCGCGCCAATCAATTAGCTCACTA
NO. 35        TCTTCAGTCGTTAGGAGTCACCAAAGAACAAATCGTCGGGGTTT
A2            ATCTGGAACGTTCCCTTGAAATGGCGATCGGATTTTTAGGTATT
nucl          CTCAAAGCAGGAGCCGCCTATCTCCCCATTGATCCTGAATATCC
acid          CTCAGTACGCACCCAATTTATTCTCGAAGATACCCAACTTTCGC
              TTCTCTTAACTCAGGCAGAACTGGCAGAAAAACTGCCCCAGACT
              CAAAACAAAATTATCTGTCTAGATCGGGACTGGCCA
              GAAATTACCTCCCAACCCCAGACAAACCTAGACCTAAAGATAGA
              ACCTAATAACCTAGCC
              TATTGCATCTATACTTCTGGTTCCACAGGACAACCCAAAGGAGT
              ACTGATTTCCCATCAAGCCCTACTCAACTTAATTTTCTGGCATC
              AACAAGCGTTTGAGATTGGCCCCTTACATAAAGCGACCCAAGTG
              GCAGGCATTGCTTTCGATGCAACGGTTTGGGAATTGTGGCCCTA
              TCTGACCACAGGAGCCTGTATTAATCTGGTTCCCCAAAATATTC
              TGCTCTCACCGACGATTTACGGATTTGGTTGCTTAACCGAGAA
              ATTACCATGAGTTTTGTGCCAACTCCTTTAGCTGAAAAATTATT
              ATCCTTGGATTGGCCTAACCATTCTTGTCTAAAAACCCTGTTAC
              TGGGAGGTGACAAACTTCATTTTTATCCTGCTGCGTCCCTTCCC
              TTTCAGTCATTAACAACTATGGCCCAACGGAAAATACAGTGGT
              TGCGACCTCTGGACTGGTCAAATCATCTTCATCTCATCACTTTG
              GAACTCCGACTATTGGTCGTCCCATTGCCAACGTCCAAATCTAT
              TTATTAGACCAAAACCTACAACCTGTCCCCATTGGTGTACCAGG
              AGAATTACATTTAGGTGGGCGGGTTTAGCGCAGGGCTATCTCA
              ATCGTCCTGAGTTAACGCTGAAAAATTTATTGCCAATCCCTTT
              GATCCCCCCCTAACCCCCCTTGATAAGGGGGGAGAAGAACCCTC
              AAAACTCTATAAAACG
              GGAGACTTAGCCCGTTATTTACCCGATGGCAATGTAGAATTTTT
              GGGACGTATTGACAATCAGGTAAAATTCGGGTTTCGCATCG
              AAACTGGGGAAATCGAAGCCGTTTTAAGTCAATATTTCCTATTA
              GCTGAAAGTGTAGTC SEQ ID        GCTCAACTGACTCAAATTTGGAGTGAAGTTTTGGGACTGGAACG
NO. 36        CATTGGCGTTAAGGACAACTTTTTTGAATTGGGAGGACATTCTC
T2            TTTTGGCTACCCAGGTTTTATCAAGAATTAATTCAGCCTTTGGA
nucl          CTTGATCTTTCTGTGCAAATTATGTTTGAATCACCAACGATCGC
acid          GGGCATTGCGGGTTATATT SEQ ID        GCTAGAGACGGTCATTTACCCCTGTCTTTTGCTCAACAACGTTT
NO. 37        ATGGTTTTTACATTATCTTTCCCCTGATAGTCGTTCCTACAATA
C3            CCCTGGAAATATTGCAAATTGATGGGAATCTCAATCTGACTGTG
nucl          CTAGAGCAGAGTTTGGGGAATTAATTAACCGCCATGAAATTTT
acid          TAGAGCAACATTCCCACTGTTTCAGGGGAACCGATTCAGAAAA
              TTGCACTTCCTAGTCGTTTTCAGTTAAAAGTTGATAATTATCAA
              GATTTAGACGAAAATGAACATCAGCTAAAATTCAACAAGTAGC
              AGAATTGGAAGCAGGACAAGCTTTTGATTTAACGGTGGGGCCAC
              TGATTCAGTTTAAGCTATTGCAATTGAGTCCCCAGAAGTCGGTG
              CTGCTGTTGAAAATGCACCATATTATCTATGATGGCTGGTCTTT
              TGGGATTCTGATTCGGGAATTATCGGCTCTATACGAAGCATTTT
              TAAAGAACTTAGCCAATCCTCTCCCTGCGTTGTCTATTCAGTAT
```

TABLE 1-continued

```
GCAGATTTTGCGGTTTGGCAACGTCAATATCTCTCAGGTGAGGT
CTTAGATAAACAACTCAATTATTGGCAAGAACAGTTAGCAACAG
TCTCTCCTGTTCTTACTTTACCAACGGATAGACCCCGTCCGGCG
ATACAAACTTTTCAGGGAGGAGTTGAGCGTTTTCAACTGGATCA
AAATGTCACTCAAGGTCTTAAAAAGTTAGGTCAAGATCAGGTTG
CAACCCTGTTTATGACGTTGTTGGCCGGTTTCGGCGTTTTGCTA
TCTCGTTATAGTGGTCAATCTGATCTGATGGTGGGTTCTCCGAT
CGCTAATCGTAATCAAGCAGCGATCGAACCTTTAATTGGCTTTT
TTGCTAACACTTTGGCTTTAAGAATTAATTTATCA
```

SEQ ID NO. 38 A3 nucl acid
```
ACATACACTGAATTAAACCATCGCGCTAATCAGTTAGCCCATTA
TTTACAAACTTTAGGCGTGGGAGCAGAAGTCTTAGTCGGTATTT
CCCTAGAACGTTCTTTAGAGATGATTATCGGCTTATTAGGGATT
CTCAAGGTAGGTGGTGCTTATCTTCCTCTTGATCCAGACTATCC
CACTGAGCGTCTTCAGTTGATGTTAGAAGACAGTCAAGTTCCTT
TTTTGATTACCCACAGTTCTTTATTAGCAAAATTGCCTCCCTCT
CAAGCAACTCTGATTTGTTTAGATCATATCCAAGAGCAGATTTC
TCAATATTCTCCAGATAATCTTCAATGTCAGTTAACTCCTGCCA
ATTTAGCTAACGTTATTTATACCTCTGGCTCTACGGGTAAGCCT
AAAGGGGTGATGGTTGAACATAAAGGTTTAGTTAACTTAGCTCT
TGCTCAAATTCAATCTTTTGCAGTCAACCATAACAGTCGTGTGC
TGCATTTGCTTCTTTTAGTTTTGATGCTTGTATTTCAGAAATTT
TTGATGACCTTTGGTTCTGGAGCGACGCTTTATCTTGCACAAAA
AGATGCTTTATTGCCAGGTCAGCCATTAATTGAACGGTTAGTAA
AGAATGAATTACTCATGTGACTTTGCCGCCTTCAGCTTTAGTG
GTTTTACCCCAGGAACCGTTACGCAACTTAGAAACCTTAATTGT
GGCGGGTGAGGCTTGTTCTCTTGATTTAGTGAAACAATGGTCAA
TCGATAGAAACTTTTTCAATGCCTATGGGCCAACGGAAGCGAGT
GTTTGTGCCACTATTGGACAATGTTATCAAGATGATTTAAAGGT
GACGATTGGTAAGGCGATCGCCAATGTCCAAATTTATATTTTAG
ATGCCTTTTACAGCCGGTGCCGTGGGAGTGTCAGGAGAGTTA
TACATTGGTGGAGTTGGGGTGGCAAGGGGCTATTTAAATCGTCC
TGAATTAACCCAAGAAAAATTTATTGCTAATCCTTTTAGTAACG
ACCCAGATTCTCGGCTCTATAAAACTGGCGACTTAGCGCGTTAT
TTACCCGATGGTAATATTGAATATTTAGGACGCATTGACAATCA
GGTAAAAATTCGCGGTTTTCGCATTGAGTTAGGAGAAATTGAAG
CGGTTCTGAGTCAATGTCCCGATGTGCAAAATACGGCGGTG
```

SEQ ID NO. 39 T3 nucl acid
```
GAAATTCTGGCTCAAATATGGGGGCAAGTTCTCAAGATAGAAAG
AGTCAGCAGAGAAGAT
AATTTCTTTGAATTGGGGGGGCATTCCCTTTTAGCTACCCAGGT
AATGTCCCGTCTGCGTGAAACTTTTCAAGTCGAATTACCTTTGC
GTAGTCTCTTTACCGCTCCCACTATTGCTGAATTGGCCCTAACA
ATT
```

SEQ ID NO. 40 C4 nucl acid
```
AACGACAGTGCTAACCTCCCGTTATCTTTTGCTCAACAACGTTT
ATGGTTTCTGGATCAATTAGAACCTAACAGCGCCTTTTATCATG
TAGGGGGAGCCGTAAGACTAGAAGGAACATTAAATATTACTGCC
TTAGAGCAAAGCTTAAAAGAAATTATTAATCGTCATGAAGCTTT
ACGCACAAATTTATAACGATTGATGGTCAAGCACTCAAATTA
TTCACCCTACTATTAATTGGCGATTGTCTGTTGTTGATTGTCAA
AATTTAACCGACACTCAATCTCTGGAAATTGCGGAAGCTGAAAA
GCCCTTTAATCTTGCTCAAGATTGCTTATTTCGTGCTACTTTAT
TCGTCGATCACCGCTAGAATATCATCTACTCGTGACCATGCAC
CATATTGTTAGCGATGGCTGGTCAATTGGAGTATTTTTTCAAGA
ACTAACTCATCTTTACGCTGTCTATAATCAGGGTTTACCCTCAT
CTTTAACGCCTATTAAAATACAATATGCTGATTTTGCGGTCTGG
CAACGGATATTGGTTACAAGGTGAAATTTTAAGTAACTCAATTGAA
TTATTGGCGCGAACAATTAGCAAATGCTCCTGCTTTTTTACCTT
TACCGACAGATAGACCTAGGCCCGCAATCCAAACTTTTATTGGT
TCTCATCAAGAATTTAAACTTTCTCAGCCATTAAGCCAAAAATT
GAATCAACTAAGTCAGAAGCATGGAGTGAGTCATTTATGACTC
TCCTGGCTGCTTTTGCTACCTTACTTTACCGTTATACAGGACAA
GCAGATATTTAGTTGGTTCTCCTATTGCTAACCGTAATCGTAA
GGAAATTGAGGGATTAATCGGCTTTTTTGTTAATACATTAGTTC
TGAGATTGAGTTTAGAT
```

SEQ ID NO. 41 A4 nucl acid
```
ACCTATGCTGAATTAAATCATCAAGCTAATCAGTTAGTCCATTA
CTTACAAACTTTAGGAATTGGGCCAGAGGTCTTAGTCGCTATTT
CAGTAGAACGTTCTTTAGAAATGATTATCGGCTTATTAGCACTT
CTCAAGGCGTGTGGTGCTTATCTCCCTCTTGCTCCTGACTATCC
CACTGAGCGTCTTCAGTTCATGTTAGAAGATAGTCAAGCTTCTT
TTTTGATTACCCACAGTTCTTTATTAGAAAAATTGCCTTCTTCT
CAAGCGACTCTGATTTGTTTAGATCACATCCAAGAGCAGATTTT
TCAATATTCTCCCGATAATCTTCAAGTGAGTTAACTCCTCCA
ATTTGGCTAACGTTATTTACACCTCTGGCTCTACGGGTAAGCCT
AAAGGGGTGATGGTTGAACATCGGGCTTAGTTAACTTAGCGAG
TTCTCAAATTCAATCTTTTGCAGTCAAAAATACAGTCGTGTAC
TGCATTTGCTTCTTTTAGTTTTGATGCTTGTATTTCAGAAATTT
```

TABLE 1-continued

```
TTGATGACCTTTGGTTCTGGAGCGACTCTTTATCTTGCTCAAAA
AAATGATTTATTGCCAGGTCAGCCATTAATGGAAAGGTTAGAAA
AGAATAAAATTACCCATGTTACTTTACCCCCTTCAGCTTTAGCT
GTTTTACCAAAAAACCGTTACCCAACTTACAAACTTTAATTGT
GGCGGGTGAGGCTTGTCCTCTGGATTTAGTCAAACAATGGTCAG
TCGGTAGAAACTTTTTCAATGCCTATGGCCCGACAGAAACGAGT
GTTTGTGCCACGATTGGACAATGTTATCAAGATGATTTAAAGGT
CACGATTGGTAAGGCGATCGCTAATGTCCAAATTTATATTTTGG
ATGCCTTTTACAACCAGTACCCATCGGAGTACCAGGGGAATTA
TACATTGGTGGAGTCGGAGTTGCGAGGGGTTATCTAAATCGTCC
TGAATTAACGGCGGAAAGATTTATTCCTAATCCTTTTGATCCCC
CCCTAACCCCCCTTAAAAAGGGGGGAGGATAAGAGCTATGAAACT
TTTAAAAAGGGGGAAGAGCAACCA
TCAAAACTCTATAAAACGGGAGATTTAGCTCGTTATTTACCCGA
TGGCAATATTGAATATTTAGGACGCATTGACAATCAGGTAAAAA
TTCGCGGTTTTCGCATTGAGTTAGGAGAAATTGAAGCGGTTCTG
AGTCAATGTCCCGATGTGCAAAATACGGCGGTG
```

SEQ ID NO. 42 T4 nucl acid
```
TTACAATTAGCTCAAATCTGGTCAGAGATTTTAGGCATTAATAA
TATTGGTATTCAGGAAAACTTCTTTGAATTAGGCGGTCATTCTT
TATTAGCAGTCAGTCTGATCAATCGTATTGAACAAAAGTTAGAT
AAACGTTTACCATTAACCAGTCTTTTTCAAAATGGAACCATAGC
AAGTCTAGCTCAATTACTAG
```

SEQ ID NO. 43 TE nucl acid
```
ACTCCATTTTTGCTGTTCATCCCATTGGTGGTAATGTGCTATG
TTATGCCGATTTAGCTCGTAATTTAGGAACGAAACAGCCGTTTT
ATGGATTACAATCATTAGGGCTAAGTGAATTAGAAAAAACTGTA
GCCTCTATTGAAGAAATGGCGATGATTTATATTGAAGCAATACA
AACTGTTCAAGCCTCTGGTCCCTACTATTTAGGAGGTTGGTCAA
TGGGAGGAGTGATAGCTTTTGAAATCGCCCAACAATTATTGACC
CAAGGTCAAGAAGTTGCTTTACTGGCTTTAATAGATAGTTATTC
TCCCAGTTTACTTAATTCAGTTAATAGGGAGAAAAATTCTGCTA
ATTCCCTGACAGAAGAATTTAATGAAGATATCAATATTGCCTAT
TCTTTTCATCAGAGATTAGCAAGTATATTTAATCAAGAAATCTC
TTTCTCTGGGAGTGAACTTGCTCATTTTACATCAGACGAATTAC
TAGACAAGTTTATTACTTGGAGTCAAGAGACGAATCTTTTCCGG
TCAGATTTTGGGAAGCAGCAGGTTAAAAACCTGGTTTAAAGTTTT
CCAGATTAATCACCAAGCTTTGAGCAGCTATTCTCCCAAGACGT
ATCTGGGTAGAAGTGTTTTCTTAGGAGCGGAAGACAGTTCATTT
AAAAATCCTGGTTGGCATCAA
```

SEQ ID NO. 44 MO nucl acid
```
AGCGGGTCTCAAGACCAAAAAACGATACAGTTTAGCCTCTACTA
CTTTGGTAGCTATGAAGCGGAATTTAACCCGAATAAATATAACT
TACTGTTTGAAGGAGCTAAATTTGGCGATCGCGCTGGTTTTACG
GCCCTTTGGATTCCTGAACGTCATTTCCACGCTTTTGTGGTTTT
TTCTCCCAATCCTTCGGTTTTGGCGGCGGCTTTAGCACGGGAAA
CCAAACAGATTCAACTGCGATCAGGCAGTGTGGTTTTACCGCTA
CATAATTCCATCCGAGTCGCCGAAGAATGGGCAGTGGTGGACAA
TCTTTCCAGGGCCGCTTGGTATTGCTTTTGCATCGGGTTGGC
ATCCCCAGGATTTTGTCTTGGCTCCCCAGTCCTTTGGCCAACAT
CGGGAATTGATGTTCCAAGAAATTGAAACCGTCCAGAAACTTTG
GCGAGGGGAAGCGATCACCGTGCCAGACGAAAGGGTCAA
AGGGTAGAGGTTAAAACCTATCCCCAACCGATGCAGTCCCAGTT
ACCCAGCTGGATTACTATTGTCAATAATCCCGATACCTATATCA
GAGCAGGGGGCGATCGGTGCTAATATCCTTACCAATCTGATGGG
CAAAGCGTGGAAGATTTAGCCCGTAATATTGCGCTATATCGTCA
ATCTTTGGCAGAGCATGGTTATGATCCCGCGTCGGGAACGGTGA
CAGTTCTCCTGCATCATTTTGTTGGCAAGGATTTAGAACAAGTT
CGAGAACAGGCTCGCCAACCCTTTGGGCAATACCTCACCTCCTC
TGTCGGACTCTTGCAGAACATGGTCAAGAGCCAGGGCATGAAAG
TGGATTTTGAACAATTAAGAGACGAAGATCGGGACTTTCTCCTC
GCTTCTGCCTATAAACGCTATACAGAAACCAGTGCTTTAATTGG
CACACCCGAATCCTGTCGTCAAATTATTGATCATTTGCAGTCCA
TCGGTGTGGATGAAGTGGCTTGTTTATTGATTTGGGGTAGAT
GAACAAACAGTTTTGGCCAATTTACCCTATCTCCAGTCCCTAAA
AGACTTATATCAA
```

SEQ ID NO. 45 SP 1 nucl acid
```
ATTGATCCCCCCTAACCCCCCTTGATAAGGGGATTGATCCCCC
CCTAACCCCCCTTGATAAGGGGATTGATCCCCCCCTAACCCCCC
TTGATAAGGGG
```

SEQ ID NO. 46 SP 2 nucl acid
```
CCTTATCAAGGGGGGTTAGGGGGGGATCAATCCCCTTATCAAGG
GGGGTTAGGGGGGAT
CAATCCCCTTATCAAGGGGGGTTAGGGGTGATCAATCCCCTTA
TCAAGGGGGTTAGGGGGTGATCAATCCCCTTATCAAGGGGGGT
TAGGGGGGGATCAATCCCCTTATCAAGGGGGGTTAGGGGGGGA
```

TABLE 1-continued

TCAAGTC

SEQ ID NO. 47
MT nucl acid

CCTGCTTCAGAAATGCGAGAGTGGGTCGAAAACACTGTTAGTCG
CATCTTGGCTTTCCAACCAGAACGCGGTTTAGAAATTGGTTGTG
GTACAGGTTTGTTACTCTCCAGGGTAGCAAAGCATTGTCTTGAA
TATTGGGCAACGGATTATTCCCAAGGGGCGATCCAGTATGTTGA
ACGGGTTTGCAATGCCGTTGAAGGTTTAGAACAGGTTAAATTAC
GCTGTCAAATGGCAGATAATTTTGAAGGTATTGCCCTACATCAA
TTTGATACCGTCGTCTTAAATTCGATTATTCAGTATTTTCCCAG
TGTGGATTATCTGTTACAGGTGCTTGAAGGGGCGATCAACGTCA
TTGGCGAGCGAGGTCAGATTTTGTCGGGGATGTGCGGAGTTTA
CCCCTATTAGAGCCATATCATGCGGCTGTGCAATTAGCCCAAGC
TTCTGACTCGAAAACTGTTGAACATGGCAACAACAGGTGCGTC
AAAGTGTAGCAGGTGAAGAAGAACTGGTCATTGATCCCACATTG
TTCCTGGCTTTAAAACAACATTTTCCGCAAATTAGCTGGGTAGA
AATTCAACCGAAACGGGGTGTGGCTCACAATGAGTTAACTCAAT
TTCGCTATGATGTCACTCTCCATTTAGAGACTATCAATAATCAA
GCATTATTGAGCGGCAATCCAACGGTAATTACCTGGTTAAATTG
GCAACTTGACCAACTGTCTTTAACACAAATTAAAGATAAATTAT
TAACAGACAAACCTGAATTGTGGGGAATTCGTGGTATTCCTAAT
CAGCGAGTTGAAGAGGCTCTAAAAATTTGGGAATGGGTGGAAAA
TGCCCCTGATGTTGAAACGGTTGAACAACTCAAAAAACTTCTCA
ACAACAAGTAGATACTGGTATTAATCCTGAACAGGTTTGGCAA
TTAGCTGAGTCTCTCGGTTACACCGCTCACCTTAGTTGGTGGGA
AAGTAGTCAAGACGGTTCCTTACGTACTGGGGGAATTTAAGAGTC
CAGAAGCGGAGGACTCAAAAAAATTAACCCTTTCAAACTTGCT
TTCTGGGATGAAAAACCCTTTAAAATAAAGCCCTGGAGTGACTA
TACTAACAACCCCTCTGCGCGGTAAGTTAGTCCAAAAATTAATTC
CT

SEQ ID NO. 48
MT 2 nucl acid

ATGACAAATTATGGCAAATCTATGTCTCATTACTATGATCTAGT
GGTAGGACATAAAGGTTATAACAAAGATTACGCCACTGAAGTAG
AATTCATTCACAATTTAGTTGAGACTTACACAACTGAAGCCAAA
TCTATCCTATACTTGGGCTGTGGTACGGGTTATCATGCCGCTCT
TTTTAGCACAGAAAGGGTATTCTGTACATGGTGTTGATCTCAGTG
CTGAAATGTTAGAGCAGGCTAAAACTCGCATTGAAGATGAAACA
ATAGCTTCTAATCTGAGTTTTTCTCAAGGAAATATTTGTGAAAT
CCGTTTAAATCGTCAGTTTAATGTTGTTCTTGCTCTATTTCATG
TGGTTAACTATCAAACGACCAATCAAAATTTACTGGCAACGTTT
GCAACGGTTAAAAACCATTTAAAAGCTGGGGGGATTTTTATTTG
TGATGTGTCCTATGGGTCTTACGTACTGGGGGAATTTAAGAGTC
GGCCTACGGCATCAATATTGCGTTTAGAGGATAATTCCAATGGT
AACGAAGTAACCTATATTAGTGAACTAAATTTTTTAACCCATGA
AAATATAGTGGAAGTTACTCACAATTTATGGGTAACAAATCAAG
AAAATCAACTTCTAGAGAATTCACGGGAAACACATCTTCAGCGC
TATCTTTTCAAGCCTGAAGTTGAATTGTTGGCTGATCGTTGTGA
ACTAACTGTTCTTGATGCGATGCCCTGGCTTGAACAACGTCCTT
TGACAAACATTCCTTGTCCTTCAGTTTGTTTTGTTATTGGGCAT
AAAACAACCCATTCAGCTTAA

SEQ ID NO. 49 Primer A

CCGACCTGTGATAAACAATTC

SEQ ID NO. 50 Primer B

CKNCCDGTDATRAANARYTC

SEQ ID NO. 51 Primer C

TTCAATATCCTGGGGATA

SEQ ID NO. 52 Primer D

YTCDATRTCYTGNGGRTA

SEQ ID NO. 53 Primer E

CGTTGGTTACAGGCCCTTTCT

SEQ ID NO. 54 Primer F

MGNTGGYTNCARGCNYTNWS

SEQ ID NO. 55 Primer G

TTAGACTTAAGCCATTGG

SEQ ID NO. 56 Primer H

YTNGAYYTNWSNCAYTGG

SEQ ID NO. 57 Primer I

CATAGAAGAATCGAGACCATATTC

SEQ ID NO. 58 Primer J

CATNSWNSWRTCNARNCCRTAYTC

SEQ ID NO. 59 ABC Transporter

MTTQTASSANALASFNQFLRDVKAIAQPYWYPTVSNKRSFSEVI
RSWGMLSLLIFLIVGLVAVTAFNSFVNRRLIDVIIQEKDASQFA
STLTVYAIGLICVTLLAGFTKDIRKKIALDWYQWLNTQIVEKYF
SNRAYYKINFQSDIDNPDQRLAQEIEPIATNAISFSATFLEKSL
EMLTFLVVVWSISRQIAIPLMFYTIIGNFIAAYLNQELSKINQA
QLQSKADYNYALTHVRTHAESIAFFRGEKEEQNIIQRRFQEVIN
DTKNKINWEKGNEIFSRGYRSVIQFFPPFLVLGPLYIKGEIDYGQ
VEQASLASFMPASALGELITEFGTSGRFSSYVERLNEFSNALET
VTKQAENVSTITTIEENHFAFEHVTLETPDYEKVIVEDLSLTVQ
KGEGLLIVGPSGRGKSSLLRAIAGLWNAGTGRLVRPPLEEILFL
PQRPYIILGTLREQLLYPLTNSEMSNTELQAVLQQVNLQVNLNR
VDDFDSEKPWENILSLGEQQRLAFARLLVNSPSFTILDEATSAL
DLTNEGILYEQLQTRKTTFISVGHRESLFNYHQWVLELSADSSW
ELLSVQDYRLKKAGEMFTNASSNNSITPDITIDNGSEPEIVYSL
EGFSHQEMKLLTDLSLSSIRSKASRGKVITAKDGFTYLYDKNPQ
ILKWLR

SEQ ID NO. 60 ABC Transporter Nucl acid

ATGCAACCCAAACAGCTTCTAGTGCCAATGCCCTTGCTTCCTT
TAACCAATTTTTAAGGGATGTAAAGGCGATCGCCAACCCTATT
GGTATCCCACTGTATCAAATAAAAGAAGCTTTTCTGAGGTTATT
CGTTCCTGGGGAATGCTATCACTGCTTATCTTTTGATTGTGGG
ATTAGTCGCCGTCACGGCTTTTAATAGTTTTGTTAATCGTCGTT
TAATTGATGTCATTATTCAAGAAAAAGATGCGTCTCAATTTGCC
AGTACATTAACTGTCTATGCGATCGGATTAATCTGTGTAACGCT
GCTGGCAGGGTTCACTAAAGATATTCGCAAAAAATTGCCCTAG
ATTGGTATCAATGGTTAAACACCCAGATTGTAGAGAAATATTTT
AGTAATCGTGCCTATTATAAAATTAACTTTCAATCTGACATTGA
TAACCCCGATCAACGTCTAGCCCAGGAAATTGAACCGATCGCCA
CAAACGCCATTAGTTTCTCGGCCACTTTTTTGGAAAAAGTTTG
GAAATGCTAACTTTTTTAGTGGTAGTTTGGTCAATTTCTCGACA
GATTGCTATTCCGCTAATGTTTTACACGATTATCGGTAATTTTA
TTGCCGCCTATCTAAATCAAGAATTAAGCAAGATCAATCAGGCA
CAACTGCAATCAAAAGCAGATTATAACTATGCCTTAACCCATGT
TCGGACTCATGCGGAATCTATTGCTTTTTTCGGGGAGAAAAG
AGGAACAAAATATTATTCAGCGACGTTTTCAGGAAGTTATCAAT
GATACGAAAAATAAAATTAACTGGGAAAAAGGGAATGAAATTTT
TAGT
CGGGGCTATCGTTCCGTCATTCAGTTTTTTCCTTTTTAGTCCT
TGGCCCTTTGTATATTAAAGGAGAAATTGATTATGGACAAGTTG
AGCAAGCTTCATTAGCTAGTTTTATGTTTGCATCGGCCCTGGGA
GAATTAATTACAGAATTTGGTACTTCAGGACGTTTTTCTAGTTA
TGTAGAACGTTTAAATGAATTTTCTAATGCCTTAGAAACTGTGA
CTAAACAAGCCGAGAATGTCAGCACAATTACAACCATAGAAGAA
AATCATTTTGCCTTTGAACACGTCACCCTAGAAACCCCTGACTA
TGAAAAGGTGATTGTTGAGGATTTATCTCTTACTGTTCAAAAAG
GTGAAGGATTATTGATTGTCGGGCCCAGTGGTCGAGGTAAAAGT
TCTTTATTAAGGGCGATCGCCGGTTTATGGAATGCTGGCACTGG
GCGTTTAGTGCGTCCTCCCCTAGAAGAAATTCTCTTTTTGCCCC
AACGTCCCTACATTATTTGGGAACCTTACGCGAACAATTGCTG
TATCCTCTAACCAATAGTGAGATGAGCAATACCGAACTTCAAGC
AGTATTACAACAAGTCAATTTGCAAAATGTGCTAAATCGGGTGG
ATGACTTTGACTCCGAAAAACCCTGGGAAAACATTCTCTCCCTC
GGTGAACAACAACGCCTAGCCTTTGCTCGATTGTTAGTGAATTC

TABLE 1-continued

```
TCCGAGTTTTACCATTTTAGATGAGGCGACCAGTGCCTTAGATT
TAACAAATGAGGGGATTTTATACGAGCAATTACAAACTCGCAAG
ACAACCTTTATTAGTGTGGGTCATCGAGAAAGTTTGTTTAATTA
CCATCAATGGGTTTTAGAACTTTCTGCTGACTCTAGTTGGGAAC
TCTTAAGCGTTCAAGATTATCGCCTTAAAAAAGCGGGAGAAATG
TTTACTAATGCTTCGAGTAACAATTCCATAACACCCGATATTAC
TATCGATAATGGATCAGAACCAGAAATAGTCTATTCTCTTGAAG
GATTTTCCCATCAGGAAATGAAACTATTAACAGACCTATCACTC
TCTAGCATTCGGAGTAAAGCCAGTCGAGGGAAGGTGATTACAGC
CAAGGATGGTTTTACCTACCTTTATGACAAAAATCCTCAGATAT
TAAAGTGGCTCAGAACTTAA
```

In one embodiment the entire gene cluster is transformed and expressed in a heterologous system. SEQ ID NO. 61 encompasses the genes of said cluster.

```
1-27260       ATGACTATTAACTATGGTGATCTGCAAGAACCCTTTA
Microginin-   ATAAATTCTCAACCCTAGTTGAATTACTCCGTTATCG
Cluster       GGCAAGCAGTCAACCGGAACGCCTCGCCTATATTTTT
1-1743        CTGCGAGACGGAGAAATCGAAGAAGCTCGTTTAACCT
Adenylation-  ATGGGGAACTGGATCAAAAGGCTAGGGCGATCGCCGC
Protein (A*)  TTATCTACAATCCTTAGAAGCCGAGGGCGAAAGGGGT
1892-2158     TTACTGCTCTATCCCCCAGGACTAGATTTTATTTCAG
Acyl-Carrier- CTTTTTTTGGTTGTTTATATGCGGGAGTCGTTGCCAT
Protein (ACP) TCCCGCCTATCCACCCCGACGGAATCAAAACCTTTTG
2204-3016     CGTTTACAGGCGATTATTGCCGATTCTCAAGCCCGAT
Methyltrans-  TTACCTTCACCAATGCCGCTCTATTTCCCAGTTTAAA
ferase (MT)   AAACCAATGGGCTAAAGACCCTGAATTAGGAGCAATG
3464-13123    GAATGGATTGTTACCGATGAAATTGACCATCACCTCA
PKS/NRPS (KS- GGGAGGATTGGCTAGAACCAACCCTCGAAAAAAACAG
AT-ACP-AMT-   TCTCGCTTTTCTACAATACACCTCTGGTTCAACGGGA
MO-C-A-T)     ACTCCAAAGGGAGTAATGGTCAGTCACCATAATTTGT
13120-17832   TGATTAATTCAGCCGATTTAGATCGTGGTTGGGGCCA
NRPS 2 (C-A-  TGATCAAGATAGCGTAATGGTCACTTGGCTACCGACC
Mt-T)         TTCCATGATATGGGTCTGATTTATGGGGTTATTCAGC
17836-25194   CTTTGTACAAAGGATTTCTTTGTTACATGATGTCCCC
NRPS 3 (C-A-  TGCCAGCTTTATGGAACGACCGTTACGTTGGTTACAG
T-C-A-T)      GCCCTTTCTGATAAAAAAGCAACCCATAGTGCGGCCC
25257-27260   CCAACTTTGCCTACGATCTTTGTGTGCGGAAAATTCC
ABC-          CCCTGAAAACGGGCTACGTTAGACTTAAGCCATTGG
Transporter   TGCATGGCCTTAAATGGGGCCGAACCCGTCAGAGCGG
(ABC)         AGGTACTTAAAAAGTTTGCGGAGGCTTTTCAAGTTTC
              TGGTTTCAAAGCCACAGCCCTTTGTCCTGGCTACGGT
              TTAGCAGAAGCCACCCTGAAAGTTACGGCGGTTAGTT
              ATGACAGTCCCCCTTACTTTTATCCCGTTCAGGCTAA
              TGCTTTAGAAAAAAATAAGATTGTGGGAGCCACTGAA
```

```
ACCGATACCAATGTGCAGACCCTCGTGGGCTGCGGCT
GGACAACGATTGATACTCAAATCGTCATTGTCAATCC
TGAAACCCTGAAACCTTGCTCCCCTGAAATTGTCGGC
GAAATTTGGGTATCAGGTTCAACAATCGCCCAAGGCT
ATTGGGGAAAACCTCAAGAGACTCAGGAAACCTTTCA
AGCTTATTTGGCAGATACAGGAGCCGGGCCTTTTCTG
CGAACAGGAGACTTGGGCTTCATTAAAGATGGTGAAT
TGTTTATCACAGGTCGGCTCAAGGAAATTATTCTGAT
TCGAGGACGCAATAATTATCCCCAGGATATTGAATTA
ACCGTCCAAAATAGTCATCCCGCTCTGCGTCCCAGTT
GTGGGGCTGCTTTTACCGTTGAAAATAAGGGCGAAGA
AAAGCTCGTGGTCGTTCAGGAAGTGGAGCGCACCTGG
CTCCGTAAGGTAGATATAGATGAGGTAAAAAGAGCCA
TTCGTAAAGCTGTTGTCCAGGAATATGATTTACAGGT
TTATGCGATCGCGCTGATCAGGACTGGCAGTTTACCA
AAAACCTCTAGCGGTAAAATTCAGCGTCGTAGCTGTC
GGGCCAAATTTTTAGAGGGAAGCCTGGAAATTTTGGG
CTAAGAAAATTTCTCGATCGGCACTTAATGTGTTAAA
TTCGTATGTCGATTGAAACTTCGACCAATTCTTTCTC
TCCCCTTAAGTCCATGTCTCTGGATTTGAAAATTCCT
TAAACTTTAACTACATTTCTCAAGAAAGCAAATTGAA
TCTAATGTCCACAGAAATCCCAAACGACAAAAAACAA
CCGACCCTAACGAAAATTCAAAACTGGTTAGTGGCTT
ACATGACAGAGATGATGGAAGTGGACGAAGATGAGAT
TGATCTGAGCGTTCCCTTTGATGAATATGGTCTCGAT
TCTTCTATGGCAGTTGCTTTGATCGCTGATCTAGAGG
ATTGGTTACGACGAGATTTACATCGCACCCTGATCTA
CGATTATCCAACTCTAGAAAAGTTGGCTAAACAGGTT
AGTGAACCCTGACATTTTTATAAAGTTTGTGCTTAAA
AATTTTGAGGAAGTTCTAAAATGACAAATTATGGCAA
ATCTATGTCTCATTACTATGATCTAGTGGTAGGACAT
AAAGGTTATAACAAAGATTACGCCACTGAAGTAGAAT
TCATTCACAATTTAGTTGAGACTTACACAACTGAAGC
CAAATCTATCCTATACTTGGGCTGTGGTACGGGTTAT
CATGCCGCTCTTTTAGCACAGAAAGGGTATTCTGTAC
ATGGTGTTGATCTCAGTGCTGAAATGTTAGAGCAGGC
TAAAACTCGCATTGAAGATGAAACAATAGCTTCTAAT
CTGAGTTTTTCTCAAGGAAATATTTGTGAAATCCGTT
TAAATCGTCAGTTTAATGTTGTTCTTGCTCTATTTCA
TGTGGTTAACTATCAAACGACCAATCAAAATTTACTG
```

-continued

GCAACGTTTGCAACGGTTAAAAACCATTTAAAAGCTG
GGGGGATTTTTATTTGTGATGTGTCCTATGGGTCTTA
CGTACTGGGGGAATTTAAGAGTCGGCCTACGGCATCA
ATATTGCGTTTAGAGGATAATTCCAATGGTAACGAAG
TAACCTATATTAGTGAACTAAATTTTTTAACCCATGA
AAATATAGTGGAAGTTACTCACAATTTATGGGTAACA
AATCAAGAAAATCAACTTCTAGAGAATTCACGGGAAA
CACATCTTCAGCGCTATCTTTTCAAGCCTGAAGTTGA
ATTGTTGGCTGATGCTTGTGAACTAACTGTTCTTGAT
GCGATGCCCTGGCTTGAACAACGTCCTTTGACAAACA
TTCCTTGTCCTTCAGTTTGTTTTGTTATTGGGCATAA
AACAACCCATTCAGCTTAAATTCTGCTAAAAAAAATC
CAACTTACCTTATTCTCTGAAACCACACAAGCCATGA
ATACAATTCAAGATGCCAAGACCGAAAATTACTCAAT
CTTAAATCAGTCAATTCCAAGACCTCTCAAACTGAGT
AATATCCTATTACGATAAGATTTTGCGTTCTCCTTTG
TTTGGAATGTCAGCAGAGGAGTCTCTATATTGGCTAG
AGAAATGTTTATGTCAAGAGCATCAGGGCTTCGATGT
ACAAGTTAAGTATCATCAAAAAATGCTGAAGAATATG
TTACGTTTGACCGATAGTTTGGATTATCTATGGCCAG
TTAACCGTGAAATGCGGCTCATGAAAGCTGGGGGGTC
AATTGAACGGGCGATCACCAATAACATTAAAGCTTTT
CTTCAATTTAAAGAAACTGTAACCGTATTAAATTAGA
AAAACCGCAGTGAGGAATTTGAATGGAACCCATCGCA
ATTATTGGTCTTGCTTGCCGCTTTCCAGGGGCTGACA
ATCCAGAAGCTTTCTGGCAACTCATGCGAAATGGGGT
GGATGCGATCGCCGATATTCCTCCTGAACGTTGGGAT
ATTGAGCGTTTCTACGATCCCACACCTGCCACTGCCA
AGAAGATGTATAGTCGCCAGGGCGGTTTTCTAAAAAA
TGTCGATCAATTTGACCCTCAATTTTTCCGAATTTCT
CCCCTAGAAGCCACCTATCTAGATCCTCAACAAAGAC
TGCTACTGGAAGTCACCTGGGAAGCCTTAGAAAATGC
TGCCATTGTGCCTGAAACCTTAGCTGGTAGCCAATCA
GGGGTTTTTATTGGTATCAGTGATGTGGATTATCATC
GTTTGGCTTATCAAAGTCCTACTAACTTGACCGCCTA
TGTGGGTACAGGCAACAGCACCAGTATTGCGGCTAAC
CGTTTATCATATCTGTTTGATTTGCGTGGCCCCAGTT
TGGCCGTAGATACCGCTTGCTCTTCTTCCCTCGTCGC
CGTTCACTTGGCCTGTCAGAGTTTGCAAAGTCAAGAA
TCGAACCTCTGCTTAGTGGGGGGAGTTAATCTCATTT

-continued

TGTCGCCAGAGACAACCGTTGTTTTTTCCCAAGCGAG
AATGATCGCCCCCGACAGTCGTTGTAAAACCTTTGAC
GCGAGGGCCGATGGTTATGTGCGCTCGGAAGGCTGTG
GAGTAGTCGTACTTAAACGTCTTAGGGATGCCATTCA
GGACGGCGATCGCATTTTAGCAGTGATTGAAGGTTCC
GCGGTGAATCAGGATGGTTTAAGTAATGGACTCACGG
CCCCTAATGGCCCTGCTCAACAGGCGGTGATTCGTCA
GGCCCTGGCAAATGCCCAGGTAAAACCGGCCCAGATT
AGCTATGTCGAAGCCCATGGCACGGGGACAGAATTGG
GGGATCCGATCGAAGTTAAATCTCTGAAAGCGGTTTT
GGGTGAAAAGCGATCGCTCGATCAAACCTGTTGGCTC
GGTTCTGTGAAAACCAACATTGGTCATTTAGAAGCGG
CGGCGGGAATGGCGGGTCTGATTAAAGTCGTTCTCTG
CCTACAACACCAAGAAATTCCCCCTAATCTCCACTTT
CAAACCCTTAATCCCTATATTTCCCTAGCTGACACAG
CTTTTGCGATTCCCACTCAGGCTCAACCCTGGCGGAC
CAAACCCCCTAAGTCTGGTGAAAACGGTGTCGAACGA
CGTTTAGCAGGACTCAGTTCCTTTGGGTTTGGGGGGA
CAAATTCCCATGTGATTCTCAGCGAAGCCCCTGTCAC
CGTTAAAAACAATCAACAAAATGGGCAGAAGTTGATA
GAACGTCCCTGGCATTTGCTGACTTTATCTGCCAAGA
ATGAAGAAGCCTTAAAAGCCTTAGTCCATTGTTATCA
AAAGTATTTAGCTGATCATCATGAAATTCCTCTCGCT
GATGTTTGTTTTACGGCCAATAGTCGGCGATCGCACT
TTAATCATCGTTTAGGAGTAGTGGCTAGAGATCGCTT
AGAAATGTTGCAGAAGTTAGAGAACTTTAGTAACCAA
GAAAGGATGAGAGAACCGAAGAGTATTAACAAAAAAG
AAAAACCTAAAATTGTTTTTCTATTTGCCGGTCAAGG
TTCTCAATATGTAGGTATGGGTCGTCAACTGTACGAA
ACCCAACCCATCTTTCGCCAAACCTTGGATCGCTGTG
CTGAAATCCTGCGACCCCATTTAGATCAACCCCTCTT
AGAAATTCTTTATCCTGCTGACCCAGAAGCCGAAACA
GCGAGTTTTTACCTAGAGCAGACTGCCTATACCCAAC
CCACTTTATTCGCATTCGAGTATGCCCTAGCACAGTT
ATGGCGTTCCTGGGGAATAGAACCGGCGGCAGTAATT
GGTCACAGTGTCGGTGAATATGTGGCGGCCACCGTTG
CCGGAGCCTTAAGTCTAGAAGAAGGATTAACGCTAAT
TGCCAAACGGGCAAAACTGATGCAGTCTCTCCCCAAG
AATGGGACAATGATCGCCGTTTTTGCCGCAGAAGAGC
GGGTTAAAGCTGTTATTGAGCCTTATAGGACTGATGT

-continued

AGCGATCGCTGCTGTTAATGGACCAGAAAATTTTGTT
ATTTCAGGAAAAGCGCCGATTATTGCTGAGATTATCA
TTCATTTAACGGCAGCAGGAATAGAAGTTCGTCCTCT
CAAAGTTTCCCATGCTTTTCACTCGCACCTGTTGGAG
CCAATTTTAGATTCCTTAGAACAGGAAGCTGCTGCTA
TTTCCTACCAACCCCTGCAAATTCCCTTAGTTGCTAA
TTTAACGGGGGAAGTTCTACCAGAAGGAGCAACGATT
GAGGCTCGTTACTGGCGAAATCATGCACGCAACCCTG
TACAATTTTATGGGAGTATCCAAACGCTGATCGAGCA
GAAATTCAGTCTTTTTTTAGAAGTTAGCCCTAAACCG
ACTTTATCTCGATTGGGTCAACAATGTTGTCCAGAAA
GATCGACCACTTGGCTATTTTCCCTCGCCCTCCTCA
AGAAGAAGAACAAAGCCTACTAAATAGTTTGGCGATT
CTCTATGATTCCCAAGGAGCCGAAATAAACTGGGAAG
GGTTTAATCAAAATTATCCCCACCATTTACTGGCTCT
ACCGACCTATCCTTTTCAACGTCAACGCTATTGGCTT
GAAACCGGTAAACCGACTTCTGAAGAAACAACCATGA
CGACCAATGCCACTAATGTCCAAGCTATCTCCAGCCA
TCAAAAACAACAGGAGATTCTAATCACATTGCAAACC
CTAGTGGGAAATTTACTGCAATTGTCCCCTGCTGATG
TCAATGTTCATACACCTTTCCTGGAGATGGGGCAGA
TTCCATTGTCATGGTTGAGGCGGTCAGACGGATTGAG
AATACCTATAACGTTAAAATTGCTATGCGTCAGTTAT
TTGAGGAGTTATCTACTTTAGATGCTTTAGCTACTTA
TTTAGCTCAAAATCCGGCTACTGATTGCCAAACTGCT
CAAATTAATACCGAGGTGTTTTCTGCGCCCATTGCCT
GCTCAAATAACCGATCGCCCAATGTCGTGCTGAGTTC
TAATACCAACGGCTTTCAACGTCAAACAGCTTCTCCA
GGTTTTTCGGCGATCGCCCCCCTTGCAGGAATGGGAG
GAGCAGGGGAAATGGGAGGAGTTGAAGTGCCTCAAGT
TTCTGTGCCACAAACCAGTGCGGTAACAGCCTCAGGT
TCAACCGTTTCTAGTTCTGCCCTGGAAAACATTATGG
GTCAACAGTTACAACTGATGGCCAAACAGTTAGAAGT
CTTGCAAACGGCCAATTTTGCCCCGACGACTCCCCGA
ACCACAGAAAATTCCCCATCTTCCGTCAGTCAAAATA
GGTCAAACGGACTTACACAACAGTTAATTCCCCCCCA
GCAATTAGCGGCGAACCTAGAGCCAATAGCCAGTCGC
ACCCGTCAAACCAGCAATCAAGCTTCTGCTCCTAAAC
CGACAGTAACAGCCACTCCCTGGGGGCCGAAAAAACC
ACCCACAGGTGGATTCACTCCCCAACAACAGCAACAT

-continued

CTAGAGGCATTAATTGCTCGCTTTACGGAACGTACCA
AAACCTCTAAGCAAATTGTGCAAAGCGATCGCCTGCG
TTTAGCAGATAGTCGAGCCTCGGTCGGATTCCGTATG
TCTATTAAAGAGATGCTTTATCCCATTGTGGCCCAAC
GTTCTCAAGGATCAAGAATTTGGGATGTGGACGGTAA
TGAATATATTGATATGACGATGGGGCAAGGGGTAACG
CTGTTTGGGCATCAACCAGACTTCATTATGTCGGCCC
TACAAAGCCAACTCACTGAAGGCATTCATCTCAATCC
GCGATCGCCAATTGTGGGAGAAGTGGCCGCCTTAATT
TGTGAACTAACAGGAGCCGAACGAGCTTGTTTTTGCA
ACTCTGGAACCGAAGCCGTAATGGCCGCTATTCGTAT
CGCCAGGGCAACAACAGGTCGGAGTAAAATTGCCCTC
TTTGAAGGCTCCTATCATGGACATGCGGACGGAACCC
TTTTTAGGAACCAAATTATTGATAACCAACTCCACTC
TTTTCCCCTAGCTCTAGGCGTTCCCCCCAGCCTTAGT
TCCGATGTGGTGGTATTGGACTATGGCAGTGCGGAAG
CTCTGAACTATTTACAAACCCAGGGGCAGGATTTAGC
GGCGGTCTTAGTAGAACCAATTCAAAGTGGCAATCCT
CTACTCCAACCCCAACAATTTCTCCAAAGTCTGCGAC
AAATTACCAGTCAAATGGGCATTGCCCTGATTTTTGA
TGAAATGATTACGGGTTTTCGATCGCACCCAGGGGGA
GCGCAAGCTTTATTTGGAGTACAGGCGGATATTGCCA
CCTATGGCAAAGTAGTTGCGGGAGGAATGCCCATTGG
AGTTATTGCAGGTAAGGCCCATTATCTGGACAGCATT
GACGGGGGAATGTGGCGTTATGGCGATAAATCCTATC
CTGGGGTGGACAGAACCTTTTTTGGGGGAACCTTTAA
TCAGCATCCGTTAGCAATGGTAGCGGCTAGGGCTGTC
CTGACCCATTTAAAGGAGCAGGGGCCAGGTCTGCAAC
AACAATTAACTGAACGCACTGCGGCCTTAGCCGATAC
ACTGAATCATTATTTTCAAGCCGAAGAAGTTCCTATT
AAAATCGAACAGTTTAGTTCTTTCTTCCGGTTTGCCC
TCTCTGGCAATTTGGATTTACTTTTCTATCACATGGT
AGAAAAGGTATTTATGTCTGGGAATGGCGTAAACAT
TTTCTTTCAACCGCCCATACGGAAGCCGATCTTGCCC
AATTTGTCCAAGCGGTTAAGGATAGCATCACAGAATT
GCGTCAGGGAGGTTTTATCCCCGCAAAAAAGCCTTCC
TGGCCAGTGCCAACGCCTCAAATTGATCCCCCCCTAA
CCCCCCTTGATAAGGGGATTGATCCCCCCCTAACCCC
CCTTGATAAGGGGATTGATCCCCCCCTAACCCCCCTT
GATAAGGGGGAGATGTTGATGTCGCGCTTGATAAGG

-continued

```
GAGGAAATTCTCATTCTGTTAGGGACAGTAAGTTAGG
GAAAGGGAGCGGGTCTCAAGACCAAAAAACGATACAG
TTTAGCCTCTACTACTTTGGTAGCTATGAAGCGGAAT
TTAACCCGAATAAATATAACTTACTGTTTGAAGGAGC
TAAATTTGGCGATCGCGCTGGTTTTACGGCCCTTTGG
ATTCCTGAACGTCATTTCCACGCTTTTGGTGGTTTTT
CTCCCAATCCTTCGGTTTTGGCGGCGGCTTTAGCACG
GGAAACCAAACAGATTCAACTGCGATCAGGCAGTGTG
GTTTTACCGCTACATAATTCCATCCGAGTCGCCGAAG
AATGGGCAGTGGTGGACAATCTTTCCCAGGGCCGCGT
TGGTATTGCTTTTGCATCGGGTTGGCATCCCCAGGAT
TTTGTCTTGGCTCCCCAGTCCTTTGGCCAACATCGGG
AATTGATGTTCCAAGAAATTGAAACCGTCCAGAAACT
TTGGCGAGGGGAAGCGATCACCGTGCCAGACGGAAAG
GGTCAAAGGGTAGAGGTTAAAACCTATCCCCAACCGA
TGCAGTCCCAGTTACCCAGCTGGATTACTATTGTCAA
TAATCCCGATACCTATATCAGAGCAGGGGCGATCGGT
GCTAATATCCTTACCAATCTGATGGGGCAAAGCGTGG
AAGATTTAGCCCGTAATATTGCGCTATATCGTCAATC
TTTGGCAGAGCATGGTTATGATCCCGCGTCGGGAACG
GTGACAGTTCTCCTGCATACTTTTGTTGGCAAGGATT
TAGAACAAGTTCGAGAACAGGCTCGCCAACCCTTTGG
GCAATACCTCACCTCCTCTGTCGGACTCTTGCAGAAC
ATGGTCAAGAGCCAGGGCATGAAAGTGGATTTTGAAC
AATTAAGAGACGAAGATCGGGACTTTCTCCTCGCTTC
TGCCTATAAACGCTATACAGAAACCAGTGCTTTAATT
GGCACACCCGAATCCTGTCGTCAAATTATTGATCATT
TGCAGTCCATCGGTGTGGATGAAGTGGCTTGTTTTAT
TGATTTTGGGGTAGATGAACAAACAGTTTTGGCCAAT
TTACCCTATCTCCAGTCCCTAAAAGACTTATATCAAC
CTCATCTCCCCCCTTATCAAGGGGGGTTAGGGGGGGA
TCAATCCCCTTATCAAGGGGGGTTAGGGGGGGATCAA
TCCCCTTATCAAGGGGGGTTAGGGGGTGATCAATCCC
CTTATCAAGGGGGGTTAGGGGGTGATCAATCCCCTTA
TCAAGGGGGGTTAGGGGGGATCAATCCCCTTATCAA
GGAGAGTTAGGGGGGGATCAATCCCCTTATCAAGGGG
GGTTAGGGGGGGATCAAGTCCCTCTCACCGAAGCCCA
ACGACAACTGTGGATTTTGGCTCAATTAGGAGACAAC
GGCTCTGTGGCCTATAACCAATCAGTGACATTGCAAT
TAAGTGGCCCATTAAATCCCGTCGCAATGAATCAAGC
TATTCAACAAATCAGCGATCGCCATGAAGCGTTACGA
ACCAAAATTAATGCCCAGGGAGATAGTCAAGAAATCC
TGCCCCAGGTCGAAATTAACTGCCCTATCTTAGACTT
CAGTCTTGACCAAGCTTCGGCCCAACAGCAAGCAGAA
CAATGGTTAAAGGAAGAAAGTGAAAAACCCTTTGATT
TGAGCCAGGGTTCTCTCGTGCGTTGGCATCTACTCAA
ATTAGAACCAGAATTACATTTGTTAGTATTAACGGCC
CATCACATTATCAGTGACGGTTGGTCAATGGGGGTAA
TCCTTCGGGAATTAGGAGAGTTATATTCAGCCAAATG
TCAGGGTGTTACGGCTAATCTTAAAACCCCAAAACAG
TTTCGAGAATTGATTGAATGGCAAAGCCAGCCAAGCC
AAGGGGAAGAACTGAAAAAACAGCAAGCCTATTGGTT
AGCAACCCTTGCCGATCCCCCTGTTTTGAATTTACCC
ACTGACAAACCTCGTCCAGCTTTACCCAGTTACCAAG
CTAATCGTCGAAGTCTAACTTTAGATAGCCAATTTAC
AGAAAAACTAAAGCAATTTAGTCGTAAACAGGGCTGT
ACCTTGCTGATGACCCTGTTATCGGTTTATAACATTC
TCGTTCATCGTTTGACGGGACAGGATGATATTCTGGT
GGGTCTGCCAGCCTCTGGACGGGGGCTTTTAGATAGT
GAAGGTATGGTGGGTTATTGCACCCATTTTTTACCAA
TTCGCAGTCAATTAGCAGGTAATCCCACTTTTGCTGA
ATATCTCAAACAAATGCGGGGGGTTTTGTTGTCGGCT
TATGAACATCAGGACTATCCCTTTGCTCTTTTGCTCA
ATCAGTTAGATTTACCGCGTAATACCAGTCGCTCTCC
TTTAATTGATGTCAGTTTCAATTTAGAACCAGTTATT
AACCTACCCAAAATGAAAGGATTAGAGATTAGTTTGT
TGCCTCAAAGTGTAAGTTTTAAGGATCGAGATTTGCA
TTGGAATGTGACAGAAATGGGTGGAGAAGCTCTGATT
GATTGTGACTACAATACAGACTTATTTAAAGATGAAA
CGATTCAGCGTTGGTTAGGCCATTTTCAAACCTTACT
TGAGGCAGTTATTAATGATTCGCAACAAAATCTGCGG
GAATTACCCTTATTAAGTTCTGCTGAACGACAACAGT
TATTAGTGGATTGGAATCAAACCAAGACCGACTATCC
CCAAGATCAGTGTATTCATCAATTATTTGAAGCGCAA
GTTGAACGGACTCCCGATGCGATTGCGGTGGTATTTG
AAACTCAACAATTAACTTACAGTGAATTAAATTGTCG
AGCCAATCAGTTAGCACATTATTTACAAAAATTAGGA
GTTGGGCCAGAGGTCTTAGTCGGTATTTTGGTCGAAC
GTTCTTTAGAAATGATTGTCGGATTGTTAGGGATTCT
CAAGGCTGGGGAGCCTATGTACCTCTTGATCCTGAC
```

-continued

TATCCCCCTGAACGTCTTCAATTTATGTTAGAAGATA
GTCAATTTTTTCTCCTCTTAACCCAACAGCATTTACT
GGAATCTTTTGCTCAGTCTTCAGAAACGGCTACTCCC
AAGATTATTTGTTTGGATAGCGACTACCAAATTATTT
CCCAGGCAAAGAATATTAATCCCGAAAATTCAGTCAC
AACGAGTAATCTTGCCTATGTAATTTATACCTCTGGT
TCGACAGGTAAACCGAAGGGCGTGATGAATAATCATG
TTGCTATTAGTAATAAATTGTTATGGGTACAAGACAC
TTATCCTCTAACCACAGAAGACTGTATTTTACAAAAA
ACTCCCTTTAGTTTTGATGTTTCAGTGTGGAATTAT
TCTGGCCCCTACTAAACGGAGCGCGTTTGGTTTTTGC
CAAGCCGAATGGCCATAAAGATGCCAGTTACTTAGTC
AATCTGATTCAAGAGCAACAAGTAACAACGCTACATT
TTGTGTCTTCTATGCTACAGCTTTTTCTGACAGAAAA
AGACGTAGAAAAATGTAATAGTCTTAAACGAGTCATT
TGTAGTGGTGAAGCCCTTTCTTTAGAGCTTCAAGAAC
GTTTTTTTGCTCGTTTAGTCTGTGAATTACACAATCT
TTATGGACCGACAGAAGCCGCTATTCATGTCACATTT
TGGCAATGTCAATCAGATAGCAATTTGAAAACAGTAC
CCATTGGTCGGCCGATCGCTAATATCCAAATTTACAT
TTTAGACTCTCATCTTCAGCCAGTACCTATTGGAGTA
ATCGGAGAATTGCACATTGGTGGGGTTGGTTTGGCGC
GGGGTTATTTAAACAGGCCTGAGTTAACGGCGGAGAA
ATTTATTGCAAATCCGTTTGCTTCCCTTGATCCCCCC
CTAACCCCCCTTGATAAGGGGGGAGATGAGAGCTATA
AAACTTTTAAAAAGGGGGGAGAGCAACCATCAAGATT
GTATAAAACGGGAGATTTAGCTCGTTATTTACCCGAT
GGCAAGATTGAGTATCTAGGGCGCATTGATAATCAGG
TAAAAATTCGCGGTTTCCGGATTGAATTGGGGGAAAT
TGAAGCGGTTTTGCTATCCCATCCCCAGGTACGAGAA
GCGGTCGTTTTGGTGAGCGAAAGCGATCGCTCTGAAA
ATCGGGCTTTGGTCGCTTATATTGTCCCTAATGATCC
TGCTTGTACGACTCAATCATTACGAGAGTTTGTTAAA
CGGCAGCTTCCTGACTATATGATCCCAGCTTATTGGC
TGATCCTTGACAATTTACCGTTAACCAGCAATGGCAA
AATTGATCGTCGGGCTTTACCGTTACCTAATCCAGAG
TTAAATCGTTCGATAGACTATGTGGCTCCCAAAAATC
CTACCCAGGAGGCGATCGCCGCTATTTTTGGTCAAGT
TTTAAAACTGGAAAAAGTGGGAATTTATGATAACTTT
TTTGAGATCGGCGGTAATTCTTTGCAAGCCACTCAAG

-continued

TTATTTCACGCTTACGAGAAAGTTTTGCCCTAGAGTT
GCCCTTGCGTCGCCTGTTTGAACAACCGACTGTGGCG
GATTTGGCTTTAGCCGTAACGGACATTCATGCCACTT
TACAAAAATTACAAACCCCTATTGATGATTTATCAGG
CGATCGCGAGGAGATTGAACTATGAAATCTATTGAAA
CCTTTTTGTCAGATTTAGCCAATCAAGATATTAAACT
CTGGATGGACGGCGATCGCCTGCGTTGTAATGCACCC
CAGGGCCTATTAACCCCAGAGATTCAAACAGAACTGA
AAAACCGTAAAGCAGAAATCATTCACTTTCTCAATCA
ACTGGGTTCAGAGGAGCAAATTAATCCTAGAACGATT
CTTCCCATTCCTCGTGATGGCCAATTACCCCTCTCCT
TTGCCCAGTCGCGACTCTGGTTCTTGTATCAATTAGA
AGGAGCCACGGGAACCTATAACATGACAGGGGCCTTG
AGTTTAAGCGGGCCTCTTCAGGTCGAAGCCCTCAAAC
AAGCCCTAAGAACTATCATTCAACGCCATGAGCCATT
GCGTACCAGTTTCCAATCGGTTGACGGGGTTCCAGTG
CAGGTGATTAATCCCTATCCTGTTTGGGAATTAGCGA
TGGTTGATTTGACAGGAAGGAGACAGAAGCAGAAAAA
ATTGGCCTATCAGGAATCCCAAACCCCGTTTGATTTG
ACCAATAGTCCTTTGTTGAGGGTAACGCTCCTCAAAT
TACAGCCAGAAAAGCATATTTTATTAATTAATATGCA
CCATATTATTTCCGATGGCTGGTCAATCGGTGTTTTT
GTTCGTGAATTGTCCCATCTCTATAGGGCTTTTGTGG
CGGGTAAAGAACCAACTTTACCGATTTTACCAATTCA
GTATGCGGATTTTGCCGTTTGGCAGCGAGAGTGGTTA
CAGGGTAAGGTTTTAGCGGCTCAATTGGAATATTGGA
AGCGACAATTGGCAGATGCTCCTCCTCTGCTGGAACT
GCCCACTGATCGCCCTCGTCCCGCAATCCAAACCTTT
CAAGGCAAGACAGAAAGATTTGAGCTAGATAGGAAAC
TGACCCAAGAATTAAAGGCATTAAGTCAACAGTCGGG
TTGTACTTTATTTATGACTTTGTTGGCCGCTTTTGGG
GTGGTTTTATCCCGTTATAGTGGCCAGACTGATATCG
TCATTGGTTCGGCGATCGCCAACCGTAATCGCCAAGA
CATTGAGGGGTTAATTGGCTTTTTTGTTAACACTTTG
GCGTTGAGGTTAGATTTATCAGAAAAACCCAGCTTTG
CCGCTTTTTTAAAACAAGTACAGGAAGTCACTCAGGA
TGCCTATGAGCATCAAGACTTGCCCTTTGAAATGTTA
GTGGAAGAATTACAACTAGAGCGCAAATTAGACCGAA
ATCCTTTGGTACAGGTGATGTTTGCCCTACAAAATGC
GGCCAATGAAACCTGGAATTTACCTGGGTTGACCATT

-continued

GAAGAAATGTCTTGGGAACTTGAACCTGCCCGTTTTG

ACCTAGAGGTTCATTTATCAGAAGTTAACGCCGGCAT

AGCTGGATTCTGTTGCTACACCATTGATCTATTTGAT

GATGCAACGATCGCCCGTCTATTGGAACATTTTCAGA

ATCTTCTCAGGGCAATTATTGTTAATCCTCAAGAATC

GGTAAGTTTATTACCCTTGTTGTCAGAACAGGAAGAA

AAGCAACTTTTAGTTGATTGGAATCAAACCCAAGCCG

ATTATCCCCAAGATAAGCTTGTCCATCAGTTATTTGA

AGTTCAAGCAGCCAGTCAGCCAGAAGCGATCGCTCTA

ATCTTTGAAAATCAGGTTTTGACCTATGGAGAATTAA

ACCATCGCGCCAATCAATTAGCTCACTATCTTCAGTC

GTTAGGAGTCACCAAAGAACAAATCGTCGGGGTTTAT

CTGGAACGTTCCCTTGAAATGGCGATCGGATTTTTAG

GTATTCTCAAAGCAGGAGCCGCCTATCTCCCCATTGA

TCCTGAATATCCCTCAGTACGCACCCAATTTATTCTC

GAAGATACCCAACTTTCGCTTCTCTTAACTCAGGCAG

AACTGGCAGAAAAACTGCCCCAGACTCAAAACAAAAT

TATCTGTCTAGATCGGGACTGGCCAGAAATTACCTCC

CAACCCCAGACAAACCTAGACCTAAAGATAGAACCTA

ATAACCTAGCCTATTGCATCTATACTTCTGGTTCCAC

AGGACAACCCAAAGGAGTACTGATTTCCCATCAAGCC

CTACTCAACTTAATTTTCTGGCATCAACAAGCGTTTG

AGATTGGCCCCTTACATAAAGCGACCCAAGTGGCAGG

CATTGCTTTCGATGCAACGGTTTGGGAATTGTGGCCC

TATCTGACCACAGGAGCCTGTATTAATCTGGTTCCCC

AAAATATTCTGCTCTCACCGACGGATTTACGGGATTG

GTTGCTTAACCGAGAAATTACCATGAGTTTTGTGCCA

ACTCCTTTAGCTGAAAAATTATTATCCTTGGATTGGC

CTAACCATTCTTGTCTAAAAACCCTGTTACTGGGAGG

TGACAAACTTCATTTTTATCCTGCTGCGTCCCTTCCC

TTTCAGGTCATTAACAACTATGGCCCAACGGAAAATA

CAGTGGTTGCGACCTCTGGACTGGTCAAATCATCTTC

ATCTCATCACTTTGGAACTCCGACTATTGGTCGTCCC

ATTGCCAACGTCCAAATCTATTTATTAGACCAAAACC

TACAACCTGTCCCCATTGGTGTACCAGGAGAATTACA

TTTAGGTGGGCGGGTTTAGCGCAGGGCTATCTCAAT

CGTCCTGAGTTAACGGCTGAAAAATTTATTGCCAATC

CCTTTGATCCCCCCCTAACCCCCCTTGATAAGGGGGG

AGAAGAACCCTCAAAACTCTATAAAACGGGAGACTTA

GCCCGTTATTTACCCGATGGCAATGTAGAATTTTTGG

-continued

GACGTATTGACAATCAGGTAAAAATTCGGGGTTTTCG

CATCGAAACTGGGGAAATCGAAGCCGTTTTAAGTCAA

TATTTCCTATTAGCTGAAAGTGTAGTCGTTGCCAAGG

AAGATAATACTGGGGATAAACGCCTCGTGGCTTATTT

GGTTCCCGCCTTGCAAAATGAGGCCCTACCAGAGCAA

TTAGCCCAATGGCAAAGTGAATACATCAGTGATTGGC

AAAGTCTCTATGAAAGAACCTATAGTCAAGGGCAAGA

CAGCCTAGCTGATCTCACTTTTAATATCACGGGTTGG

AATAGCAGTTATACTCGTCAACCCCTTCCTGCTTCAG

AAATGCGAGAGTGGGTCGAAAACACTGTTAGTCGCAT

CTTGGCTTTCCAACCAGAACGCGGTTTAGAAATTGGT

TGTGGTACAGGTTTGTTACTCTCCAGGGTAGCAAAGC

ATTGTCTTGAATATTGGGCAACGGATTATTCCCAAGG

GGCGATCCAGTATGTTGAACGGGTTTGCAATGCCGTT

GAAGGTTTAGAACAGGTTAAATTACGCTGTCAAATGG

CAGATAATTTTGAAGGTATTGCCCTACATCAATTTGA

TACCGTCGTCTTAAATTCGATTATTCAGTATTTTCCC

AGTGTGGATTATCTGTTACAGGTGCTTGAAGGGGCGA

TCAACGTCATTGGCGAGCGAGGTCAGATTTTTGTCGG

GGATGTGCGGAGTTTACCCCTATTAGAGCCATATCAT

GCGGCTGTGCAATTAGCCCAAGCTTCTGACTCGAAAA

CTGTTGAACAATGGCAACAACAGGTGCGTCAAAGTGT

AGCAGGTGAAGAAGAACTGGTCATTGATCCCACATTG

TTCCTGGCTTTAAAACAACATTTTCCGCAAATTAGCT

GGGTAGAAATTCAACCGAAACGGGGTGTGGCTCACAA

TGAGTTAACTCAATTTCGCTATGATGTCACTCTCCAT

TTAGAGACTATCAATAATCAAGCATTATTGAGCGGCA

ATCCAACGGTAATTACCTGGTTAAATTGGCAACTTGA

CCAACTGTCTTTAACACAAATTAAAGATAAATTATTA

ACAGACAAACCTGAATTGTGGGAATTCGTGGTATTC

CTAATCAGCGAGTTGAAGAGGCTCTAAAAATTTGGGA

ATGGGTGGAAAATGCCCCTGATGTTGAAACGGTTGAA

CAACTCAAAAAACTTCTCAAACAACAAGTAGATACTG

GTATTAATCCTGAACAGGTTTGGCAATTAGCTGAGTC

TCTCGGTTACACCGCTCACCTTAGTTGGTGGGAAAGT

AGTCAAGACGGTTCCTTTGATGTCATTTTTCAGCGGA

ATTCAGAAGCGGAGGACTCAAAAAAATTAACCCTTTC

AAAACTTGCTTTCTGGGATGAAAAACCCTTTAAAATA

AAGCCCTGGAGTGACTATACTAACAACCCTCTGCGCG

GTAAGTTAGTCCAAAAATTAATTCCTAAAGTACGAGA

-continued

```
ATTTCTGCAAGAAAAACTACCCAGTTATATGGTTCCC
CAGGCGTTTGTGCTGCTTGATTCCCTTCCTTTGACCC
CCAATGGTAAGGTGGATCGTAAGGCGTTACCTTCTCC
TGATGCGGCGACTCGTGATTTAGCGAACAGTTTTGTC
TTACCCCGCAATCCGATTGAAGCTCAACTGACTCAAA
TTTGGAGTGAAGTTTTGGGACTGGAACGCATTGGCGT
TAAGGACAACTTTTTTGAATTGGGAGGACATTCTCTT
TTGGCTACCCAGGTTTTATCAAGAATTAATTCAGCCT
TTGGACTTGATCTTTCTGTGCAAATTATGTTTGAATC
ACCAACGATCGCGGGCATTGCGGGTTATATTCAAGCG
GTAGATTGGGTCGCCCAGGATCAAGCCGATAGCTCGT
TAAATCATGAAAATACTGAGGTAGTGGAGTTCTAAGT
TATGACGAAAAGATTGTTGAATTTGTCTGTTATCTA
CGGGATTTAGGCATTACTTTAGAAGCTGATGAAAACC
GCTTACGCTGTCAGGCTCCCGAAGGAATTTTGACCCC
AGCACTCCGTCAAGAAATTGGCGATCACAAACTGGAA
TTATTACAATTTTTACAATGGGTCAAACAGTCTAAAA
GTACCGCTCATTTGCCTATTAAACCTGTCGCTAGAGA
CGGTCATTTACCCCTGTCTTTTGCTCAACAACGTTTA
TGGTTTTTACATTATCTTTCCCCTGATAGTCGTTCCT
ACAATACCCTGGAAATATTGCAAATTGATGGGAATCT
CAATCTGACTGTGCTAGAGCAGAGTTTGGGGGAATTA
ATTAACCGCCATGAAATTTTAGAACAACATTCCCCA
CTGTTTCAGGGGAACCGATTCAGAAAATTGCACTTCC
TAGTCGTTTTCAGTTAAAAGTTGATAATTATCAAGAT
TTAGACGAAAATGAACAATCAGCTAAAATTCAACAAG
TAGCAGAATTGGAAGCAGGACAAGCTTTTGATTTAAC
GGTGGGGCCACTGATTCAGTTTAAGCTATTGCAATTG
AGTCCCCAGAAGTCGGTGCTGCTGTTGAAAATGCACC
ATATTATCTATGATGGCTGGTCTTTTGGGATTCTGAT
TCGGGAATTATCGGCTCTATACGAAGCATTTTTAAAG
AACTTAGCCAATCCTCTCCCTGCGTTGTCTATTCAGT
ATGCAGATTTTGCGGTTTGGCAACGTCAATATCTCTC
AGGTGAGGTCTTAGATAAACAACTCAATTATTGGCAA
GAACAGTTAGCAACAGTCTCTCCTGTTCTTACTTTAC
CAACGGATAGACCCCGTCCGGCGATACAAACTTTTCA
GGGAGGAGTTGAGCGTTTTCAACTGGATCAAAATGTC
ACTCAAGGTCTTAAAAAGTTAGGTCAAGATCAGGTTG
CAACCCTGTTTATGACGTTGTTGGCCGGTTTCGGCGT
TTTGCTATCTCGTTATAGTGGTCAATCTGATCTGATG
```

```
GTGGGTTCTCCGATCGCTAATCGTAATCAAGCAGCGA
TCGAACCTTTAATTGGCTTTTTTGCTAACACTTTGGC
TTTAAGAATTAATTTATCAGAAAATCCCAGTTTTTTA
GAATTATTAGAACAAGTTAAACAGACAACTTTAGAGG
GTTATGCTCACCAAGACCTACCCTTTGAGATGTTAGT
AGAAAAGCTACAACTTGACCGTGATTTGAGCAGAAAT
CCTTTAGTACAAGTCATGTTTGCGCTACAAAATACCT
CTCAAGATACTTGGAATCTTTCGGGTTTAAGTATTGA
AAGTTTATCTTTATCAGTGGAAGAAACTGTCAGATTT
GATCTAGAAGTAAACTGCTGGCAAAATTCAGAAGGTT
TAGCAATAGATTGGATTTACAGCAGAGATTTATTTGA
CACTGCAACAATTGCAAGAATGGGAGAACATTTTCAA
AATTTAGTTCAGGCAATCATACTCAATCCAAAAGCTA
CAGTTAAAGAACTTCCTTTATTAACACCCAAGGAACG
TGAGCAATTATTAATATCTTGGAATAATAGCAAGACT
GATTATCCTCAAGAGCAGTGTATTTATCAATTATTTG
AAGCACAAGTTGAACGGACTCCAAAGGCGATCGCAGT
GGTATTTGAGGAGCAATCATTAACATACACTGAATTA
AACCATCGCGCTAATCAGTTAGCCCATTATTTACAAA
CTTTAGGCGTGGGAGCAGAAGTCTTAGTCGGTATTTC
CCTAGAACGTTCTTTAGAGATGATTATCGGCTTATTA
GGGATTCTCAAGGTAGGTGGTGCTTATCTTCCTCTTG
ATCCAGACTATCCCACTGAGCGTCTTCAGTTGATGTT
AGAAGACAGTCAAGTTCCTTTTTTGATTACCCACAGT
TCTTTATTAGCAAAATTGCCTCCCTCTCAAGCAACTC
TGATTTGTTTAGATCATATCCAAGAGCAGATTTCTCA
ATATTCTCCAGATAATCTTCAATGTCAGTTAACTCCT
GCCAATTTAGCTAACGTTATTTATACCTCTGGCTCTA
CGGGTAAGCCTAAAGGGGTGATGGTTGAACATAAAGG
TTTAGTTAACTTAGCTCTTGCTCAAATTCAATCTTTT
GCAGTCAACCATAACAGTCGTGTGCTGCAATTTGCTT
CTTTTAGTTTTGATGCTTGTATTTCAGAAATTTTGAT
GACCTTTGGTTCTGGAGCGACGCTTTATCTTGCACAA
AAAGATGCTTTATTGCCAGGTCAGCCATTAATTGAAC
GGTTAGTAAAGAATGGAATTACTCATGTGACTTTGCC
GCCTTCAGCTTTAGTGGTTTTACCCCAGGAACCGTTA
CGCAACTTAGAAACCTTAATTGTGGCGGGTGAGGCTT
GTTCTCTTGATTTAGTGAAACAATGGTCAATCGATAG
AAACTTTTTCAATGCCTATGGGCCAACGGAAGCGAGT
GTTTGTGCCACTATTGGACAATGTTATCAAGATGATT
```

-continued

TAAAGGTGACGATTGGTAAGGCGATCGCCAATGTCCA
AATTTATATTTTAGATGCCTTTTTACAGCCGGTGCCG
GTGGGAGTGTCAGGAGAGTTATACATTGGTGGAGTTG
GGGTGGCAAGGGGCTATTTAAATCGTCCTGAATTAAC
CCAAGAAAAATTTATTGCTAATCCTTTTAGTAACGAC
CCAGATTCTCGGCTCTATAAAACTGGCGACTTAGCGC
GTTATTTACCCGATGGTAATATTGAATATTTAGGACG
CATTGACAATCAGGTAAAAATTCGCGGTTTTCGCATT
GAGTTAGGAGAAATTGAAGCGGTTCTGAGTCAATGTC
CCGATGTGCAAAATACGGCGGTGATTGTCCGCGAAGA
TACTCCTGGCGATAAGCGCTTAGTTGCCTATGTGGTT
CTTACTTCTGACTCCCAGATAACTACTAGCGAACTGC
GTCAATTTTTGGCGAATCAATTACCCGCCTATCTTGT
TCCTAATACCTTTGTTATTTTAGATGATTTGCCCCTA
ACCCCCAGTGGCAAATGCGATCGCCGTTCCTTACCTA
TACCCGAAACACAAGCGTTATCAAATGACTATATTGC
CCCTAAATCTCCCACTGAAGAAATTCTGGCTCAAATA
TGGGGGCAAGTTCTCAAGATAGAAAGAGTCAGCAGAG
AAGATAATTTCTTTGAATTGGGGGGGCATTCCCTTTT
AGCTACCCAGGTAATGTCCCGTCTGCGTGAAACTTTT
CAAGTCGAATTACCTTTGCGTAGTCTCTTTACCGCTC
CCACTATTGCTGAATTGGCCCTAACAATTGAGCAATC
TCAGCAAACCATTGCTGCTCCCCCCATCCTAACCAGA
AACGACAGTGCTAACCTCCCGTTATCTTTTGCTCAAC
AACGTTTATGGTTTCTGGATCAATTAGAACCTAACAG
CGCCTTTTATCATGTAGGGGGAGCCGTAAGACTAGAA
GGAACATTAAATATTACTGCCTTAGAGCAAAGCTTAA
AAGAAATTATTAATCGTCATGAAGCTTTACGCACAAA
TTTTATAACGATTGATGGTCAAGCCACTCAAATTATT
CACCCTACTATTAATTGGCGATTGTCTGTTGTTGATT
GTCAAAATTTAACCGACACTCAATCTCTGGAAATTGC
GGAAGCTGAAAAGCCCTTTAATCTTGCTCAAGATTGC
TTATTTCGTGCTACTTTATTCGTGCGATCACCGCTAG
AATATCATCTACTCGTGACCATGCACCATATTGTTAG
CGATGGCTGGTCAATTGGAGTATTTTTTCAAGAACTA
ACTCATCTTTACGCTGTCTATAATCAGGGTTTACCCT
CATCTTTAACGCCTATTAAAATACAATATGCTGATTT
TGCGGTCTGGCAACGGAATTGGTTACAAGGTGAAATT
TTAAGTAATCAATTGAATTATTGGCGCGAACAATTAG
CAAATGCTCCTGCTTTTTTACCTTTACCGACAGATAG

-continued

ACCTAGGCCCGCAATCCAAACTTTTATTGGTTCTCAT
CAAGAATTTAAACTTTCTCAGCCATTAAGCCAAAAAT
TGAATCAACTAAGTCAGAAGCATGGAGTGACTTTATT
TATGACTCTCCTGGCTGCTTTTGCTACCTTACTTTAC
CGTTATACAGGACAAGCAGATATTTTAGTTGGTTCTC
CTATTGCTAACCGTAATCGTAAGGAAATTGAGGGATT
AATCGGCTTTTTGTTAATACATTAGTTCTGAGATTG
AGTTTAGATAATGATTTAAGTTTTCAAAATTTGCTAA
ACCATGTTAGAGAGGTTTCTTTAGCAGCCTACGCCCA
TCAAGATTTACCTTTTGAAATGTTAGTAGAAGCACTA
CACCCTCAACGAGATCTCAGTCATACCCCTTTATTTC
AGGTAATGTTTGTTTTGCAAAATACACCAGTGGCTGA
TCTAGAACTTAAAAATGTAAAGGTTTGTCCTCTACCG
ATGGAAAATAAGACTGCTAAATTTGATTTAACCTTAT
CAATGGAGAATCTAGAGGAAGGATTGATTGGGGTTTG
GGAATATAACACCGATCTATTTAATGGCTCAACCATT
GAGCGAATGAGTGGACATTTTGTCACTTTGTTAGAAG
ATATTGTTGCCGCTCCAACGAAGTCAGTTTTACGGTT
GTCTTTGCTGACGCAAGAGGAAAAACTGCAATTATTG
ATTAAAAATCAGGGTGTTCAAGTTGATTATTCTCAAG
AGCAGTGCATCCATCAATTATTTGAAGCGCAAGTTGA
ACGGACTCCCGATGCGATTGCGGTGGTATTTGAGGAG
CAATCATTAACCTATGCTGAATTAAATCATCAAGCTA
ATCAGTTAGTCCATTACTTACAAACTTTAGGAATTGG
GCCAGAGGTCTTAGTCGCTATTTCAGTAGAACGTTCT
TTAGAAATGATTATCGGCTTATTAGCCATTCTCAAGG
CGTGTGGTGCTTATCTCCCTCTTGCTCCTGACTATCC
CACTGAGCGTCTTCAGTTCATGTTAGAAGATAGTCAA
GCTTCTTTTTTGATTACCCACAGTTCTTTATTAGAAA
AATTGCCTTCTTCTCAAGCGACTCTAATTTGTTTAGA
TCACATCCAAGAGCAGATTTCTCAATATTCTCCCGAT
AATCTTCAAAGTGAGTTAACTCCTTCCAATTTGGCTA
ACGTTATTTACACCTCTGGCTCTACGGGTAAGCCTAA
AGGGGTGATGGTTGAACATCGGGGCTTAGTTAACTTA
GCGAGTTCTCAAATTCAATCTTTTGCAGTCAAAAATA
ACAGTCGTGTACTGCAATTTGCTTCCTTTAGTTTTGA
TGCTTGTATTTCAGAAATTTTGATGACCTTTGGTTCT
GGAGCGACTCTTTATCTTGCTCAAAAAAATGATTTAT
TGCCAGGTCAGCCATTAATGGAAAGGTTAGAAAAGAA
TAAAATTACCCATGTTACTTTACCCCCTTCAGCTTTA

-continued

GCTGTTTTACCAAAAAAACCGTTACCCAACTTACAAA
CTTTAATTGTGGCGGGTGAGGCTTGTCCTCTGGATTT
AGTCAAACAATGGTCAGTCGGTAGAAACTTTTTCAAT
GCCTATGGCCCGACAGAAACGAGTGTTTGTGCCACGA
TTGGACAATGTTATCAAGATGATTTAAAGGTCACGAT
TGGTAAGGCGATCGCTAATGTCCAAATTTATATTTTG
GATGCCTTTTTACAACCAGTACCCATCGGAGTACCAG
GGGAATTATACATTGGTGGAGTCGGAGTTGCGAGGGG
TTATCTAAATCGTCCTGAATTAACGGCGGAAAGATTT
ATTCCTAATCCTTTTGATCCCCCCTAACCCCCCTTA
AAAAGGGGGAGATAAGAGCTATGAAACTTTTAAAAA
GGGGGAAGAGCAACCATCAAAACTCTATAAAACGGGA
GATTTAGCTCGTTATTTACCCGATGGCAATATTGAAT
ATTTAGGACGCATTGACAATCAGGTAAAAATTCGCGG
TTTTCGCATTGAGTTAGGAGAAATTGAAGCGGTTCTG
AGTCAATGTCCCGATGTGCAAAATACGGCGGTGATTG
TCCGTGAAGATACTCCTGGCGATAAACGTTTAGTTGC
CTATGTGGTTCTTACTTCTGACTCCCAGATAACTACT
AGCGAACTGCGTCAATTCTTGGCTAATCAATTACCTG
CCTATCTCGTTCCCAATACCTTTGTTATTTTAGATGA
TTTGCCCCTAACCCCCAATGGTAAATGCGATCGCCGT
TCCTTACCGCTTCCTGATGATCAGACCAGAAAAAATA
TTCCTAAAATTGGCCCGCGTAATTTAGTGGAATTACA
ATTAGCTCAAATCTGGTCAGAGATTTTAGGCATTAAT
AATATTGGTATTCAGGAAAACTTCTTTGAATTAGGCG
GTCATTCTTTATTAGCAGTCAGTCTGATCAATCGTAT
TGAACAAAAGTTAGATAAACGTTTACCATTAACCAGT
CTTTTTCAAAATGGAACCATAGCAAGTCTAGCTCAAT
TACTAGCGCAAGAAACAACTCAGCCAGCCTCTTCACC
GTTGATTGCTATCCAGTCTCAAGGTGATAAAACTCCA
TTTTTTGCTGTTCATCCCATTGGTGGTAATGTGCTAT
GTTATGCCGATTTAGCTCGTAATTTAGGAACGAAACA
GCCGTTTTATGGATTACAATCATTAGGGCTAAGTGAA
TTAGAAAAAACTGTAGCCTCTATTGAAGAAATGGCGA
TGATTTATATTGAAGCAATACAAACTGTTCAAGCCTC
TGGTCCCTACTATTTAGGAGGTTGGTCAATGGGAGGA
GTGATAGCTTTGAAATCGCCCAACAATTATTGACCC
AAGGTCAAGAAGTTGCTTTACTGGCTTTAATAGATAG
TTATTCTCCCAGTTTACTTAATTCAGTTAATAGGGAG
AAAAATTCTGCTAATTCCCTGACAGAAGAATTTAATG

AAGATATCAATATTGCCTATTCTTTCATCAGAGACTT
AGCAAGTATATTTAATCAAGAAATCTCTTTCTCTGGG
AGTGAACTTGCTCATTTTACATCAGACGAATTACTAG
ACAAGTTTATTACTTGGAGTCAAGAGACGAATCTTTT
GCCGTCAGATTTTGGGAAGCAGCAGGTTAAAACCTGG
TTTAAAGTTTTCCAGATTAATCACCAAGCTTTGAGCA
GCTATTCTCCCAAGACGTATCTGGGTAGAAGTGTTTT
CTTAGGAGCGGAAGACAGTTCTATTAAAAATCCTGGT
TGGCATCAAGTAATCAATGACTTGCAATCTCAATGGA
TTAGCGGCGATCACTACGGTTTAATTAAAAATCCAGT
CCTCGCTGAAAAACTCAATAGCTACCTAGCCTAAAAC
TTTCAAAAAGCCTGATTATTGTTTAAAATGAATGATC
GTTCACCGGTCAGAGGACAAGTATGACAACCCAAACA
GCTTCTAGTGCCAATGCCCTTGCTTCCTTTAACCAAT
TTTTAAGGGATGTAAAGGCGATCGCCCAACCCTATTG
GTATCCCACTGTATCAAATAAAAGAAGCTTTTCTGAG
GTTATTCGTTCCTGGGGAATGCTATCACTGCTTATCT
TTTTGATTGTGGGATTAGTCGCCGTCACGGCTTTTAA
TAGTTTTGTTAATCGTCGTTTAATTGATGTCATTATT
CAAGAAAAGATGCGTCTCAATTTGCCAGTACATTAA
CTGTCTATGCGATCGGATTAATCTGTGTAACGCTGCT
GGCAGGGTTCACTAAAGATATTCGCAAAAAAATTGCC
CTAGATTGGTATCAATGGTTAAACACCCAGATTGTAG
AGAAATATTTTAGTAATCGTGCCTATTATAAAATTAA
CTTTCAATCTGACATTGATAACCCCGATCAACGTCTA
GCCCAGGAAATTGAACCGATCGCCACAAACGCCATTA
GTTTCTCGGCCACTTTTTTGGAAAAAAGTTTGGAAAT
GCTAACTTTTTTAGTGGTAGTTTGGTCAATTTCTCGA
CAGATTGCTATTCCGCTAATGTTTTACACGATTATCG
GTAATTTATTGCCGCCTATCTAAATCAAGAATTAAG
CAAGATCAATCAGGCACAACTGCAATCAAAAGCAGAT
TATAACTATGCCTTAACCCATGTTCGGACTCATGCGG
AATCTATTGCTTTTTTTCGGGGAGAAAAAGAGGAACA
AAATATTATTCAGCGACGTTTTCAGGAAGTTATCAAT
GATACGAAAAATAAAATTAACTGGGAAAAAGGGAATG
AAATTTTTAGTCGGGGCTATCGTTCCGTCATTCAGTT
TTTTCCTTTTTTTAGTCCTTGGCCCTTTGTATATTAAA
GGAGAAATTGATTATGGACAAGTTGAGCAAGCTTCAT
TAGCTAGTTTTATGTTTGCATCGGCCCTGGGAGAATT
AATTACAGAATTTGGTACTTCAGGACGTTTTTCTAGT

-continued

```
TATGTAGAACGTTTAAATGAATTTTCTAATGCCTTAG

AAACTGTGACTAAACAAGCCGAGAATGTCAGCACAAT

TACAACCATAGAAGAAAATCATTTTGCCTTTGAACAC

GTCACCCTAGAAACCCCTGACTATGAAAAGGTGATTG

TTGAGGATTTATCTCTTACTGTTCAAAAAGGTGAAGG

ATTATTGATTGTCGGGCCCAGTGGTCGAGGTAAAAGT

TCTTTATTAAGGGCGATCGCCGGTTTATGGAATGCTG

GCACTGGGCGTTTAGTGCGTCCTCCCCTAGAAGAAAT

TCTCTTTTTGCCCCAACGTCCCTACATTATTTTGGGA

ACCTTACGCGAACAATTGCTGTATCCTCTAACCAATA

GTGAGATGAGCAATACCGAACTTCAAGCAGTATTACA

ACAAGTCAATTTGCAAAATGTGCTAAATCGGGTGGAT

GACTTTGACTCCGAAAAACCCTGGGAAAACATTCTCT
```

-continued

```
CCCTCGGTGAACAACAACGCCTAGCCTTTGCTCGATT

GTTAGTGAATTCTCCGAGTTTTACCATTTTAGATGAG

GCGACCAGTGCCTTAGATTTAACAAATGAGGGGATTT

TATACGAGCAATTACAAACTCGCAAGACAACCTTTAT

TAGTGTGGGTCATCGAGAAAGTTTGTTTAATTACCAT

CAATGGGTTTTAGAACTTTCTGCTGACTCTAGTTGGG

AACTCTTAAGCGTTCAAGATTATCGCCTTAAAAAGC

GGGAGAAATGTTTACTAATGCTTCGAGTAACAATTCC

ATAACACCCGATATTACTATCGATAATGGATCAGAAC

CAGAAATAGTCTATTCTCTTGAAGGATTTTCCCATCA

GGAAATGAAACTATTAACAGACCTATCACTCTCTAGC

ATTCGGAGTAAAGCCAGTCGAGGGAAGGTGATTACAG

CCAAGGATGGTTTTACCTACCTTTATGACAAAAATCC

TCAGATATTAAAGTGGCTCAGAACTTAA
```

---

The invention claimed is:

1. An isolated nucleic acid sequence encoding a peptide comprising a sequence with at least 95% identity to SEQ ID NO. 1.

2. An isolated nucleic acid encoding a microginin synthetase enzyme complex, wherein the isolated nucleic acid encodes the following activities:
   a) adenylation domain (A*) wherein, the adenylation domain comprises the nucleic acid sequence of claim 1
   b) acyl carrier protein (ACP)
   c) elongation module (EM) of polyketide synthases (PKS) comprising the following activities:
      i. ketoacylsynthase (KS)
      ii. acyl transferase (AT)
      iii. acyl carrier protein (ACP 2)
   d) aminotransferase (AMT)
   e) three to five elongation modules (EM) of non-ribosomal peptide synthetases (NRPS) comprising the following activities:
      i. condensation domain (C)
      ii. adenylation domain (A)
      iii. thiolation domain (T)
   f) thioesterase (TE).

3. The isolated nucleic acid according to claim 2, additionally comprising sequences encoding the following activities or domains:
   a) a monooxygenase (MO)
   b) an integrated N-methyltransferase domain (MT) within one or more elongation modules (EM) of NRPS;
   c) a non-integrated N-methyltrasferase (MT),
   d) a modifying activity (MA) wherein, said MA is selected from the group comprising the following activities: halogenase, sulfatase, glycosylase, racemase, O-methyltransferase and C-methyltransferase
   e) two or more peptide repeat spacer sequences (SP) consisting of one or more repeats of being either glycine rich or proline and leucine rich, located adjacently upstream and downstream of the MO or the MA, or both.

4. The isolated nucleic acid according to claim 2, further comprising at least one nucleic acid sequence encoding at least one protein sequence as follows:
   a. adenylation domain (A*) according to SEQ ID NO. 1
   b. acyl carrier protein (ACP) according to SEQ ID NO. 2
   c. elongation module of polyketide synthases:
      i. ketoacylsynthase domain (KS) according to SEQ ID NO. 3
      ii. acyl transferase domain (AT) according to SEQ ID NO. 4
      iii. acyl carrier protein domain (ACP 2) according to SEQ ID NO. 5
   d. aminotransferase (AMT) according to SEQ ID NO. 6
   e. elongation modules of non-ribosomal peptide synthetases:
      i. condensation domain (C) according to SEQ ID NO. 7
      ii. adenylation domain (A) according to SEQ ID NO. 8
      iii. thiolation domains (T) according to SEQ ID NO. 9
   f. elongation modules of non-ribosomal peptide synthetases responsible for the activation and condensation of leucin:
      i. condensation domain (C 2) according to SEQ ID NO. 10
      ii. adenylation domain (A 2) according to SEQ ID NO. 11
      iii. thiolation domain (T 2) according to SEQ ID NO. 12 g. elongation modules of non-ribosomal peptide synthetases responsible for the activation and condensation of tyrosine 1:
  i. condensation domain (C 3) according to SEQ ID NO. 13
  ii. adenylation domain (A 3) according to SEQ ID NO. 14
  iii. thiolation domain (T 3) according to SEQ ID NO. 15
h. elongation modules of non-ribosomal peptide synthetases responsible for the activation and condensation of tyrosine 2:
  i. condensation domain (C 4) according to SEQ ID NO. 16
  ii. adenylation domain (A 4) according to SEQ ID NO. 17
  iii. thiolation domain (T 4) according to SEQ ID NO. 18
i. thioesterase (TE) according to SEQ ID NO. 19
j.) two or more peptide repeat spacer sequences (SP1/SP2) according to SEQ ID NO. 21 and 22
l.) an integrated N-methyltransferase domain (MT) within the elongation module (EM) of the NRPS responsible for the activation and condensation of leucin according to SEQ ID 23 and
m.) a non-integrated N-methyltransferase (MT 2) according to SEQ ID NO. 24.

5. The isolated nucleic acid according to claim 2, further comprising at least one nucleic acid sequence as follows:
  a) an adenylation domain (A*) according to SEQ ID NO. 25,
  b) acyl carrier protein (ACP) according to SEQ ID NO. 26,
  c) elongation module of polyketide synthases encoding for the condensation of acetate:
    i. ketoacylsynthase domain (KS) according to SEQ ID NO. 27
    ii. acyl transferase domain (AT) according to SEQ ID NO. 28
    iii. acyl carrier protein domain (ACP 2) according to SEQ ID NO. 29
  d) aminotransferase (AMT) according to SEQ ID NO. 30,
  e) elongation modules of non-ribosomal peptide synthetases encoding for the activation and condensation of alanin:
    i. condensation domain (C) according to SEQ ID NO. 31
    ii. adenylation domain (A) according to SEQ ID NO. 32
    iii. thiolation domain (T) according to SEQ ID NO. 33
  f) elongation modules of non-ribosomal peptide synthetases encoding for the activation and condensation of leucin:
    i. condensation domain (C 2) according to SEQ ID NO. 34
    ii. adenylation domain (A 2) according to SEQ ID NO. 35
    iii. thiolation domain (T 2) according to SEQ ID NO. 36
  g) elongation modules of non-ribosomal peptide synthetases encoding for the activation and condensation of tyrosine 1:
    i. condensation domains (C 3) according to SEQ ID NO. 37
    ii. adenylation domains (A 3) according to SEQ ID NO. 38
    iii. thiolation domains (T 3) according to SEQ ID NO. 39
  h) elongation modules of non-ribosomal peptide synthetases encoding for the activation and condensation of tyrosine 2:
    i. condensation domains (C 4) according to SEQ ID NO. 40
    ii. adenylation domains (A 4) according to SEQ ID NO. 41
    iii. thiolation domains (T 4) according to SEQ ID NO. 42
  i) thioesterase (TE) according to SEQ ID NO. 43
  j) monooxygenase (MO) according to SEQ ID NO. 44
  k) two or more peptide repeat spacer sequences (SP1/2) according to SEQ ID NO. 45 and 46.
  l.) an integrated N-methyltransferase domain (MT) within the elongation module (EM) of the NRPS encoding for the activation and condensation of leucin according to SEQ ID 47 and
  m.) a non-integrated N-methyltrasferase (MT 2) according to SEQ ID NO. 48.

6. The isolated nucleic acid according to claim 2 wherein, the sequence parts of the nucleic acid encoding the microginin synthetase enzyme complex activities a) through f) are arranged upstream to downstream, respectively.

7. A vector comprising the nucleic acid of claim 2.

8. A microorganism transformed with the nucleic acid according to claim 2.

9. A vector according to claim 7 wherein, the vector is able to replicate autonomously.

10. A method of producing a microginin, comprising culturing a cell under conditions under which the cell will produce microginin, wherein said cell is transformed with a nucleic acid encoding the a recombinant microginin synthetase enzyme complex, according to claim 2, and wherein said cell does not produce the microginin in the absence of said nucleic acid, and wherein said cell is cultured in the presence of octanoic acid.

11. A microorganism transformed with the vector according to claim 6.

* * * * *

SEQUENCE LISTING

<160> NUMBER OF SEQ ID NOS: 61

<210> SEQ ID NO 1
<211> LENGTH: 580
<212> TYPE: PRT
<213> ORGANISM: Microcystis aeruginosa

<400> SEQUENCE: 1

```
Met Thr Ile Asn Tyr Gly Asp Leu Gln Glu Pro Phe Asn Lys Phe Ser
1               5                   10                  15

Thr Leu Val Glu Leu Leu Arg Tyr Arg Ala Ser Ser Gln Pro Glu Arg
            20                  25                  30

Leu Ala Tyr Ile Phe Leu Arg Asp Gly Glu Ile Glu Ala Arg Leu
        35                  40                  45

Thr Tyr Gly Glu Leu Asp Gln Lys Ala Arg Ala Ile Ala Ala Tyr Leu
    50                  55                  60

Gln Ser Leu Glu Ala Glu Gly Glu Arg Gly Leu Leu Leu Tyr Pro Pro
65                  70                  75                  80

Gly Leu Asp Phe Ile Ser Ala Phe Phe Gly Cys Leu Tyr Ala Gly Val
                85                  90                  95

Val Ala Ile Pro Ala Tyr Pro Pro Arg Arg Asn Gln Asn Leu Leu Arg
            100                 105                 110

Leu Gln Ala Ile Ile Ala Asp Ser Gln Ala Arg Phe Thr Phe Thr Asn
        115                 120                 125

Ala Ala Leu Phe Pro Ser Leu Lys Asn Gln Trp Ala Lys Asp Pro Glu
    130                 135                 140

Leu Gly Ala Met Glu Trp Ile Val Thr Asp Glu Ile Asp His His Leu
145                 150                 155                 160

Arg Glu Asp Trp Leu Glu Pro Thr Leu Glu Lys Asn Ser Leu Ala Phe
                165                 170                 175

Leu Gln Tyr Thr Ser Gly Ser Thr Gly Thr Pro Lys Gly Val Met Val
            180                 185                 190
```

```
Ser His His Asn Leu Leu Ile Asn Ser Ala Asp Leu Asp Arg Gly Trp
        195                 200                 205

Gly His Asp Gln Asp Ser Val Met Val Thr Trp Leu Pro Thr Phe His
    210                 215                 220

Asp Met Gly Leu Ile Tyr Gly Val Ile Gln Pro Leu Tyr Lys Gly Phe
225                 230                 235                 240

Leu Cys Tyr Met Met Ser Pro Ala Ser Phe Met Glu Arg Pro Leu Arg
                245                 250                 255

Trp Leu Gln Ala Leu Ser Asp Lys Lys Ala Thr His Ser Ala Ala Pro
            260                 265                 270

Asn Phe Ala Tyr Asp Leu Cys Val Arg Lys Ile Pro Pro Glu Lys Arg
        275                 280                 285

Ala Thr Leu Asp Leu Ser His Trp Cys Met Ala Leu Asn Gly Ala Glu
    290                 295                 300

Pro Val Arg Ala Glu Val Leu Lys Lys Phe Ala Glu Ala Phe Gln Val
305                 310                 315                 320

Ser Gly Phe Lys Ala Thr Ala Leu Cys Pro Gly Tyr Gly Leu Ala Glu
                325                 330                 335

Ala Thr Leu Lys Val Thr Ala Val Ser Tyr Asp Ser Pro Pro Tyr Phe
            340                 345                 350

Tyr Pro Val Gln Ala Asn Ala Leu Glu Lys Asn Lys Ile Val Gly Ala
        355                 360                 365

Thr Glu Thr Asp Thr Asn Val Gln Thr Leu Val Gly Cys Gly Trp Thr
    370                 375                 380

Thr Ile Asp Thr Gln Ile Val Ile Val Asn Pro Glu Thr Leu Lys Pro
385                 390                 395                 400

Cys Ser Pro Glu Ile Val Gly Glu Ile Trp Val Ser Gly Ser Thr Ile
                405                 410                 415

Ala Gln Gly Tyr Trp Gly Lys Pro Gln Glu Thr Gln Glu Thr Phe Gln
            420                 425                 430

Ala Tyr Leu Ala Asp Thr Gly Ala Gly Pro Phe Leu Arg Thr Gly Asp
        435                 440                 445

Leu Gly Phe Ile Lys Asp Gly Glu Leu Phe Ile Thr Gly Arg Leu Lys
    450                 455                 460

Glu Ile Ile Leu Ile Arg Gly Arg Asn Asn Tyr Pro Gln Asp Ile Glu
465                 470                 475                 480

Leu Thr Val Gln Asn Ser His Pro Ala Leu Arg Pro Ser Cys Gly Ala
                485                 490                 495

Ala Phe Thr Val Glu Asn Lys Gly Glu Glu Lys Leu Val Val Val Gln
            500                 505                 510

Glu Val Glu Arg Thr Trp Leu Arg Lys Val Asp Ile Asp Glu Val Lys
        515                 520                 525

Arg Ala Ile Arg Lys Ala Val Gln Glu Tyr Asp Leu Gln Val Tyr
    530                 535                 540

Ala Ile Ala Leu Ile Arg Thr Gly Ser Leu Pro Lys Thr Ser Ser Gly
545                 550                 555                 560

Lys Ile Gln Arg Arg Ser Cys Arg Ala Lys Phe Leu Glu Gly Ser Leu
                565                 570                 575

Glu Ile Leu Gly
            580

<210> SEQ ID NO 2
<211> LENGTH: 88
```

```
<212> TYPE: PRT
<213> ORGANISM: Microcystis aeruginosa

<400> SEQUENCE: 2

Met Ser Thr Glu Ile Pro Asn Asp Lys Lys Gln Pro Thr Leu Thr Lys
1               5                   10                  15

Ile Gln Asn Trp Leu Val Ala Tyr Met Thr Glu Met Met Glu Val Asp
                20                  25                  30

Glu Asp Glu Ile Asp Leu Ser Val Pro Phe Asp Glu Tyr Gly Leu Asp
            35                  40                  45

Ser Ser Met Ala Val Ala Leu Ile Ala Asp Leu Glu Asp Trp Leu Arg
    50                  55                  60

Arg Asp Leu His Arg Thr Leu Ile Tyr Asp Tyr Pro Thr Leu Glu Lys
65                  70                  75                  80

Leu Ala Lys Gln Val Ser Glu Pro
                85

<210> SEQ ID NO 3
<211> LENGTH: 431
<212> TYPE: PRT
<213> ORGANISM: Microcystis aeruginosa

<400> SEQUENCE: 3

Met Glu Pro Ile Ala Ile Ile Gly Leu Ala Cys Arg Phe Pro Gly Ala
1               5                   10                  15

Asp Asn Pro Glu Ala Phe Trp Gln Leu Met Arg Asn Gly Val Asp Ala
                20                  25                  30

Ile Ala Asp Ile Pro Pro Glu Arg Trp Asp Ile Glu Arg Phe Tyr Asp
            35                  40                  45

Pro Thr Pro Ala Thr Ala Lys Lys Met Tyr Ser Arg Gln Gly Gly Phe
    50                  55                  60

Leu Lys Asn Val Asp Gln Phe Asp Pro Gln Phe Phe Arg Ile Ser Pro
65                  70                  75                  80

Leu Glu Ala Thr Tyr Leu Asp Pro Gln Gln Arg Leu Leu Leu Glu Val
                85                  90                  95

Thr Trp Glu Ala Leu Glu Asn Ala Ala Ile Val Pro Glu Thr Leu Ala
                100                 105                 110

Gly Ser Gln Ser Gly Val Phe Ile Gly Ile Ser Asp Val Asp Tyr His
            115                 120                 125

Arg Leu Ala Tyr Gln Ser Pro Thr Asn Leu Thr Ala Tyr Val Gly Thr
    130                 135                 140

Gly Asn Ser Thr Ser Ile Ala Ala Asn Arg Leu Ser Tyr Leu Phe Asp
145                 150                 155                 160

Leu Arg Gly Pro Ser Leu Ala Val Asp Thr Ala Cys Ser Ser Ser Leu
                165                 170                 175

Val Ala Val His Leu Ala Cys Gln Ser Leu Gln Ser Gln Glu Ser Asn
            180                 185                 190

Leu Cys Leu Val Gly Gly Val Asn Leu Ile Leu Ser Pro Glu Thr Thr
    195                 200                 205

Val Val Phe Ser Gln Ala Arg Met Ile Ala Pro Asp Ser Arg Cys Lys
    210                 215                 220

Thr Phe Asp Ala Arg Ala Asp Gly Tyr Val Arg Ser Glu Gly Cys Gly
225                 230                 235                 240

Val Val Val Leu Lys Arg Leu Arg Asp Ala Ile Gln Asp Gly Asp Arg
                245                 250                 255
```

```
Ile Leu Ala Val Ile Glu Gly Ser Ala Val Asn Gln Asp Gly Leu Ser
            260                 265                 270

Asn Gly Leu Thr Ala Pro Asn Gly Pro Ala Gln Gln Ala Val Ile Arg
        275                 280                 285

Gln Ala Leu Ala Asn Ala Gln Val Lys Pro Ala Gln Ile Ser Tyr Val
    290                 295                 300

Glu Ala His Gly Thr Gly Thr Glu Leu Gly Asp Pro Ile Glu Val Lys
305                 310                 315                 320

Ser Leu Lys Ala Val Leu Gly Glu Lys Arg Ser Leu Asp Gln Thr Cys
                325                 330                 335

Trp Leu Gly Ser Val Lys Thr Asn Ile Gly His Leu Glu Ala Ala
                340                 345                 350

Gly Met Ala Gly Leu Ile Lys Val Val Leu Cys Leu Gln His Gln Glu
            355                 360                 365

Ile Pro Pro Asn Leu His Phe Gln Thr Leu Asn Pro Tyr Ile Ser Leu
        370                 375                 380

Ala Asp Thr Ala Phe Ala Ile Pro Thr Gln Ala Gln Pro Trp Arg Thr
385                 390                 395                 400

Lys Pro Pro Lys Ser Gly Glu Asn Gly Val Glu Arg Arg Leu Ala Gly
                405                 410                 415

Leu Ser Ser Phe Gly Phe Gly Gly Thr Asn Ser His Val Ile Leu
                420                 425                 430

<210> SEQ ID NO 4
<211> LENGTH: 324
<212> TYPE: PRT
<213> ORGANISM: Microcystis aeruginosa

<400> SEQUENCE: 4

Val Phe Leu Phe Ala Gly Gln Gly Ser Gln Tyr Val Gly Met Gly Arg
1               5                   10                  15

Gln Leu Tyr Glu Thr Gln Pro Ile Phe Arg Gln Thr Leu Asp Arg Cys
            20                  25                  30

Ala Glu Ile Leu Arg Pro His Leu Asp Gln Pro Leu Leu Glu Ile Leu
        35                  40                  45

Tyr Pro Ala Asp Pro Glu Ala Glu Thr Ala Ser Phe Tyr Leu Glu Gln
    50                  55                  60

Thr Ala Tyr Thr Gln Pro Thr Leu Phe Ala Phe Glu Tyr Ala Leu Ala
65                  70                  75                  80

Gln Leu Trp Arg Ser Trp Gly Ile Glu Pro Ala Val Ile Gly His
                85                  90                  95

Ser Val Gly Glu Tyr Val Ala Ala Thr Val Ala Gly Ala Leu Ser Leu
            100                 105                 110

Glu Glu Gly Leu Thr Leu Ile Ala Lys Arg Ala Lys Leu Met Gln Ser
        115                 120                 125

Leu Pro Lys Asn Gly Thr Met Ile Ala Val Phe Ala Ala Glu Glu Arg
    130                 135                 140

Val Lys Ala Val Ile Glu Pro Tyr Arg Thr Asp Val Ala Ile Ala Ala
145                 150                 155                 160

Val Asn Gly Pro Glu Asn Phe Val Ile Ser Gly Lys Ala Pro Ile Ile
                165                 170                 175

Ala Glu Ile Ile Ile His Leu Thr Ala Ala Gly Ile Glu Val Arg Pro
            180                 185                 190

Leu Lys Val Ser His Ala Phe His Ser His Leu Leu Glu Pro Ile Leu
        195                 200                 205
```

```
Asp Ser Leu Glu Gln Glu Ala Ala Ile Ser Tyr Gln Pro Leu Gln
    210                 215                 220

Ile Pro Leu Val Ala Asn Leu Thr Gly Glu Val Leu Pro Glu Gly Ala
225                 230                 235                 240

Thr Ile Glu Ala Arg Tyr Trp Arg Asn His Ala Arg Asn Pro Val Gln
                245                 250                 255

Phe Tyr Gly Ser Ile Gln Thr Leu Ile Glu Gln Lys Phe Ser Leu Phe
            260                 265                 270

Leu Glu Val Ser Pro Lys Pro Thr Leu Ser Arg Leu Gly Gln Gln Cys
        275                 280                 285

Cys Pro Glu Arg Ser Thr Thr Trp Leu Phe Ser Leu Ala Pro Pro Gln
290                 295                 300

Glu Glu Glu Gln Ser Leu Leu Asn Ser Leu Ala Ile Leu Tyr Asp Ser
305                 310                 315                 320

Gln Gly Ala Glu

<210> SEQ ID NO 5
<211> LENGTH: 68
<212> TYPE: PRT
<213> ORGANISM: Microcystis aeruginosa

<400> SEQUENCE: 5

Ile Thr Leu Gln Thr Leu Val Gly Asn Leu Leu Gln Leu Ser Pro Ala
1               5                   10                  15

Asp Val Asn Val His Thr Pro Phe Leu Glu Met Gly Ala Asp Ser Ile
                20                  25                  30

Val Met Val Glu Ala Val Arg Arg Ile Glu Asn Thr Tyr Asn Val Lys
            35                  40                  45

Ile Ala Met Arg Gln Leu Phe Glu Glu Leu Ser Thr Leu Asp Ala Leu
        50                  55                  60

Ala Thr Tyr Leu
65

<210> SEQ ID NO 6
<211> LENGTH: 394
<212> TYPE: PRT
<213> ORGANISM: Microcystis aeruginosa

<400> SEQUENCE: 6

Lys Glu Met Leu Tyr Pro Ile Val Ala Gln Arg Ser Gln Gly Ser Arg
1               5                   10                  15

Ile Trp Asp Val Asp Gly Asn Glu Tyr Ile Asp Met Thr Met Gly Gln
                20                  25                  30

Gly Val Thr Leu Phe Gly His Gln Pro Asp Phe Ile Met Ser Ala Leu
            35                  40                  45

Gln Ser Gln Leu Thr Glu Gly Ile His Leu Asn Pro Arg Ser Pro Ile
        50                  55                  60

Val Gly Glu Val Ala Ala Leu Ile Cys Glu Leu Thr Gly Ala Glu Arg
65                  70                  75                  80

Ala Cys Phe Cys Asn Ser Gly Thr Glu Ala Val Met Ala Ala Ile Arg
                85                  90                  95

Ile Ala Arg Ala Thr Thr Gly Arg Ser Lys Ile Ala Leu Phe Glu Gly
            100                 105                 110

Ser Tyr His Gly His Ala Asp Gly Thr Leu Phe Arg Asn Gln Ile Ile
        115                 120                 125
```

```
Asp Asn Gln Leu His Ser Phe Pro Leu Ala Leu Gly Val Pro Pro Ser
        130                 135                 140

Leu Ser Ser Asp Val Val Leu Asp Tyr Gly Ser Ala Glu Ala Leu
145                 150                 155                 160

Asn Tyr Leu Gln Thr Gln Gly Gln Asp Leu Ala Ala Val Leu Val Glu
                165                 170                 175

Pro Ile Gln Ser Gly Asn Pro Leu Leu Gln Pro Gln Gln Phe Leu Gln
            180                 185                 190

Ser Leu Arg Gln Ile Thr Ser Gln Met Gly Ile Ala Leu Ile Phe Asp
        195                 200                 205

Glu Met Ile Thr Gly Phe Arg Ser His Pro Gly Gly Ala Gln Ala Leu
210                 215                 220

Phe Gly Val Gln Ala Asp Ile Ala Thr Tyr Gly Lys Val Val Ala Gly
225                 230                 235                 240

Gly Met Pro Ile Gly Val Ile Ala Gly Lys Ala His Tyr Leu Asp Ser
                245                 250                 255

Ile Asp Gly Gly Met Trp Arg Tyr Gly Asp Lys Ser Tyr Pro Gly Val
            260                 265                 270

Asp Arg Thr Phe Phe Gly Gly Thr Phe Asn Gln His Pro Leu Ala Met
        275                 280                 285

Val Ala Ala Arg Ala Val Leu Thr His Leu Lys Glu Gln Gly Pro Gly
290                 295                 300

Leu Gln Gln Gln Leu Thr Glu Arg Thr Ala Ala Leu Ala Asp Thr Leu
305                 310                 315                 320

Asn His Tyr Phe Gln Ala Glu Glu Val Pro Ile Lys Ile Glu Gln Phe
                325                 330                 335

Ser Ser Phe Phe Arg Phe Ala Leu Ser Gly Asn Leu Asp Leu Leu Phe
            340                 345                 350

Tyr His Met Val Glu Lys Gly Ile Tyr Val Trp Glu Trp Arg Lys His
        355                 360                 365

Phe Leu Ser Thr Ala His Thr Glu Ala Asp Leu Ala Gln Phe Val Gln
370                 375                 380

Ala Val Lys Asp Ser Ile Thr Glu Leu Arg
385                 390

<210> SEQ ID NO 7
<211> LENGTH: 300
<212> TYPE: PRT
<213> ORGANISM: Microcystis aeruginosa

<400> SEQUENCE: 7

Gly Gly Asp Gln Val Pro Leu Thr Glu Ala Gln Arg Gln Leu Trp Ile
1               5                   10                  15

Leu Ala Gln Leu Gly Asp Asn Gly Ser Val Ala Tyr Asn Gln Ser Val
                20                  25                  30

Thr Leu Gln Leu Ser Gly Pro Leu Asn Pro Val Ala Met Asn Gln Ala
            35                  40                  45

Ile Gln Gln Ile Ser Asp Arg His Glu Ala Leu Arg Thr Lys Ile Asn
50                  55                  60

Ala Gln Gly Asp Ser Gln Glu Ile Leu Pro Gln Val Glu Ile Asn Cys
65                  70                  75                  80

Pro Ile Leu Asp Phe Ser Leu Asp Gln Ala Ser Ala Gln Gln Gln Ala
                85                  90                  95

Glu Gln Trp Leu Lys Glu Glu Ser Glu Lys Pro Phe Asp Leu Ser Gln
            100                 105                 110
```

```
Gly Ser Leu Val Arg Trp His Leu Leu Lys Leu Glu Pro Glu Leu His
        115                 120                 125

Leu Leu Val Leu Thr Ala His His Ile Ile Ser Asp Gly Trp Ser Met
    130                 135                 140

Gly Val Ile Leu Arg Glu Leu Gly Glu Leu Tyr Ser Ala Lys Cys Gln
145                 150                 155                 160

Gly Val Thr Ala Asn Leu Lys Thr Pro Lys Gln Phe Arg Glu Leu Ile
                165                 170                 175

Glu Trp Gln Ser Gln Pro Ser Gln Gly Glu Leu Lys Lys Gln Gln
            180                 185                 190

Ala Tyr Trp Leu Ala Thr Leu Ala Asp Pro Pro Val Leu Asn Leu Pro
        195                 200                 205

Thr Asp Lys Pro Arg Pro Ala Leu Pro Ser Tyr Gln Ala Asn Arg Arg
    210                 215                 220

Ser Leu Thr Leu Asp Ser Gln Phe Thr Glu Lys Leu Lys Gln Phe Ser
225                 230                 235                 240

Arg Lys Gln Gly Cys Thr Leu Leu Met Thr Leu Leu Ser Val Tyr Asn
                245                 250                 255

Ile Leu Val His Arg Leu Thr Gly Gln Asp Asp Ile Leu Val Gly Leu
            260                 265                 270

Pro Ala Ser Gly Arg Gly Leu Leu Asp Ser Glu Gly Met Val Gly Tyr
        275                 280                 285

Cys Thr His Phe Leu Pro Ile Arg Ser Gln Leu Ala
    290                 295                 300

<210> SEQ ID NO 8
<211> LENGTH: 430
<212> TYPE: PRT
<213> ORGANISM: Microcystis aeruginosa

<400> SEQUENCE: 8

Thr Tyr Ser Glu Leu Asn Cys Arg Ala Asn Gln Leu Ala His Tyr Leu
1               5                   10                  15

Gln Lys Leu Gly Val Gly Pro Glu Val Leu Val Gly Ile Leu Val Glu
            20                  25                  30

Arg Ser Leu Glu Met Ile Val Gly Leu Leu Gly Ile Leu Lys Ala Gly
        35                  40                  45

Gly Ala Tyr Val Pro Leu Asp Pro Asp Tyr Pro Pro Glu Arg Leu Gln
    50                  55                  60

Phe Met Leu Glu Asp Ser Gln Phe Phe Leu Leu Thr Gln Gln His
65                  70                  75                  80

Leu Leu Glu Ser Phe Ala Gln Ser Ser Glu Thr Ala Thr Pro Lys Ile
                85                  90                  95

Ile Cys Leu Asp Ser Asp Tyr Gln Ile Ile Ser Gln Ala Lys Asn Ile
            100                 105                 110

Asn Pro Glu Asn Ser Val Thr Thr Ser Asn Leu Ala Tyr Val Ile Tyr
        115                 120                 125

Thr Ser Gly Ser Thr Gly Lys Pro Lys Gly Val Met Asn Asn His Val
    130                 135                 140

Ala Ile Ser Asn Lys Leu Leu Trp Val Gln Asp Thr Tyr Pro Leu Thr
145                 150                 155                 160

Thr Glu Asp Cys Ile Leu Gln Lys Thr Pro Phe Ser Phe Asp Val Ser
                165                 170                 175

Val Trp Glu Leu Phe Trp Pro Leu Leu Asn Gly Ala Arg Leu Val Phe
```

-continued

```
                    180                 185                 190
Ala Lys Pro Asn Gly His Lys Asp Ala Ser Tyr Leu Val Asn Leu Ile
            195                 200                 205

Gln Glu Gln Gln Val Thr Thr Leu His Phe Val Ser Ser Met Leu Gln
210                 215                 220

Leu Phe Leu Thr Glu Lys Asp Val Glu Lys Cys Asn Ser Leu Lys Arg
225                 230                 235                 240

Val Ile Cys Ser Gly Glu Ala Leu Ser Leu Glu Leu Gln Glu Arg Phe
            245                 250                 255

Phe Ala Arg Leu Val Cys Glu Leu His Asn Leu Tyr Gly Pro Thr Glu
            260                 265                 270

Ala Ala Ile His Val Thr Phe Trp Gln Cys Gln Ser Asp Ser Asn Leu
            275                 280                 285

Lys Thr Val Pro Ile Gly Arg Pro Ile Ala Asn Ile Gln Ile Tyr Ile
            290                 295                 300

Leu Asp Ser His Leu Gln Pro Val Pro Ile Gly Val Ile Gly Glu Leu
305                 310                 315                 320

His Ile Gly Gly Val Gly Leu Ala Arg Gly Tyr Leu Asn Arg Pro Glu
                325                 330                 335

Leu Thr Ala Glu Lys Phe Ile Ala Asn Pro Phe Ala Ser Leu Asp Pro
            340                 345                 350

Pro Leu Thr Pro Leu Asp Lys Gly Asp Glu Ser Tyr Lys Thr Phe
            355                 360                 365

Lys Lys Gly Gly Glu Gln Pro Ser Arg Leu Tyr Lys Thr Gly Asp Leu
370                 375                 380

Ala Arg Tyr Leu Pro Asp Gly Lys Ile Glu Tyr Leu Gly Arg Ile Asp
385                 390                 395                 400

Asn Gln Val Lys Ile Arg Gly Phe Arg Ile Glu Leu Gly Glu Ile Glu
            405                 410                 415

Ala Val Leu Leu Ser His Pro Gln Val Arg Glu Ala Val Val
            420                 425                 430
```

<210> SEQ ID NO 9
<211> LENGTH: 65
<212> TYPE: PRT
<213> ORGANISM: Microcystis aeruginosa

<400> SEQUENCE: 9

```
Glu Ala Ile Ala Ala Ile Phe Gly Gln Val Leu Lys Leu Glu Lys Val
1               5                   10                  15

Gly Ile Tyr Asp Asn Phe Phe Glu Ile Gly Gly Asn Ser Leu Gln Ala
            20                  25                  30

Thr Gln Val Ile Ser Arg Leu Arg Glu Ser Phe Ala Leu Glu Leu Pro
        35                  40                  45

Leu Arg Arg Leu Phe Glu Gln Pro Thr Val Ala Asp Leu Ala Leu Ala
    50                  55                  60

Val
65
```

<210> SEQ ID NO 10
<211> LENGTH: 300
<212> TYPE: PRT
<213> ORGANISM: Microcystis aeruginosa

<400> SEQUENCE: 10

Pro Arg Asp Gly Gln Leu Pro Leu Ser Phe Ala Gln Ser Arg Leu Trp

```
            1               5                   10                  15

Phe Leu Tyr Gln Leu Glu Gly Ala Thr Gly Thr Tyr Asn Met Thr Gly
                        20                  25                  30

Ala Leu Ser Leu Ser Gly Pro Leu Gln Val Glu Ala Leu Lys Gln Ala
                        35                  40                  45

Leu Arg Thr Ile Ile Gln Arg His Glu Pro Leu Arg Thr Ser Phe Gln
                50                  55                  60

Ser Val Asp Gly Val Pro Val Gln Val Ile Asn Pro Tyr Pro Val Trp
        65                  70                  75                  80

Glu Leu Ala Met Val Asp Leu Thr Gly Lys Glu Thr Glu Ala Glu Lys
                                85                  90                  95

Leu Ala Tyr Gln Glu Ser Gln Thr Pro Phe Asp Leu Thr Asn Ser Pro
                        100                 105                 110

Leu Leu Arg Val Thr Leu Leu Lys Leu Gln Pro Glu Lys His Ile Leu
                        115                 120                 125

Leu Ile Asn Met His His Ile Ile Ser Asp Gly Trp Ser Ile Gly Val
                        130                 135                 140

Phe Val Arg Glu Leu Ser His Leu Tyr Arg Ala Phe Val Ala Gly Lys
        145                 150                 155                 160

Glu Pro Thr Leu Pro Ile Leu Pro Ile Gln Tyr Ala Asp Phe Ala Val
                                165                 170                 175

Trp Gln Arg Glu Trp Leu Gln Gly Lys Val Leu Ala Ala Gln Leu Glu
                        180                 185                 190

Tyr Trp Lys Arg Gln Leu Ala Asp Ala Pro Pro Leu Leu Glu Leu Pro
                        195                 200                 205

Thr Asp Arg Pro Arg Pro Ala Ile Gln Thr Phe Gln Gly Lys Thr Glu
                        210                 215                 220

Arg Phe Glu Leu Asp Arg Lys Leu Thr Gln Glu Leu Lys Ala Leu Ser
        225                 230                 235                 240

Gln Gln Ser Gly Cys Thr Leu Phe Met Thr Leu Leu Ala Ala Phe Gly
                        245                 250                 255

Val Val Leu Ser Arg Tyr Ser Gly Gln Thr Asp Ile Val Ile Gly Ser
                        260                 265                 270

Ala Ile Ala Asn Arg Asn Arg Gln Asp Ile Glu Gly Leu Ile Gly Phe
                        275                 280                 285

Phe Val Asn Thr Leu Ala Leu Arg Leu Asp Leu Ser
                        290                 295                 300

<210> SEQ ID NO 11
<211> LENGTH: 409
<212> TYPE: PRT
<213> ORGANISM: Microcystis aeruginosa

<400> SEQUENCE: 11

Thr Tyr Gly Glu Leu Asn His Arg Ala Asn Gln Leu Ala His Tyr Leu
        1               5                   10                  15

Gln Ser Leu Gly Val Thr Lys Glu Gln Ile Val Gly Val Tyr Leu Glu
                        20                  25                  30

Arg Ser Leu Glu Met Ala Ile Gly Phe Leu Gly Ile Leu Lys Ala Gly
                        35                  40                  45

Ala Ala Tyr Leu Pro Ile Asp Pro Glu Tyr Pro Ser Val Arg Thr Gln
                        50                  55                  60

Phe Ile Leu Glu Asp Thr Gln Leu Ser Leu Leu Leu Thr Gln Ala Glu
        65                  70                  75                  80
```

```
Leu Ala Glu Lys Leu Pro Gln Thr Gln Asn Lys Ile Ile Cys Leu Asp
                85                  90                  95

Arg Asp Trp Pro Glu Ile Thr Ser Gln Pro Gln Thr Asn Leu Asp Leu
            100                 105                 110

Lys Ile Glu Pro Asn Asn Leu Ala Tyr Cys Ile Tyr Thr Ser Gly Ser
        115                 120                 125

Thr Gly Gln Pro Lys Gly Val Leu Ile Ser His Gln Ala Leu Leu Asn
130                 135                 140

Leu Ile Phe Trp His Gln Gln Ala Phe Glu Ile Gly Pro Leu His Lys
145                 150                 155                 160

Ala Thr Gln Val Ala Gly Ile Ala Phe Asp Ala Thr Val Trp Glu Leu
                165                 170                 175

Trp Pro Tyr Leu Thr Thr Gly Ala Cys Ile Asn Leu Val Pro Gln Asn
            180                 185                 190

Ile Leu Leu Ser Pro Thr Asp Leu Arg Asp Trp Leu Leu Asn Arg Glu
        195                 200                 205

Ile Thr Met Ser Phe Val Pro Thr Pro Leu Ala Glu Lys Leu Leu Ser
    210                 215                 220

Leu Asp Trp Pro Asn His Ser Cys Leu Lys Thr Leu Leu Leu Gly Gly
225                 230                 235                 240

Asp Lys Leu His Phe Tyr Pro Ala Ala Ser Leu Pro Phe Gln Val Ile
                245                 250                 255

Asn Asn Tyr Gly Pro Thr Glu Asn Thr Val Ala Thr Ser Gly Leu
            260                 265                 270

Val Lys Ser Ser Ser His His Phe Gly Thr Pro Thr Ile Gly Arg
        275                 280                 285

Pro Ile Ala Asn Val Gln Ile Tyr Leu Leu Asp Gln Asn Leu Gln Pro
    290                 295                 300

Val Pro Ile Gly Val Pro Gly Glu Leu His Leu Gly Gly Ala Gly Leu
305                 310                 315                 320

Ala Gln Gly Tyr Leu Asn Arg Pro Glu Leu Thr Ala Glu Lys Phe Ile
                325                 330                 335

Ala Asn Pro Phe Asp Pro Pro Leu Thr Pro Leu Asp Lys Gly Gly Glu
            340                 345                 350

Glu Pro Ser Lys Leu Tyr Lys Thr Gly Asp Leu Ala Arg Tyr Leu Pro
        355                 360                 365

Asp Gly Asn Val Glu Phe Leu Gly Arg Ile Asp Asn Gln Val Lys Ile
    370                 375                 380

Arg Gly Phe Arg Ile Glu Thr Gly Glu Ile Glu Ala Val Leu Ser Gln
385                 390                 395                 400

Tyr Phe Leu Leu Ala Glu Ser Val Val
                405

<210> SEQ ID NO 12
<211> LENGTH: 65
<212> TYPE: PRT
<213> ORGANISM: Microcystis aeruginosa

<400> SEQUENCE: 12

Ala Gln Leu Thr Gln Ile Trp Ser Glu Val Leu Gly Leu Glu Arg Ile
1               5                   10                  15

Gly Val Lys Asp Asn Phe Phe Glu Leu Gly Gly His Ser Leu Leu Ala
            20                  25                  30

Thr Gln Val Leu Ser Arg Ile Asn Ser Ala Phe Gly Leu Asp Leu Ser
        35                  40                  45
```

```
Val Gln Ile Met Phe Glu Ser Pro Thr Ile Ala Gly Ile Ala Gly Tyr
    50                  55                  60

Ile
65

<210> SEQ ID NO 13
<211> LENGTH: 305
<212> TYPE: PRT
<213> ORGANISM: Microcystis aeruginosa

<400> SEQUENCE: 13

Ala Arg Asp Gly His Leu Pro Leu Ser Phe Ala Gln Gln Arg Leu Trp
1               5                   10                  15

Phe Leu His Tyr Leu Ser Pro Asp Ser Arg Ser Tyr Asn Thr Leu Glu
                20                  25                  30

Ile Leu Gln Ile Asp Gly Asn Leu Asn Leu Thr Val Leu Glu Gln Ser
            35                  40                  45

Leu Gly Glu Leu Ile Asn Arg His Glu Ile Phe Arg Thr Thr Phe Pro
    50                  55                  60

Thr Val Ser Gly Glu Pro Ile Gln Lys Ile Ala Leu Pro Ser Arg Phe
65                  70                  75                  80

Gln Leu Lys Val Asp Asn Tyr Gln Asp Leu Asp Glu Asn Glu Gln Ser
                85                  90                  95

Ala Lys Ile Gln Gln Val Ala Glu Leu Glu Ala Gly Gln Ala Phe Asp
            100                 105                 110

Leu Thr Val Gly Pro Leu Ile Gln Phe Lys Leu Leu Gln Leu Ser Pro
        115                 120                 125

Gln Lys Ser Val Leu Leu Lys Met His His Ile Ile Tyr Asp Gly
    130                 135                 140

Trp Ser Phe Gly Ile Leu Ile Arg Glu Leu Ser Ala Leu Tyr Glu Ala
145                 150                 155                 160

Phe Leu Lys Asn Leu Ala Asn Pro Leu Pro Ala Leu Ser Ile Gln Tyr
                165                 170                 175

Ala Asp Phe Ala Val Trp Gln Arg Gln Tyr Leu Ser Gly Glu Val Leu
            180                 185                 190

Asp Lys Gln Leu Asn Tyr Trp Gln Glu Gln Leu Ala Thr Val Ser Pro
        195                 200                 205

Val Leu Thr Leu Pro Thr Asp Arg Pro Arg Pro Ala Ile Gln Thr Phe
    210                 215                 220

Gln Gly Gly Val Glu Arg Phe Gln Leu Asp Gln Asn Val Thr Gln Gly
225                 230                 235                 240

Leu Lys Lys Leu Gly Gln Asp Gln Val Ala Thr Leu Phe Met Thr Leu
                245                 250                 255

Leu Ala Gly Phe Gly Val Leu Leu Ser Arg Tyr Ser Gly Gln Ser Asp
            260                 265                 270

Leu Met Val Gly Ser Pro Ile Ala Asn Arg Asn Gln Ala Ala Ile Glu
        275                 280                 285

Pro Leu Ile Gly Phe Phe Ala Asn Thr Leu Ala Leu Arg Ile Asn Leu
    290                 295                 300

Ser
305

<210> SEQ ID NO 14
<211> LENGTH: 395
<212> TYPE: PRT
```

<213> ORGANISM: Microcystis aeruginosa

<400> SEQUENCE: 14

```
Thr Tyr Thr Glu Leu Asn His Arg Ala Asn Gln Leu Ala His Tyr Leu
1               5                   10                  15
Gln Thr Leu Gly Val Gly Ala Glu Val Leu Val Gly

```
<210> SEQ ID NO 15
<211> LENGTH: 65
<212> TYPE: PRT
<213> ORGANISM: Microcystis aeruginosa

<400> SEQUENCE: 15

Glu Ile Leu Ala Gln Ile Trp Gly Gln Val Leu Lys Ile Glu Arg Val
1               5                   10                  15

Ser Arg Glu Asp Asn Phe Phe Glu Leu Gly Gly His Ser Leu Leu Ala
                20                  25                  30

Thr Gln Val Met Ser Arg Leu Arg Glu Thr Phe Gln Val Glu Leu Pro
            35                  40                  45

Leu Arg Ser Leu Phe Thr Ala Pro Thr Ile Ala Glu Leu Ala Leu Thr
        50                  55                  60

Ile
65

<210> SEQ ID NO 16
<211> LENGTH: 299
<212> TYPE: PRT
<213> ORGANISM: Microcystis aeruginosa

<400> SEQUENCE: 16

Asn Asp Ser Ala Asn Leu Pro Leu Ser Phe Ala Gln Gln Arg Leu Trp
1               5                   10                  15

Phe Leu Asp Gln Leu Glu Pro Asn Ser Ala Phe Tyr His Val Gly Gly
                20                  25                  30

Ala Val Arg Leu Glu Gly Thr Leu Asn Ile Thr Ala Leu Glu Gln Ser
            35                  40                  45

Leu Lys Glu Ile Ile Asn Arg His Glu Ala Leu Arg Thr Asn Phe Ile
        50                  55                  60

Thr Ile Asp Gly Gln Ala Thr Gln Ile Ile His Pro Thr Ile Asn Trp
65                  70                  75                  80

Arg Leu Ser Val Val Asp Cys Gln Asn Leu Thr Asp Thr Gln Ser Leu
                85                  90                  95

Glu Ile Ala Glu Ala Glu Lys Pro Phe Asn Leu Ala Gln Asp Cys Leu
            100                 105                 110

Phe Arg Ala Thr Leu Phe Val Arg Ser Pro Leu Glu Tyr His Leu Leu
        115                 120                 125

Val Thr Met His His Ile Val Ser Asp Gly Trp Ser Ile Gly Val Phe
    130                 135                 140

Phe Gln Glu Leu Thr His Leu Tyr Ala Val Tyr Asn Gln Gly Leu Pro
145                 150                 155                 160

Ser Ser Leu Thr Pro Ile Lys Ile Gln Tyr Ala Asp Phe Ala Val Trp
                165                 170                 175

Gln Arg Asn Trp Leu Gln Gly Glu Ile Leu Ser Asn Gln Leu Asn Tyr
            180                 185                 190

Trp Arg Glu Gln Leu Ala Asn Ala Pro Ala Phe Leu Pro Leu Pro Thr
        195                 200                 205

Asp Arg Pro Arg Pro Ala Ile Gln Thr Phe Ile Gly Ser His Gln Glu
    210                 215                 220

Phe Lys Leu Ser Gln Pro Leu Ser Gln Lys Leu Asn Gln Leu Ser Gln
225                 230                 235                 240

Lys His Gly Val Thr Leu Phe Met Thr Leu Leu Ala Ala Phe Ala Thr
                245                 250                 255
```

```
Leu Leu Tyr Arg Tyr Thr Gly Gln Ala Asp Ile Leu Val Gly Ser Pro
            260                 265                 270

Ile Ala Asn Arg Asn Arg Lys Glu Ile Glu Gly Leu Ile Gly Phe Phe
        275                 280                 285

Val Asn Thr Leu Val Leu Arg Leu Ser Leu Asp
    290                 295

<210> SEQ ID NO 17
<211> LENGTH: 415
<212> TYPE: PRT
<213> ORGANISM: Microcystis aeruginosa

<400> SEQUENCE: 17

Thr Tyr Ala Glu Leu Asn His Gln Ala Asn Gln Leu Val His Tyr Leu
1               5                  10                  15

Gln Thr Leu Gly Ile Gly Pro Glu Val Leu Ala Ile Ser Val Glu
            20                  25                  30

Arg Ser Leu Glu Met Ile Ile Gly Leu Leu Ala Ile Leu Lys Ala Cys
        35                  40                  45

Gly Ala Tyr Leu Pro Leu Ala Pro Asp Tyr Pro Thr Glu Arg Leu Gln
    50                  55                  60

Phe Met Leu Glu Asp Ser Gln Ala Ser Phe Leu Ile Thr His Ser Ser
65                  70                  75                  80

Leu Leu Glu Lys Leu Pro Ser Ser Gln Ala Thr Leu Ile Cys Leu Asp
                85                  90                  95

His Ile Gln Glu Gln Ile Ser Gln Tyr Ser Pro Asp Asn Leu Gln Ser
            100                 105                 110

Glu Leu Thr Pro Ser Asn Leu Ala Asn Val Ile Tyr Thr Ser Gly Ser
        115                 120                 125

Thr Gly Lys Pro Lys Gly Val Met Val Glu His Arg Gly Leu Val Asn
    130                 135                 140

Leu Ala Ser Ser Gln Ile Gln Ser Phe Ala Val Lys Asn Asn Ser Arg
145                 150                 155                 160

Val Leu Gln Phe Ala Ser Phe Ser Phe Asp Ala Cys Ile Ser Glu Ile
                165                 170                 175

Leu Met Thr Phe Gly Ser Gly Ala Thr Leu Tyr Leu Ala Gln Lys Asn
            180                 185                 190

Asp Leu Leu Pro Gly Gln Pro Leu Met Glu Arg Leu Glu Lys Asn Lys
        195                 200                 205

Ile Thr His Val Thr Leu Pro Pro Ser Ala Leu Ala Val Leu Pro Lys
    210                 215                 220

Lys Pro Leu Pro Asn Leu Gln Thr Leu Ile Val Ala Gly Glu Ala Cys
225                 230                 235                 240

Pro Leu Asp Leu Val Lys Gln Trp Ser Val Gly Arg Asn Phe Phe Asn
                245                 250                 255

Ala Tyr Gly Pro Thr Glu Thr Ser Val Cys Ala Thr Ile Gly Gln Cys
            260                 265                 270

Tyr Gln Asp Asp Leu Lys Val Thr Ile Gly Lys Ala Ile Ala Asn Val
        275                 280                 285

Gln Ile Tyr Ile Leu Asp Ala Phe Leu Gln Pro Val Pro Ile Gly Val
    290                 295                 300

Pro Gly Glu Leu Tyr Ile Gly Gly Val Gly Val Ala Arg Gly Tyr Leu
305                 310                 315                 320

Asn Arg Pro Glu Leu Thr Ala Glu Arg Phe Ile Pro Asn Pro Phe Asp
                325                 330                 335
```

```
Pro Pro Leu Thr Pro Leu Lys Lys Gly Gly Asp Lys Ser Tyr Glu Thr
                340                 345                 350

Phe Lys Lys Gly Glu Glu Gln Pro Ser Lys Leu Tyr Lys Thr Gly Asp
            355                 360                 365

Leu Ala Arg Tyr Leu Pro Asp Gly Asn Ile Glu Tyr Leu Gly Arg Ile
        370                 375                 380

Asp Asn Gln Val Lys Ile Arg Gly Phe Arg Ile Glu Leu Gly Glu Ile
385                 390                 395                 400

Glu Ala Val Leu Ser Gln Cys Pro Asp Val Gln Asn Thr Ala Val
                405                 410                 415

<210> SEQ ID NO 18
<211> LENGTH: 65
<212> TYPE: PRT
<213> ORGANISM: Microcystis aeruginosa

<400> SEQUENCE: 18

Leu Gln Leu Ala Gln Ile Trp Ser Glu Ile Leu Gly Ile Asn Asn Ile
1               5                   10                  15

Gly Ile Gln Glu Asn Phe Phe Glu Leu Gly Gly His Ser Leu Leu Ala
            20                  25                  30

Val Ser Leu Ile Asn Arg Ile Glu Gln Lys Leu Asp Lys Arg Leu Pro
        35                  40                  45

Leu Thr Ser Leu Phe Gln Asn Gly Thr Ile Ala Ser Leu Ala Gln Leu
    50                  55                  60

Leu
65

<210> SEQ ID NO 19
<211> LENGTH: 227
<212> TYPE: PRT
<213> ORGANISM: Microcystis aeruginosa

<400> SEQUENCE: 19

Thr Pro Phe Phe Ala Val His Pro Ile Gly Gly Asn Val Leu Cys Tyr
1               5                   10                  15

Ala Asp Leu Ala Arg Asn Leu Gly Thr Lys Gln Pro Phe Tyr Gly Leu
            20                  25                  30

Gln Ser Leu Gly Leu Ser Glu Leu Glu Lys Thr Val Ala Ser Ile Glu
        35                  40                  45

Glu Met Ala Met Ile Tyr Ile Glu Ala Ile Gln Thr Val Gln Ala Ser
    50                  55                  60

Gly Pro Tyr Tyr Leu Gly Gly Trp Ser Met Gly Gly Val Ile Ala Phe
65                  70                  75                  80

Glu Ile Ala Gln Gln Leu Leu Thr Gln Gly Gln Glu Val Ala Leu Leu
                85                  90                  95

Ala Leu Ile Asp Ser Tyr Ser Pro Ser Leu Leu Asn Ser Val Asn Arg
            100                 105                 110

Glu Lys Asn Ser Ala Asn Ser Leu Thr Glu Glu Phe Asn Glu Asp Ile
        115                 120                 125

Asn Ile Ala Tyr Ser Phe Ile Arg Asp Leu Ala Ser Ile Phe Asn Gln
    130                 135                 140

Glu Ile Ser Phe Ser Gly Ser Glu Leu Ala His Phe Thr Ser Asp Glu
145                 150                 155                 160

Leu Leu Asp Lys Phe Ile Thr Trp Ser Gln Glu Thr Asn Leu Leu Pro
                165                 170                 175
```

```
Ser Asp Phe Gly Lys Gln Gln Val Lys Thr Trp Phe Lys Val Phe Gln
            180                 185                 190

Ile Asn His Gln Ala Leu Ser Ser Tyr Ser Pro Lys Thr Tyr Leu Gly
        195                 200                 205

Arg Ser Val Phe Leu Gly Ala Glu Asp Ser Ser Ile Lys Asn Pro Gly
210                 215                 220

Trp His Gln
225

<210> SEQ ID NO 20
<211> LENGTH: 345
<212> TYPE: PRT
<213> ORGANISM: Microcystis aeruginosa

<400> SEQUENCE: 20

Phe Ser Leu Tyr Tyr Phe Gly Ser Tyr Glu Ala Glu Phe Asn Pro Asn
1               5                   10                  15

Lys Tyr Asn Leu Leu Phe Glu Gly Ala Lys Phe Gly Asp Arg Ala Gly
            20                  25                  30

Phe Thr Ala Leu Trp Ile Pro Glu Arg His Phe His Ala Phe Gly Gly
        35                  40                  45

Phe Ser Pro Asn Pro Ser Val Leu Ala Ala Leu Ala Arg Glu Thr
    50                  55                  60

Lys Gln Ile Gln Leu Arg Ser Gly Ser Val Val Leu Pro Leu His Asn
65                  70                  75                  80

Ser Ile Arg Val Ala Glu Glu Trp Ala Val Val Asp Asn Leu Ser Gln
                85                  90                  95

Gly Arg Val Gly Ile Ala Phe Ala Ser Gly Trp His Pro Gln Asp Phe
            100                 105                 110

Val Leu Ala Pro Gln Ser Phe Gly Gln His Arg Glu Leu Met Phe Gln
        115                 120                 125

Glu Ile Glu Thr Val Gln Lys Leu Trp Arg Gly Glu Ala Ile Thr Val
    130                 135                 140

Pro Asp Gly Lys Gly Gln Arg Val Glu Val Lys Thr Tyr Pro Gln Pro
145                 150                 155                 160

Met Gln Ser Gln Leu Pro Ser Trp Ile Thr Ile Val Asn Asn Pro Asp
                165                 170                 175

Thr Tyr Ile Arg Ala Gly Ala Ile Gly Ala Asn Ile Leu Thr Asn Leu
            180                 185                 190

Met Gly Gln Ser Val Glu Asp Leu Ala Arg Asn Ile Ala Leu Tyr Arg
        195                 200                 205

Gln Ser Leu Ala Glu His Gly Tyr Asp Pro Ala Ser Gly Thr Val Thr
    210                 215                 220

Val Leu Leu His Thr Phe Val Gly Lys Asp Leu Glu Gln Val Arg Glu
225                 230                 235                 240

Gln Ala Arg Gln Pro Phe Gly Gln Tyr Leu Thr Ser Ser Val Gly Leu
                245                 250                 255

Leu Gln Asn Met Val Lys Ser Gln Gly Met Lys Val Asp Phe Glu Gln
            260                 265                 270

Leu Arg Asp Glu Asp Arg Asp Phe Leu Leu Ala Ser Ala Tyr Lys Arg
        275                 280                 285

Tyr Thr Glu Thr Ser Ala Leu Ile Gly Thr Pro Glu Ser Cys Arg Gln
    290                 295                 300

Ile Ile Asp His Leu Gln Ser Ile Gly Val Asp Glu Val Ala Cys Phe
```

```
                305                 310                 315                 320
Ile Asp Phe Gly Val Asp Glu Gln Thr Val Leu Ala Asn Leu Pro Tyr
                325                 330                 335

Leu Gln Ser Leu Lys Asp Leu Tyr Gln
            340                 345

<210> SEQ ID NO 21
<211> LENGTH: 33
<212> TYPE: PRT
<213> ORGANISM: Microcystis aeruginosa

<400> SEQUENCE: 21

Ile Asp Pro Pro Leu Thr Pro Leu Asp Lys Gly Ile Asp Pro Pro Leu
1               5                   10                  15

Thr Pro Leu Asp Lys Gly Ile Asp Pro Pro Leu Thr Pro Leu Asp Lys
            20                  25                  30

Gly

<210> SEQ ID NO 22
<211> LENGTH: 77
<212> TYPE: PRT
<213> ORGANISM: Microcystis aeruginosa

<400> SEQUENCE: 22

Pro Tyr Gln Gly Gly Leu Gly Gly Asp Gln Ser Pro Tyr Gln Gly Gly
1               5                   10                  15

Leu Gly Gly Asp Gln Ser Pro Tyr Gln Gly Gly Leu Gly Gly Asp Gln
            20                  25                  30

Ser Pro Tyr Gln Gly Gly Leu Gly Gly Asp Gln Ser Pro Tyr Gln Gly
        35                  40                  45

Gly Leu Gly Gly Asp Gln Ser Pro Tyr Gln Gly Glu Leu Gly Gly Asp
    50                  55                  60

Gln Ser Pro Tyr Gln Gly Gly Leu Gly Gly Asp Gln Val
65                  70                  75

<210> SEQ ID NO 23
<211> LENGTH: 382
<212> TYPE: PRT
<213> ORGANISM: Microcystis aeruginosa

<400> SEQUENCE: 23

Pro Ala Ser Glu Met Arg Glu Trp Val Glu Asn Thr Val Ser Arg Ile
1               5                   10                  15

Leu Ala Phe Gln Pro Glu Arg Gly Leu Glu Ile Gly Cys Gly Thr Gly
            20                  25                  30

Leu Leu Leu Ser Arg Val Ala Lys His Cys Leu Glu Tyr Trp Ala Thr
        35                  40                  45

Asp Tyr Ser Gln Gly Ala Ile Gln Tyr Val Glu Arg Val Cys Asn Ala
    50                  55                  60

Val Glu Gly Leu Glu Gln Val Lys Leu Arg Cys Gln Met Ala Asp Asn
65                  70                  75                  80

Phe Glu Gly Ile Ala Leu His Gln Phe Asp Thr Val Val Leu Asn Ser
            85                  90                  95

Ile Ile Gln Tyr Phe Pro Ser Val Asp Tyr Leu Leu Gln Val Leu Glu
        100                 105                 110

Gly Ala Ile Asn Val Ile Gly Glu Arg Gly Gln Ile Phe Val Gly Asp
    115                 120                 125
```

```
Val Arg Ser Leu Pro Leu Leu Glu Pro Tyr His Ala Val Gln Leu
        130                 135                 140

Ala Gln Ala Ser Asp Ser Lys Thr Val Glu Gln Trp Gln Gln Val
145                 150                 155                 160

Arg Gln Ser Val Ala Gly Glu Glu Leu Val Ile Asp Pro Thr Leu
                165                 170                 175

Phe Leu Ala Leu Lys Gln His Phe Pro Gln Ile Ser Trp Val Glu Ile
                180                 185                 190

Gln Pro Lys Arg Gly Val Ala His Asn Glu Leu Thr Gln Phe Arg Tyr
                195                 200                 205

Asp Val Thr Leu His Leu Glu Thr Ile Asn Asn Gln Ala Leu Leu Ser
        210                 215                 220

Gly Asn Pro Thr Val Ile Thr Trp Leu Asn Trp Gln Leu Asp Gln Leu
225                 230                 235                 240

Ser Leu Thr Gln Ile Lys Asp Lys Leu Leu Thr Asp Lys Pro Glu Leu
                245                 250                 255

Trp Gly Ile Arg Gly Ile Pro Asn Gln Arg Val Glu Glu Ala Leu Lys
                260                 265                 270

Ile Trp Glu Trp Val Glu Asn Ala Pro Asp Val Glu Thr Val Glu Gln
                275                 280                 285

Leu Lys Lys Leu Leu Lys Gln Gln Val Asp Thr Gly Ile Asn Pro Glu
        290                 295                 300

Gln Val Trp Gln Leu Ala Glu Ser Leu Gly Tyr Thr Ala His Leu Ser
305                 310                 315                 320

Trp Trp Glu Ser Ser Gln Asp Gly Ser Phe Asp Val Ile Phe Gln Arg
                325                 330                 335

Asn Ser Glu Ala Glu Asp Ser Lys Lys Leu Thr Leu Ser Lys Leu Ala
                340                 345                 350

Phe Trp Asp Glu Lys Pro Phe Lys Ile Lys Pro Trp Ser Asp Tyr Thr
                355                 360                 365

Asn Asn Pro Leu Arg Gly Lys Leu Val Gln Lys Leu Ile Pro
        370                 375                 380

<210> SEQ ID NO 24
<211> LENGTH: 270
<212> TYPE: PRT
<213> ORGANISM: Microcystis aeruginosa

<400> SEQUENCE: 24

Met Thr Asn Tyr Gly Lys Ser Met Ser His Tyr Tyr Asp Leu Val Val
1               5                   10                  15

Gly His Lys Gly Tyr Asn Lys Asp Tyr Ala Thr Glu Val Glu Phe Ile
                20                  25                  30

His Asn Leu Val Glu Thr Tyr Thr Thr Glu Ala Lys Ser Ile Leu Tyr
            35                  40                  45

Leu Gly Cys Gly Thr Gly Tyr His Ala Ala Leu Leu Ala Gln Lys Gly
        50                  55                  60

Tyr Ser Val His Gly Val Asp Leu Ser Ala Glu Met Leu Glu Gln Ala
65                  70                  75                  80

Lys Thr Arg Ile Glu Asp Glu Thr Ile Ala Ser Asn Leu Ser Phe Ser
                85                  90                  95

Gln Gly Asn Ile Cys Glu Ile Arg Leu Asn Arg Gln Phe Asn Val Val
                100                 105                 110

Leu Ala Leu Phe His Val Val Asn Tyr Gln Thr Thr Asn Gln Asn Leu
            115                 120                 125
```

-continued

```
Leu Ala Thr Phe Ala Thr Val Lys Asn His Leu Lys Ala Gly Gly Ile
        130                 135                 140

Phe Ile Cys Asp Val Ser Tyr Gly Ser Tyr Val Leu Gly Glu Phe Lys
145                 150                 155                 160

Ser Arg Pro Thr Ala Ser Ile Leu Arg Leu Glu Asp Asn Ser Asn Gly
                165                 170                 175

Asn Glu Val Thr Tyr Ile Ser Glu Leu Asn Phe Leu Thr His Glu Asn
            180                 185                 190

Ile Val Glu Val Thr His Asn Leu Trp Val Thr Asn Gln Glu Asn Gln
        195                 200                 205

Leu Leu Glu Asn Ser Arg Glu Thr His Leu Gln Arg Tyr Leu Phe Lys
    210                 215                 220

Pro Glu Val Glu Leu Leu Ala Asp Ala Cys Glu Leu Thr Val Leu Asp
225                 230                 235                 240

Ala Met Pro Trp Leu Glu Gln Arg Pro Leu Thr Asn Ile Pro Cys Pro
                245                 250                 255

Ser Val Cys Phe Val Ile Gly His Lys Thr Thr His Ser Ala
            260                 265                 270

<210> SEQ ID NO 25
<211> LENGTH: 1743
<212> TYPE: DNA
<213> ORGANISM: Microcystis aeruginosa

<400> SEQUENCE: 25
atgactatta actatggtga tctgcaagaa cccttaata aattctcaac cctagttgaa         60
ttactccgtt atcgggcaag cagtcaaccg gaacgcctcg cctatatttt tctgcgagac       120
ggagaaatcg aagaagctcg tttaacctat ggggaactgg atcaaaaggc tagggcgatc       180
gccgcttatc tacaatcctt agaagccgag ggcgaaaggg gtttactgct ctatccccca       240
ggactagatt ttatttcagc tttttttggt tgtttatatg cgggagtcgt tgccattccc       300
gcctatccac cccgacggaa tcaaaaacctt ttgcgtttac aggcgattat tgccgattct       360
caagcccgat ttaccttcac caatgccgct ctatttccca gtttaaaaaa ccaatgggct       420
aaagaccctg aattaggagc aatggaatgg attgttaccg atgaaattga ccatcacctc       480
agggaggatt ggctagaacc aaccctcgaa aaaaacagtc tcgcttttct acaatacacc       540
tctggttcaa cgggaactcc aaagggagta atggtcagtc accataattt gttgattaat       600
tcagccgatt tagatcgtgg ttggggccat gatcaagata gcgtaatggt cacttggcta       660
ccgaccttcc atgatatggg tctgatttat ggggttattc agcctttgta caaggatt       720 ctttgttaca tgatgtcccc tgccagcttt atggaacgac cgttacgttg ttacaggcc       780 ctttctgata aaaagcaac ccatagtgcg ccccaact ttgcctacga tctttgtgtg       840
cggaaaattc cccctgaaaa acgggctacg ttagacttaa gccattggtg catggcctta       900 aatgggccg aacccgtcag agcggaggta cttaaaaagt ttgcggaggc ttttcaagtt       960
tctggtttca aagccacagc cctttgtcct ggctacggtt tagcagaagc cacccctgaaa    1020 gttacggcgg ttagttatga cagtcccct tactttatc ccgttcaggc taatgcttta    1080
gaaaaaaata gattgtggg agccactgaa accgatacca atgtgcagac cctcgtgggc    1140
tgcggctgga caacgattga tactcaaatc gtcattgtca atcctgaaac cctgaaacct    1200
tgctcccctg aaattgtcgg cgaaatttgg gtatcaggtc aacaatcgc ccaaggctat    1260 tggggaaaac ctcaagagac tcaggaaacc tttcaagctt atttggcaga tacaggagcc    1320
```

```
gggccttttc tgcgaacagg agacttgggc ttcattaaag atggtgaatt gtttatcaca    1380
ggtcggctca aggaaattat tctgattcga ggacgcaata attatcccca ggatattgaa    1440
ttaaccgtcc aaaatagtca tcccgctctg cgtcccagtt gtggggctgc ttttaccgtt    1500
gaaaataagg gcgaagaaaa gctcgtggtc gttcaggaag tggagcgcac ctggctccgt    1560
aaggtagata tagatgaggt aaaaagagcc attcgtaaag ctgttgtcca ggaatatgat    1620
ttacaggttt atgcgatcgc gctgatcagg actggcagtt taccaaaaac ctctagcggt    1680
aaaattcagc gtcgtagctg tcgggccaaa ttttagagg aagcctgga aattttgggc    1740 taa                                                                  1743

<210> SEQ ID NO 26
<211> LENGTH: 267
<212> TYPE: DNA
<213> ORGANISM: Microcystis aeruginosa

<400> SEQUENCE: 26
atgtccacag aaatcccaaa cgacaaaaaa caaccgaccc taacgaaaat tcaaaactgg      60
ttagtggctt acatgacaga gatgatggaa gtggacgaag atgagattga tctgagcgtt     120 cccttttgatg aatatggtct cgattcttct atggcagttg ctttgatcgc tgatctagag    180
gattggttac gacgagattt acatcgcacc ctgatctacg attatccaac tctagaaaag    240
ttggctaaac aggttagtga accctga                                         267

<210> SEQ ID NO 27
<211> LENGTH: 1293
<212> TYPE: DNA
<213> ORGANISM: Microcystis aeruginosa

<400> SEQUENCE: 27
atggaaccca tcgcaattat tggtcttgct tgccgcttc caggggctga caatccagaa       60
gctttctggc aactcatgcg aaatggggtg gatgcgatcg ccgatattcc tcctgaacgt     120
tgggatattg agcgttttcta cgatcccaca cctgccactg ccaagaagat gtatagtcgc     180
cagggcggtt ttctaaaaaa tgtcgatcaa tttgacccctc aatttttccg aatttctccc    240
ctagaagcca cctatctaga tcctcaacaa agactgctac tggaagtcac ctgggaagcc    300
ttagaaaatg ctgccattgt gcctgaaacc ttagctggta gccaatcagg ggttttatt      360 ggtatcagtg atgtggatta tcatcgtttg gcttatcaaa gtcctactaa cttgaccgcc    420
tatgtgggta caggcaacag caccagtatt gcggctaacc gtttatcata tctgtttgat    480
ttgcgtggcc ccagtttggc cgtagatacc gcttgctctt cttccctcgt cgccgttcac    540
ttggcctgtc agagtttgca aagtcaagaa tcgaacctct gcttagtggg gggagttaat    600
ctcattttgt cgccagagac aaccgttgtt ttttcccaag cgagaatgat cgcccccgac    660
agtcgttgta aaacctttga cgcgagggcc gatggttatg tgcgctcgga aggctgtgga    720
gtagtcgtac ttaaacgtct tagggatgcc attcaggacg gcgatcgcat tttagcagtg    780
attgaaggtt ccgcggtgaa tcaggatggt ttaagtaatg gactcacggc ccctaatggc    840
cctgctcaac aggcggtgat tcgtcaggcc ctggcaaatg cccaggtaaa accggcccag    900
attagctatg tcgaagccca tggcacgggg acagaattgg gggatccgat cgaagttaaa    960
tctctgaaag cggttttggg tgaaaagcga tcgctcgatc aaacctgttg gctcggttct   1020
gtgaaaacca acattggtca tttagaagcg gcggcgggaa tggcgggtct gattaaagtc   1080
```

```
gttctctgcc tacaacacca agaaattccc cctaatctcc actttcaaac ccttaatccc    1140
tatatttccc tagctgacac agcttttgcg attcccactc aggctcaacc ctggcggacc    1200
aaacccccta gtctggtgaa aacggtgtc gaacgacgtt tagcaggact cagttccttt     1260
gggtttgggg ggacaaattc ccatgtgatt ctc                                 1293
```

<210> SEQ ID NO 28
<211> LENGTH: 972
<212> TYPE: DNA
<213> ORGANISM: Microcystis aeruginosa

<400> SEQUENCE: 28

```
gtttttctat ttgccggtca aggttctcaa tatgtaggta tgggtcgtca actgtacgaa     60
acccaaccca tctttcgcca aaccttggat cgctgtgctg aaatcctgcg accccattta    120
gatcaacccc tcttagaaat tctttatcct gctgaccag aagccgaaac agcgagtttt    180
tacctagagc agactgccta tacccaaccc actttattcg cattcgagta tgccctagca    240
cagttatggc gttcctgggg aatagaaccg gcggcagtaa ttggtcacag tgtcggtgaa    300
tatgtggcgg ccaccgttgc cggagcctta agtctagaag aaggattaac gctaattgcc    360
aaacgggcaa aactgatgca gtctctcccc aagaatggga caatgatcgc cgttttttgcc   420 gcagaagagc gggttaaagc tgttattgag cctatagga ctgatgtagc gatcgctgct    480
gttaatggac cagaaaattt tgttatttca ggaaaagcgc cgattattgc tgagattatc    540
attcatttaa cggcagcagg aatagaagtt cgtcctctca agtttccca tgcttttcac    600 tcgcacctgt tggagccaat tttagattcc ttagaacagg aagctgctgc tatttcctac    660 caaccctgc aaattccctt agttgctaat ttaacggggg aagttctacc agaaggagca    720
acgattgagg ctcgttactg gcgaaatcat gcacgcaacc ctgtacaatt ttatgggagt    780
atccaaacgc tgatcgagca gaaattcagt ctttttttag aagttagccc taaaccgact    840
ttatctcgat tgggtcaaca atgttgtcca gaaagatcga ccacttggct attttcctc    900 gcccctcctc aagaagaaga acaaagccta ctaaatagtt tggcgattct ctatgattcc    960
caaggagccg aa                                                        972
```

<210> SEQ ID NO 29
<211> LENGTH: 204
<212> TYPE: DNA
<213> ORGANISM: Microcystis aeruginosa

<400> SEQUENCE: 29

```
atcacattgc aaaccctagt gggaaattta ctgcaattgt cccctgctga tgtcaatgtt     60
catacacctt tcctggagat gggggcagat tccattgtca tggttgaggc ggtcagacgg    120
attgagaata cctataacgt taaaattgct atgcgtcagt tatttgagga gttatctact    180
ttagatgctt tagctactta ttta                                           204
```

<210> SEQ ID NO 30
<211> LENGTH: 1182
<212> TYPE: DNA
<213> ORGANISM: Microcystis aeruginosa

<400> SEQUENCE: 30

```
aaagagatgc tttatcccat tgtggcccaa cgttctcaag atcaagaat ttgggatgtg       60 gacggtaatg aatatattga tatgacgatg gggcaagggg taacgctgtt tgggcatcaa    120
ccagacttca ttatgtcggc cctacaaagc caactcactg aaggcattca tctcaatccg    180
```

```
cgatcgccaa ttgtgggaga agtggccgcc ttaatttgtg aactaacagg agccgaacga    240
gcttgttttt gcaactctgg aaccgaagcc gtaatggccg ctattcgtat cgccagggca    300
acaacaggtc ggagtaaaat tgccctcttt gaaggctcct atcatggaca tgcggacgga    360
acccttttta ggaaccaaat tattgataac caactccact cttttcccct agctctaggc    420 gttccccccca gccttagttc cgatgtggtg gtattggact atggcagtgc ggaagctctg    480
aactatttac aaacccaggg gcaggattta gcggcggtct tagtagaacc aattcaaagt    540
ggcaatcctc tactccaacc ccaacaattt ctccaaagtc tgcgacaaat taccagtcaa    600
atgggcattg ccctgatttt tgatgaaatg attacgggtt ttcgatcgca cccagggga    660 gcgcaagctt tatttggagt acaggcggat attgccacct atggcaaagt agttgcggga    720
ggaatgccca ttggagttat tgcaggtaag gcccattatc tggacagcat tgacggggga    780
atgtggcgtt atggcgataa atcctatcct gggggtggaca gaaccttttt tgggggaacc    840
tttaatcagc atccgttagc aatggtagcg gctagggctg tcctgaccca tttaaaggag    900
caggggccag gtctgcaaca acaattaact gaacgcactg cggccttagc cgatacactg    960
aatcattatt ttcaagccga agaagttcct attaaaatcg aacagtttag ttctttcttc   1020
cggtttgccc tctctggcaa tttgatttta cttttctatc acatggtaga aaaaggtatt   1080
tatgtctggg aatggcgtaa acattttctt tcaaccgccc atacggaagc cgatcttgcc   1140
caatttgtcc aagcggttaa ggatagcatc acagaattgc gt                      1182
```

<210> SEQ ID NO 31
<211> LENGTH: 900
<212> TYPE: DNA
<213> ORGANISM: Microcystis aeruginosa

<400> SEQUENCE: 31

```
ggggggggatc aagtccctct caccgaagcc caacgacaac tgtggatttt ggctcaatta     60
ggagacaacg gctctgtggc ctataaccaa tcagtgacat tgcaattaag tggcccatta    120
aatcccgtcg caatgaatca agctattcaa caaatcagcg atcgccatga agcgttacga    180
accaaaatta atgcccaggg agatagtcaa gaaatcctgc cccaggtcga aattaactgc    240
cctatcttag acttcagtct tgaccaagct tcggcccaac agcaagcaga acaatggtta    300
aaggaagaaa gtgaaaaacc ctttgatttg agccagggtt ctctcgtgcg ttggcatcta    360
ctcaaattag aaccagaatt acatttgtta gtattaacgg cccatcacat tatcagtgac    420
ggttggtcaa tgggggtaat ccttcgggaa ttaggagagt tatattcagc caaatgtcag    480
ggtgttacgg ctaatcttaa aaccccaaaa cagtttcgag aattgattga atggcaaagc    540
cagccaagcc aaggggaaga actgaaaaaa cagcaagcct attggttagc aacccttgcc    600 gatcccctg ttttgaattt acccactgac aaacctcgtc cagctttacc cagttaccaa    660
gctaatcgtc gaagtctaac tttagatagc caatttacag aaaaactaaa gcaatttagt    720
cgtaaacagg gctgtacctt gctgatgacc ctgttatcgg tttataacat tctcgttcat    780
cgtttgacgg gacaggatga tattctggtg ggtctgccag cctctggacg ggggcttttta   840 gatagtgaag gtatggtggg ttattgcacc catttttttac caattcgcag tcaattagca    900
```

<210> SEQ ID NO 32
<211> LENGTH: 1290
<212> TYPE: DNA
<213> ORGANISM: Microcystis aeruginosa

<400> SEQUENCE: 32

```
acttacagtg aattaaattg tcgagccaat cagttagcac attatttaca aaaattagga      60
gttgggccag aggtcttagt cggtattttg gtcgaacgtt ctttagaaat gattgtcgga     120
ttgttaggga ttctcaaggc tgggggagcc tatgtacctc ttgatcctga ctatccccct    180
gaacgtcttc aatttatgtt agaagatagt caatttttc tcctcttaac ccaacagcat     240
ttactggaat cttttgctca gtcttcagaa acggctactc caagattat ttgtttggat     300
agcgactacc aaattatttc ccaggcaaag aatattaatc ccgaaaattc agtcacaacg    360
agtaatcttg cctatgtaat ttatacctct ggttcgacag gtaaaccgaa gggcgtgatg    420
aataatcatg ttgctattag taataaattg ttatgggtac aagacactta tcctctaacc    480
acagaagact gtatttttaca aaaaactccc tttagttttg atgtttcagt gtgggaatta   540
ttctggcccc tactaaacgg agcgcgtttg ttttttgcca agccgaatgg ccataaagat    600
gccagttact tagtcaatct gattcaagag caacaagtaa caacgctaca ttttgtgtct    660
tctatgctac agcttttct gacagaaaaa gacgtagaaa aatgtaatag tcttaaacga    720
gtcatttgta gtggtgaagc cctttctta gagcttcaag aacgtttttt tgctcgttta     780
gtctgtgaat tacacaatct ttatggaccg acagaagccg ctattcatgt cacattttgg    840
caatgtcaat cagatagcaa tttgaaaaca gtacccattg gtcggccgat cgctaatatc    900
caaatttaca ttttagactc tcatcttcag ccagtaccta ttggagtaat cggagaattg    960
cacattggtg gggttggttt ggcgcggggt tatttaaaca ggcctgagtt aacggcggag   1020
aaatttattg caaatccgtt tgcttccctt gatcccccccc taacccccct tgataagggg  1080
ggagatgaga gctataaaac ttttaaaaag ggggagagc aaccatcaag attgtataaa   1140
acgggagatt tagctcgtta tttacccgat ggcaagattg agtatctagg gcgcattgat   1200
aatcaggtaa aaattcgcgg tttccggatt gaattggggg aaattgaagc ggttttgcta  1260
tcccatcccc aggtacgaga agcggtcgtt                                   1290
```

<210> SEQ ID NO 33
<211> LENGTH: 195
<212> TYPE: DNA
<213> ORGANISM: Microcystis aeruginosa

<400> SEQUENCE: 33

```
gaggcgatcg ccgctatttt tggtcaagtt ttaaaactgg aaaaagtggg aatttatgat    60
aacttttttg agatcggcgg taattctttg caagccactc aagttattc acgcttacga   120
gaaagttttg ccctagagtt gcccttgcgt cgcctgtttg aacaaccgac tgtggcggat   180
ttggctttag ccgta                                                   195
```

<210> SEQ ID NO 34
<211> LENGTH: 900
<212> TYPE: DNA
<213> ORGANISM: Microcystis aeruginosa

<400> SEQUENCE: 34

```
cctcgtgatg gccaattacc cctctccttt gcccagtcgc gactctggtt cttgtatcaa     60
ttagaaggag ccacgggaac ctataacatg acagggcct tgagtttaag cgggcctctt   120
caggtcgaag ccctcaaaca agccctaaga actatcattc aacgccatga gccattgcgt   180
accagtttcc aatcggttga cggggttcca gtgcaggtga ttaatcccta tcctgtttgg   240
gaattagcga tggttgattt gacaggaaag gagacagaag cagaaaaatt ggcctatcag   300
```

```
gaatcccaaa ccccgtttga tttgaccaat agtcctttgt tgagggtaac gctcctcaaa      360
ttacagccag aaaagcatat tttattaatt aatatgcacc atattatttc cgatggctgg      420
tcaatcggtg ttttgttcg tgaattgtcc catctctata gggcttttgt ggcgggtaaa        480
gaaccaactt taccgatttt accaattcag tatgcggatt ttgccgtttg gcagcgagag      540
tggttacagg gtaaggtttt agcggctcaa ttgaatatt ggaagcgaca attggcagat        600
gctcctcctc tgctggaact gcccactgat cgccctcgtc ccgcaatcca aacctttcaa      660
ggcaagacag aaagatttga gctagatagg aaactgaccc aagaattaaa ggcattaagt      720
caacagtcgg gttgtacttt atttatgact tgttggccg cttttggggt ggttttatcc       780
cgttatagtg gccagactga tatcgtcatt ggttcggcga tcgccaaccg taatcgccaa      840
gacattgagg ggttaattgg ctttttttgtt aacactttgg cgttgaggtt agatttatca    900
```

<210> SEQ ID NO 35
<211> LENGTH: 1227
<212> TYPE: DNA
<213> ORGANISM: Microcystis aeruginosa

<400> SEQUENCE: 35

```
acctatggag aattaaacca tcgcgccaat caattagctc actatcttca gtcgttagga      60
gtcaccaaag aacaaatcgt cggggtttat ctggaacgtt cccttgaaat ggcgatcgga      120 ttttttaggta ttctcaaagc aggagccgcc tatctcccca ttgatcctga atatccctca    180
gtacgcaccc aatttattct cgaagatacc caactttcgc ttctcttaac tcaggcagaa    240
ctggcagaaa aactgcccca gactcaaaac aaaattatct gtctagatcg ggactggcca    300
gaaattacct cccaaccca gacaaaccta gacctaaaga tagaacctaa taacctagcc     360
tattgcatct atacttctgg ttccacagga caacccaaag gagtactgat ttcccatcaa    420
gccctactca acttaattt ctggcatcaa caagcgtttg agattggccc cttacataaa     480
gcgacccaag tggcaggcat tgctttcgat gcaacggttt gggaattgtg ccctatctg     540 accacaggag cctgtattaa tctggttccc caaaatattc tgctctcacc gacgatttta    600
cgggattggt tgcttaaccg agaaattacc atgagttttg tgccaactcc tttagctgaa    660
aaattattat cctggattg gcctaaccat tcttgtctaa aaaccctgtt actgggaggt     720
gacaaacttc atttttatcc tgctgcgtcc cttccctttc aggtcattaa caactatggc     780
ccaacggaaa atacagtggt tgcgacctct ggactggtca atcatcttc atctcatcac     840 tttggaactc cgactattgg tcgtcccatt gccaacgtcc aaatctattt attagaccaa    900
aacctacaac ctgtccccat tggtgtacca ggagaattac atttaggtgg ggcgggttta    960
gcgcagggct atctcaatcg tcctgagtta acggctgaaa aatttattgc caatcccttt    1020
gatccccccc taaccccct tgataagggg ggagaagaac cctcaaaact ctataaaacg    1080
ggagacttag cccgttattt acccgatggc aatgtagaat tttgggacg tattgacaat    1140 caggtaaaaaa ttcggggttt tcgcatcgaa actggggaaa tcgaagccgt tttaagtcaa    1200
tatttcctat tagctgaaag tgtagtc                                          1227
```

<210> SEQ ID NO 36
<211> LENGTH: 195
<212> TYPE: DNA
<213> ORGANISM: Microcystis aeruginosa

<400> SEQUENCE: 36

```
gctcaactga ctcaaatttg gagtgaagtt ttgggactgg aacgcattgg cgttaaggac      60
aacttttttg aattgggagg acattctctt ttggctaccc aggttttatc aagaattaat     120
tcagcctttg gacttgatct ttctgtgcaa attatgtttg aatcaccaac gatcgcgggc     180
attgcgggtt atatt                                                      195

<210> SEQ ID NO 37
<211> LENGTH: 915
<212> TYPE: DNA
<213> ORGANISM: Microcystis aeruginosa

<400> SEQUENCE: 37
gctagagacg gtcatttacc cctgtctttt gctcaacaac gtttatggtt tttacattat      60 cttccctg atagtcgttc ctacaatacc ctggaaatat tgcaaattga tgggaatctc     120
aatctgactg tgctagagca gagtttgggg gaattaatta accgccatga aattttaga     180 acaacattcc ccactgtttc aggggaaccg attcagaaaa ttgcacttcc tagtcgtttt     240
cagttaaaag ttgataatta tcaagattta gacgaaaatg aacaatcagc taaaattcaa     300
caagtagcag aattggaagc aggacaagct tttgatttaa cggtggggcc actgattcag     360
tttaagctat tgcaattgag tccccagaag tcggtgctgc tgttgaaaat gcaccatatt     420
atctatgatg gctggtcttt tgggattctg attcggggaat tatcggctct atacgaagca     480 ttttaaaga acttagccaa tcctctccct gcgttgtcta ttcagtatgc agattttgcg     540
gtttggcaac gtcaatatct ctcaggtgag gtcttagata acaactcaa ttattggcaa     600 gaacagttag caacagtctc tcctgttctt actttaccaa cggatagacc ccgtccggcg     660
atacaaactt tcagggagg agttgagcgt tttcaactgg atcaaaatgt cactcaaggt     720
cttaaaaagt taggtcaaga tcaggttgca accctgttta tgacgttgtt ggccggtttc     780
ggcgttttgc tatctcgtta tagtggtcaa tctgatctga tggtgggttc tccgatcgct     840
aatcgtaatc aagcagcgat cgaacccta attggctttt ttgctaacac tttggcttta     900
agaattaatt tatca                                                      915

<210> SEQ ID NO 38
<211> LENGTH: 1185
<212> TYPE: DNA
<213> ORGANISM: Microcystis aeruginosa

<400> SEQUENCE: 38
acatacactg aattaaacca tcgcgctaat cagttagccc attatttaca aactttaggc      60
gtgggagcag aagtcttagt cggtatttcc ctagaacgtt ctttagagat gattatcggc     120
ttattaggga ttctcaaggt aggtggtgct atcttcctc ttgatccaga ctatcccact     180
gagcgtcttc agttgatgtt agaagacagt caagttcctt ttttgattac ccacagttct     240
ttattagcaa aattgcctcc ctctcaagca actctgattt gtttagatca tatccaagag     300
cagatttctc aatattctcc agataatctt caatgtcagt taactcctgc caatttagct     360
aacgttattt atacctctgg ctctacgggt aagcctaaag gggtgatggt tgaacataaa     420
ggtttagtta acttagctct tgctcaaatt caatcttttg cagtcaacca taacagtcgt     480
gtgctgcaat tgcttctttt tagttttgat gcttgtattt cagaaatttt gatgaccttt     540
ggttctggag cgacgcttta tcttgcacaa aaagatgctt tattgccagg tcagccatta     600
attgaacggt tagtaaagaa tggaattact catgtgactt tgccgccttc agctttagtg     660
gttttacccc aggaaccgtt acgcaactta gaaaccttaa ttgtggcggg tgaggcttgt     720
```

```
tctcttgatt tagtgaaaca atggtcaatc gatagaaact tttcaatgc ctatgggcca    780 acggaagcga gtgtttgtgc cactattgga caatgttatc aagatgattt aaaggtgacg    840
attggtaagg cgatcgccaa tgtccaaatt tatattttag atgccttttt acagccggtg    900 ccgtgggag tgtcaggaga gttatacatt ggtggagttg gggtggcaag gggctattta    960
aatcgtcctg aattaaccca agaaaaattt attgctaatc cttttagtaa cgacccagat   1020
tctcggctct ataaaactgg cgacttagcg cgttatttac ccgatggtaa tattgaatat   1080
ttaggacgca ttgacaatca ggtaaaaatt cgcggttttc gcattgagtt aggagaaatt   1140
gaagcggttc tgagtcaatg tcccgatgtg caaaatacgg cggtg                   1185
```

<210> SEQ ID NO 39
<211> LENGTH: 195
<212> TYPE: DNA
<213> ORGANISM: Microcystis aeruginosa

<400> SEQUENCE: 39

```
gaaattctgg ctcaaatatg ggggcaagtt ctcaagatag aaagagtcag cagagaagat     60
aatttctttg aattgggggg gcattccctt ttagctaccc aggtaatgtc ccgtctgcgt    120 gaaactttc aagtcgaatt acctttgcgt agtctcttta ccgctcccac tattgctgaa    180
ttggccctaa caatt                                                     195
```

<210> SEQ ID NO 40
<211> LENGTH: 897
<212> TYPE: DNA
<213> ORGANISM: Microcystis aeruginosa

<400> SEQUENCE: 40

```
aacgacagtg ctaacctccc gttatctttt gctcaacaac gtttatggtt tctggatcaa     60
ttagaaccta acagcgcctt ttatcatgta gggggagccg taagactaga aggaacatta    120
aatattactg ccttagagca aagcttaaaa gaaattatta atcgtcatga agctttacgc    180
acaaatttta taacgattga tggtcaagcc actcaaatta ttcaccctac tattaattgg    240
cgattgtctg ttgttgattg tcaaaattta accgacactc aatctctgga aattgcggaa    300
gctgaaaagc cctttaatct tgctcaagat tgcttatttc gtgctacttt attcgtgcga    360
tcaccgctag aatatcatct actcgtgacc atgcaccata ttgttagcga tggctggtca    420
attggagtat tttttcaaga actaactcat ctttacgctg tctataatca gggtttaccc    480
tcatctttaa cgcctattaa atacaatat gctgattttg cggtctggca acggaattgg    540
ttacaaggtg aaattttaag taatcaattg aattattggc gcgaacaatt agcaaatgct    600
cctgcttttt tacctttacc gacagataga cctaggcccg caatccaaac ttttattggt    660
tctcatcaag aatttaaact ttctcagcca ttaagccaaa aattgaatca actaagtcag    720
aagcatggag tgactttatt tatgactctc ctggctgctt ttgctaccctt actttaccgt    780 tatacaggac aagcagatat tttagttggt tctcctattg ctaaccgtaa tcgtaaggaa    840
attgagggat taatcggctt ttttgttaat acattagttc tgagattgag tttagat       897
```

<210> SEQ ID NO 41
<211> LENGTH: 1245
<212> TYPE: DNA
<213> ORGANISM: Microcystis aeruginosa

<400> SEQUENCE: 41

```
acctatgctg aattaaatca tcaagctaat cagttagtcc attacttaca aactttagga      60
attgggccag aggtcttagt cgctatttca gtagaacgtt ctttagaaat gattatcggc     120
ttattagcca ttctcaaggc gtgtggtgct tatctccctc ttgctcctga ctatcccact     180
gagcgtcttc agttcatgtt agaagatagt caagcttctt ttttgattac ccacagttct     240
ttattagaaa aattgccttc ttctcaagcg actctaattt gtttagatca catccaagag     300
cagatttctc aatattctcc cgataatctt caaagtgagt taactccttc caatttggct     360
aacgttattt acacctctgg ctctacgggt aagcctaaag gggtgatggt tgaacatcgg     420
ggcttagtta acttagcgag ttctcaaatt caatcttttg cagtcaaaaa taacagtcgt     480
gtactgcaat ttgcttcctt tagttttgat gcttgtattt cagaaatttt gatgaccttt     540
ggttctggag cgactcttta tcttgctcaa aaaatgatt tattgccagg tcagccatta     600
atggaaaggt tagaaaagaa taaaattacc catgttactt taccccttc agctttagct     660 gttttaccaa aaaaccgtt acccaactta caaactttaa ttgtggcggg tgaggcttgt     720
cctctggatt tagtcaaaca atggtcagtc ggtagaaact ttttcaatgc ctatggcccg     780
acagaaacga gtgtttgtgc cacgattgga caatgttatc aagatgattt aaaggtcacg     840
attggtaagg cgatcgctaa tgtccaaatt tatattttgg atgccttttt acaaccagta     900
cccatcggag taccagggga attatacatt ggtggagtcg gagttgcgag gggttatcta     960
aatcgtcctg aattaacggc ggaaagattt attcctaatc cttttgatcc ccccctaacc    1020 cccttaaaa aggggggaga taagagctat gaaactttta aaaggggga agagcaacca    1080 tcaaaactct ataaaacggg agatttagct cgttatttac ccgatggcaa tattgaatat    1140
ttaggacgca ttgacaatca ggtaaaaatt cgcggttttc gcattgagtt aggagaaatt    1200
gaagcggttc tgagtcaatg tcccgatgtg caaaatacgg cggtg                    1245
```

<210> SEQ ID NO 42
<211> LENGTH: 196
<212> TYPE: DNA
<213> ORGANISM: Microcystis aeruginosa

<400> SEQUENCE: 42

```
ttacaattag ctcaaatctg gtcagagatt ttaggcatta ataatattgg tattcaggaa      60
aacttctttg aattaggcgg tcattcttta ttagcagtca gtctgatcaa tcgtattgaa     120
caaaagttag ataaacgttt accattaacc agtcttttc aaaatggaac catagcaagt     180
ctagctcaat tactag                                                     196
```

<210> SEQ ID NO 43
<211> LENGTH: 681
<212> TYPE: DNA
<213> ORGANISM: Microcystis aeruginosa

<400> SEQUENCE: 43

```
actccatttt ttgctgttca tcccattggt ggtaatgtgc tatgttatgc cgatttagct      60
cgtaatttag gaacgaaaca gccgttttat ggattacaat cattagggct aagtgaatta     120
gaaaaaactg tagcctctat tgaagaaatg gcgatgattt atattgaagc aatacaaact     180
gttcaagcct ctggtcccta ctatttagga ggttggtcaa tgggaggagt gatagctttt     240
gaaatcgccc aacaattatt gacccaaggt caagaagttg ctttactggc tttaatagat     300
agttattctc ccagtttact taattcagtt aataggagaa aaattctgc taattccctg     360 acagaagaat ttaatgaaga tatcaatatt gcctattctt tcatcagaga cttagcaagt     420
```

```
atatttaatc aagaaatctc tttctctggg agtgaacttg ctcattttac atcagacgaa    480
ttactagaca agtttattac ttggagtcaa gagacgaatc ttttgccgtc agattttggg    540
aagcagcagg ttaaaacctg gtttaaagtt ttccagatta atcaccaagc ttgagcagc     600 tattctccca agacgtatct gggtagaagt gttttcttag gagcggaaga cagttctatt    660
aaaaatcctg gttggcatca a                                              681
```

<210> SEQ ID NO 44
<211> LENGTH: 1065
<212> TYPE: DNA
<213> ORGANISM: Microcystis aeruginosa

<400> SEQUENCE: 44

```
agcgggtctc aagaccaaaa aacgatacag tttagcctct actactttgg tagctatgaa    60
gcggaattta acccgaataa atataactta ctgtttgaag gagctaaatt tggcgatcgc    120
gctggtttta cggcccttttg gattcctgaa cgtcatttcc acgcttttgg tggttttttct   180 cccaatcctt cggttttggc ggcggcttta gcacgggaaa ccaaacagat tcaactgcga    240
tcaggcagtg tggtttttacc gctacataat tccatccgag tcgccgaaga atgggcagtg    300
gtggacaatc tttcccaggg ccgcgttggt attgcttttg catcggggttg gcatccccag    360 gattttgtct tggctcccca gtcctttggc caacatcggg aattgatgtt ccaagaaatt    420
gaaaccgtcc agaaactttg gcgagggaa gcgatcaccg tgccagacgg aaagggtcaa    480
agggtagagg ttaaaaccta tccccaaccg atgcagtccc agttacccag ctggattact    540
attgtcaata atcccgatac ctatatcaga gcaggggcga tcggtgctaa tatccttacc    600
aatctgatgg ggcaaagcgt ggaagattta gcccgtaata ttgcgctata tcgtcaatct    660
ttggcagagc atggttatga tcccgcgtcg ggaacggtga cagttctcct gcatactttt    720
gttggcaagg atttagaaca agttcgagaa caggctcgcc aacccctttgg gcaatacctc    780 acctcctctg tcggactctt gcagaacatg gtcaagagcc agggcatgaa agtggatttt    840
gaacaattaa gagacgaaga tcgggacttt ctcctcgctt ctgcctataa acgctataca    900
gaaaccagtg ctttaattgg cacacccgaa tcctgtcgtc aaattattga tcatttgcag    960
tccatcggtg tggatgaagt ggcttgttttt attgattttg gggtagatga acaaacagtt    1020
ttggccaatt taccctatct ccagtcccta aaagacttat atcaa                    1065
```

<210> SEQ ID NO 45
<211> LENGTH: 99
<212> TYPE: DNA
<213> ORGANISM: Microcystis aeruginosa

<400> SEQUENCE: 45

```
attgatcccc ccctaacccc ccttgataag gggattgatc ccccccctaac ccccctttgat   60 aaggggattg atcccccccct aacccccctt gataagggg                           99
```

<210> SEQ ID NO 46
<211> LENGTH: 231
<212> TYPE: DNA
<213> ORGANISM: Microcystis aeruginosa

<400> SEQUENCE: 46

```
ccttatcaag gggggttagg gggggatcaa tccccttatc aagggggggtt agggggggat    60 caatccccctt atcaagggg gttaggggggt gatcaatccc cttatcaagg ggggttaggg   120
```

```
ggtgatcaat cccttatca agggggtta gggggggatc aatcccctta tcaaggagag      180 ttagggggg atcaatcccc ttatcaaggg gggttagggg gggatcaagt c              231

<210> SEQ ID NO 47
<211> LENGTH: 1146
<212> TYPE: DNA
<213> ORGANISM: Microcystis aeruginosa

<400> SEQUENCE: 47
cctgcttcag aaatgcgaga gtgggtcgaa aacactgtta gtcgcatctt ggctttccaa     60
ccagaacgcg gtttagaaat tggttgtggt acaggtttgt tactctccag ggtagcaaag    120
cattgtcttg aatattgggc aacggattat tcccaagggg cgatccagta tgttgaacgg    180
gtttgcaatg ccgttgaagg tttagaacag gttaaattac gctgtcaaat ggcagataat    240
tttgaaggta ttgccctaca tcaatttgat accgtcgtct taaattcgat tattcagtat    300
tttcccagtg tggattatct gttacaggtg cttgaagggg cgatcaacgt cattggcgag    360
cgaggtcaga ttttgtcgg ggatgtgcgg agtttacccc tattagagcc atatcatgcg    420
gctgtgcaat tagcccaagc ttctgactcg aaaactgttg aacaatggca acaacaggtg    480
cgtcaaagtg tagcaggtga agaagaactg gtcattgatc ccacattgtt cctggcttta    540
aaacaacatt ttccgcaaat tagctgggta gaaattcaac cgaaacgggg tgtggctcac    600
aatgagttaa ctcaatttcg ctatgatgtc actctccatt tagagactat caataatcaa    660
gcattattga gcggcaatcc aacggtaatt acctggttaa attggcaact tgaccaactg    720
tctttaacac aaattaaaga taaattatta acagacaaac ctgaattgtg gggaattcgt    780
ggtattccta atcagcgagt tgaagaggct ctaaaaattt gggaatgggt ggaaaatgcc    840
cctgatgttg aaacggttga acaactcaaa aaacttctca acaacaagt agatactggt    900 attaatcctg aacaggttg gcaattagct gagtctctcg gttacaccgc tcaccttagt    960
tggtgggaaa gtagtcaaga cggttccttt gatgtcattt ttcagcggaa ttcagaagcg   1020
gaggactcaa aaaaattaac cctttcaaaa cttgctttct gggatgaaaa acccttaaa   1080 ataaagccct ggagtgacta tactaacaac cctctgcgcg gtaagttagt ccaaaaatta   1140
attcct                                                             1146

<210> SEQ ID NO 48
<211> LENGTH: 813
<212> TYPE: DNA
<213> ORGANISM: Microcystis aeruginosa

<400> SEQUENCE: 48
atgacaaatt atggcaaatc tatgtctcat tactatgatc tagtggtagg acataaaggt    60
tataacaaag attacgccac tgaagtagaa ttcattcaca atttagttga gacttacaca   120
actgaagcca atctatcct atacttgggc tgtggtacgg gttatcatgc cgctctttta   180
gcacagaaag ggtattctgt acatggtgtt gatctcagtg ctgaaatgtt agagcaggct   240
aaaactcgca ttgaagatga aacaatagct tctaatctga gttttctca aggaaatatt   300 tgtgaaatcc gtttaaatcg tcagtttaat gttgttcttg ctctatttca tgtggttaac   360
tatcaaacga ccaatcaaaa tttactggca acgtttgcaa cggttaaaaa ccatttaaaa   420
gctgggggga tttttatttg tgatgtgtcc tatgggtctt acgtactggg ggaatttaag   480
agtcggccta cggcatcaat attgcgttta gaggataatt ccaatggtaa cgaagtaacc   540
tatattagtg aactaaattt tttaacccat gaaaatatag tggaagttac tcacaattta   600
```

```
tgggtaacaa atcaagaaaa tcaacttcta gagaattcac gggaaacaca tcttcagcgc      660
tatcttttca agcctgaagt tgaattgttg gctgatgctt gtgaactaac tgttcttgat      720
gcgatgccct ggcttgaaca acgtcctttg acaaacattc cttgtccttc agtttgtttt      780
gttattgggc ataaaacaac ccattcagct taa                                  813
```

```
<210> SEQ ID NO 49
<211> LENGTH: 21
<212> TYPE: DNA
<213> ORGANISM: Artificial Sequence
<220> FEATURE:
<223> OTHER INFORMATION: oligonucleotide primer with homology to
      Microcystis aeruginosa

<400> SEQUENCE: 49
ccgacctgtg ataaacaatt c                                               21

<210> SEQ ID NO 50
<211> LENGTH: 20
<212> TYPE: DNA
<213> ORGANISM: Artificial Sequence
<220> FEATURE:
<223> OTHER INFORMATION: oligonucleotide primer with homology to
      Microcystis aeruginosa
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 50
cknccdgtda traanarytc                                                 20

<210> SEQ ID NO 51
<211> LENGTH: 18
<212> TYPE: DNA
<213> ORGANISM: Artificial Sequence
<220> FEATURE:
<223> OTHER INFORMATION: oligonucleotide primer with homology to
      Microcystis aeruginosa

<400> SEQUENCE: 51
ttcaatatcc tggggata                                                   18

<210> SEQ ID NO 52
<211> LENGTH: 18
<212> TYPE: DNA
<213> ORGANISM: Artificial Sequence
<220> FEATURE:
<223> OTHER INFORMATION: oligonucleotide primer with homology to
      Microcystis aeruginosa
<220> FEATURE:
<221> NAME/KEY: misc_feature
<222> LOCATION: (13)..(13)
<223> OTHER INFORMATION: n is a, c, g, or t

<400> SEQUENCE: 52
ytcdatrtcy tgnggrta                                                   18

<210> SEQ ID NO 53
<211> LENGTH: 21
<212> TYPE: DNA
<213> ORGANISM: Artificial Sequence
<220> FEATURE:
```

```
<223> OTHER INFORMATION: oligonucleotide primer with homology to
      Microcystis aeruginosa

<400> SEQUENCE: 53
cgttggttac aggccctttc t                                              21

<210> SEQ ID NO 54
<211> LENGTH: 20
<212> TYPE: DNA
<213> ORGANISM: Artificial Sequence
<220> FEATURE:
<223> OTHER INFORMATION: oligonucleotide primer with homology to
      Microcystis aeruginosa
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 54
mgntggytnc argcnytnws                                                20

<210> SEQ ID NO 55
<211> LENGTH: 18
<212> TYPE: DNA
<213> ORGANISM: Artificial Sequence
<220> FEATURE:
<223> OTHER INFORMATION: oligonucleotide primer with homology to
      Microcystis aeruginosa

<400> SEQUENCE: 55
ttagacttaa gccattgg                                                  18

<210> SEQ ID NO 56
<211> LENGTH: 18
<212> TYPE: DNA
<213> ORGANISM: Artificial Sequence
<220> FEATURE:
<223> OTHER INFORMATION: oligonucleotide primer with homology to
      Microcystis aeruginosa
<220> FEATURE:
<221> NAME/KEY: misc_feature
<222> LOCATION: (1)..(1)
<223> OTHER INFORMATION: y is t/u or c
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: y is t/u or c
<220> FEATURE:
<221> NAME/KEY: misc_feature
<222> LOCATION: (7)..(7)
<223> OTHER INFORMATION: y is t/u or c
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
```

-continued

```
<222> LOCATION: (10)..(10)
<223> OTHER INFORMATION: w is a or t/u
<220> FEATURE:
<221> NAME/KEY: misc_feature
<222> LOCATION: (11)..(11)
<223> OTHER INFORMATION: s is g or c
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: y is t/u or c
<400> SEQUENCE: 56
ytngayytnw sncaytgg 18

<210> SEQ ID NO 57
<211> LENGTH: 24
<212> TYPE: DNA
<213> ORGANISM: Artificial Sequence
<220> FEATURE:
<223> OTHER INFORMATION: oligonucleotide primer with homology to Microcystis aeruginosa
<400> SEQUENCE: 57
catagaagaa tcgagaccat attc 24

<210> SEQ ID NO 58
<211> LENGTH: 24
<212> TYPE: DNA
<213> ORGANISM: Artificial Sequence
<220> FEATURE:
<223> OTHER INFORMATION: oligonucleotide primer with homology to Microcystis aeruginosa
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (5)..(5)
<223> OTHER INFORMATION: s is g or c
<220> FEATURE:
<221> NAME/KEY: misc_feature
<222> LOCATION: (6)..(6)
<223> OTHER INFORMATION: w is a or t/u
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (8)..(8)
<223> OTHER INFORMATION: s is  g or c
<220> FEATURE:
<221> NAME/KEY: misc_feature
<222> LOCATION: (9)..(9)
<223> OTHER INFORMATION: w is a or t/u
<220> FEATURE:
<221> NAME/KEY: misc_feature
<222> LOCATION: (10)..(10)
<223> OTHER INFORMATION: r is g or a
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (15)..(15)
<223> OTHER INFORMATION: r is g or a
<220> FEATURE:
<221> NAME/KEY: misc_feature
<222> LOCATION: (16)..(16)

<223> OTHER INFORMATION: n is a, c, g, or t
<220> FEATURE:
<221> NAME/KEY: misc_feature
<222> LOCATION: (19)..(19)
<223> OTHER INFORMATION: r is g or a
<220> FEATURE:
<221> NAME/KEY: misc_feature
<222> LOCATION: (22)..(22)
<223> OTHER INFORMATION: y is t/u or c

<400> SEQUENCE: 58
catnswnswr tcnarnccrt aytc        24

<210> SEQ ID NO 59
<211> LENGTH: 666
<212> TYPE: PRT
<213> ORGANISM: Microcystis aeruginosa

<400> SEQUENCE: 59

```
Met Thr Thr Gln Thr Ala Ser Ser Ala Asn Ala Leu Ala Ser Phe Asn
1               5                   10                  15

Gln Phe Leu Arg Asp Val Lys Ala Ile Ala Gln Pro Tyr Trp Tyr Pro
            20                  25                  30

Thr Val Ser Asn Lys Arg Ser Phe Ser Glu Val Ile Arg Ser Trp Gly
        35                  40                  45

Met Leu Ser Leu Leu Ile Phe Leu Ile Val Gly Leu Val Ala Val Thr
    50                  55                  60

Ala Phe Asn Ser Phe Val Asn Arg Arg Leu Ile Asp Val Ile Ile Gln
65                  70                  75                  80

Glu Lys Asp Ala Ser Gln Phe Ala Ser Thr Leu Thr Val Tyr Ala Ile
                85                  90                  95

Gly Leu Ile Cys Val Thr Leu Leu Ala Gly Phe Thr Lys Asp Ile Arg
            100                 105                 110

Lys Lys Ile Ala Leu Asp Trp Tyr Gln Trp Leu Asn Thr Gln Ile Val
        115                 120                 125

Glu Lys Tyr Phe Ser Asn Arg Ala Tyr Tyr Lys Ile Asn Phe Gln Ser
    130                 135                 140

Asp Ile Asp Asn Pro Asp Gln Arg Leu Ala Gln Glu Ile Glu Pro Ile
145                 150                 155                 160

Ala Thr Asn Ala Ile Ser Phe Ser Ala Thr Phe Leu Glu Lys Ser Leu
                165                 170                 175

Glu Met Leu Thr Phe Leu Val Val Trp Ser Ile Ser Arg Gln Ile
            180                 185                 190

Ala Ile Pro Leu Met Phe Tyr Thr Ile Ile Gly Asn Phe Ile Ala Ala
        195                 200                 205

Tyr Leu Asn Gln Glu Leu Ser Lys Ile Asn Gln Ala Gln Leu Gln Ser
    210                 215                 220

Lys Ala Asp Tyr Asn Tyr Ala Leu Thr His Val Arg Thr His Ala Glu
225                 230                 235                 240

Ser Ile Ala Phe Phe Arg Gly Glu Lys Glu Glu Gln Asn Ile Ile Gln
                245                 250                 255

Arg Arg Phe Gln Glu Val Ile Asn Asp Thr Lys Asn Lys Ile Asn Trp
            260                 265                 270

Glu Lys Gly Asn Glu Ile Phe Ser Arg Gly Tyr Arg Ser Val Ile Gln
        275                 280                 285

Phe Phe Pro Phe Leu Val Leu Gly Pro Leu Tyr Ile Lys Gly Glu Ile
    290                 295                 300
```

| | | | | | | | | | | | | | | | |
|---|---|---|---|---|---|---|---|---|---|---|---|---|---|---|---|
|Asp|Tyr|Gly|Gln|Val|Glu|Gln|Ala|Ser|Leu|Ala|Ser|Phe|Met|Phe|Ala|
|305| | | |310| | | |315| | | |  | | |320|

| | | | | | | | | | | | | | | | |
|---|---|---|---|---|---|---|---|---|---|---|---|---|---|---|---|
|Ser|Ala|Leu|Gly|Glu|Leu|Ile|Thr|Glu|Phe|Gly|Thr|Ser|Gly|Arg|Phe|
| | | | |325| | | |330| | | |335| | | |

| | | | | | | | | | | | | | | | |
|---|---|---|---|---|---|---|---|---|---|---|---|---|---|---|---|
|Ser|Ser|Tyr|Val|Glu|Arg|Leu|Asn|Glu|Phe|Ser|Asn|Ala|Leu|Glu|Thr|
| | | |340| | | | |345| | | |350| | | |

| | | | | | | | | | | | | | | | |
|---|---|---|---|---|---|---|---|---|---|---|---|---|---|---|---|
|Val|Thr|Lys|Gln|Ala|Glu|Asn|Val|Ser|Thr|Ile|Thr|Ile|Glu|Glu| |
| | |355| | | | |360| | | | |365| | | |

| | | | | | | | | | | | | | | | |
|---|---|---|---|---|---|---|---|---|---|---|---|---|---|---|---|
|Asn|His|Phe|Ala|Phe|Glu|His|Val|Thr|Leu|Glu|Thr|Pro|Asp|Tyr|Glu|
| |370| | | | |375| | | | |380| | | | |

| | | | | | | | | | | | | | | | |
|---|---|---|---|---|---|---|---|---|---|---|---|---|---|---|---|
|Lys|Val|Ile|Val|Glu|Asp|Leu|Ser|Leu|Thr|Val|Gln|Lys|Gly|Glu|Gly|
|385| | | | |390| | | | |395| | | | |400|

| | | | | | | | | | | | | | | | |
|---|---|---|---|---|---|---|---|---|---|---|---|---|---|---|---|
|Leu|Leu|Ile|Val|Gly|Pro|Ser|Arg|Gly|Lys|Ser|Ser|Leu|Leu|Arg| |
| | | | |405| | | | |410| | | | |415| |

| | | | | | | | | | | | | | | | |
|---|---|---|---|---|---|---|---|---|---|---|---|---|---|---|---|
|Ala|Ile|Ala|Gly|Leu|Trp|Asn|Ala|Gly|Thr|Gly|Arg|Leu|Val|Arg|Pro|
| | | |420| | | | |425| | | | |430| | |

| | | | | | | | | | | | | | | | |
|---|---|---|---|---|---|---|---|---|---|---|---|---|---|---|---|
|Pro|Leu|Glu|Glu|Ile|Leu|Phe|Leu|Pro|Gln|Arg|Pro|Tyr|Ile|Ile|Leu|
| | |435| | | | |440| | | | |445| | | |

| | | | | | | | | | | | | | | | |
|---|---|---|---|---|---|---|---|---|---|---|---|---|---|---|---|
|Gly|Thr|Leu|Arg|Glu|Gln|Leu|Leu|Tyr|Pro|Leu|Thr|Asn|Ser|Glu|Met|
| |450| | | | |455| | | | |460| | | | |

| | | | | | | | | | | | | | | | |
|---|---|---|---|---|---|---|---|---|---|---|---|---|---|---|---|
|Ser|Asn|Thr|Glu|Leu|Gln|Ala|Val|Leu|Gln|Gln|Val|Asn|Leu|Gln|Asn|
|465| | | | |470| | | | |475| | | | |480|

| | | | | | | | | | | | | | | | |
|---|---|---|---|---|---|---|---|---|---|---|---|---|---|---|---|
|Val|Leu|Asn|Arg|Val|Asp|Asp|Phe|Asp|Ser|Glu|Lys|Pro|Trp|Glu|Asn|
| | | | |485| | | | |490| | | | |495| |

| | | | | | | | | | | | | | | | |
|---|---|---|---|---|---|---|---|---|---|---|---|---|---|---|---|
|Ile|Leu|Ser|Leu|Gly|Glu|Gln|Gln|Arg|Leu|Ala|Phe|Ala|Arg|Leu|Leu|
| | | |500| | | | |505| | | | |510| | |

| | | | | | | | | | | | | | | | |
|---|---|---|---|---|---|---|---|---|---|---|---|---|---|---|---|
|Val|Asn|Ser|Pro|Ser|Phe|Thr|Ile|Leu|Asp|Glu|Ala|Thr|Ser|Ala|Leu|
| | |515| | | | |520| | | | |525| | | |

| | | | | | | | | | | | | | | | |
|---|---|---|---|---|---|---|---|---|---|---|---|---|---|---|---|
|Asp|Leu|Thr|Asn|Glu|Gly|Ile|Leu|Tyr|Glu|Gln|Leu|Gln|Thr|Arg|Lys|
| |530| | | | |535| | | | |540| | | | |

| | | | | | | | | | | | | | | | |
|---|---|---|---|---|---|---|---|---|---|---|---|---|---|---|---|
|Thr|Thr|Phe|Ile|Ser|Val|Gly|His|Arg|Glu|Ser|Leu|Phe|Asn|Tyr|His|
|545| | | | |550| | | | |555| | | | |560|

| | | | | | | | | | | | | | | | |
|---|---|---|---|---|---|---|---|---|---|---|---|---|---|---|---|
|Gln|Trp|Val|Leu|Glu|Leu|Ser|Ala|Asp|Ser|Ser|Trp|Glu|Leu|Leu|Ser|
| | | | |565| | | | |570| | | | |575| |

| | | | | | | | | | | | | | | | |
|---|---|---|---|---|---|---|---|---|---|---|---|---|---|---|---|
|Val|Gln|Asp|Tyr|Arg|Leu|Lys|Lys|Ala|Gly|Glu|Met|Phe|Thr|Asn|Ala|
| | | |580| | | | |585| | | | |590| | |

| | | | | | | | | | | | | | | | |
|---|---|---|---|---|---|---|---|---|---|---|---|---|---|---|---|
|Ser|Ser|Asn|Asn|Ser|Ile|Thr|Pro|Asp|Ile|Thr|Ile|Asp|Asn|Gly|Ser|
| | |595| | | | |600| | | | |605| | | |

| | | | | | | | | | | | | | | | |
|---|---|---|---|---|---|---|---|---|---|---|---|---|---|---|---|
|Glu|Pro|Glu|Ile|Val|Tyr|Ser|Leu|Glu|Gly|Phe|Ser|His|Gln|Glu|Met|
| |610| | | | |615| | | | |620| | | | |

| | | | | | | | | | | | | | | | |
|---|---|---|---|---|---|---|---|---|---|---|---|---|---|---|---|
|Lys|Leu|Leu|Thr|Asp|Leu|Ser|Leu|Ser|Ser|Ile|Arg|Ser|Lys|Ala|Ser|
|625| | | | |630| | | | |635| | | | |640|

| | | | | | | | | | | | | | | | |
|---|---|---|---|---|---|---|---|---|---|---|---|---|---|---|---|
|Arg|Gly|Lys|Val|Ile|Thr|Ala|Lys|Asp|Gly|Phe|Thr|Tyr|Leu|Tyr|Asp|
| | | | |645| | | | |650| | | | |655| |

| | | | | | | | |
|---|---|---|---|---|---|---|---|
|Lys|Asn|Pro|Gln|Ile|Leu|Lys|Trp|Leu|Arg|
| | | |660| | | | |665| |

<210> SEQ ID NO 60
<211> LENGTH: 2004
<212> TYPE: DNA
<213> ORGANISM: Microcystis aeruginosa

<400> SEQUENCE: 60

```
atgacaaccc aaacagcttc tagtgccaat gcccttgctt cctttaacca attttttaagg    60
```

| | |
|---|---|
| gatgtaaagg cgatcgccca accctattgg tatcccactg tatcaaataa aagaagcttt | 120 |
| tctgaggtta ttcgttcctg gggaatgcta tcactgctta tcttttgat tgtgggatta | 180 |
| gtcgccgtca cggcttttaa tagttttgtt aatcgtcgtt taattgatgt cattattcaa | 240 |
| gaaaaagatg cgtctcaatt tgccagtaca ttaactgtct atgcgatcgg attaatctgt | 300 |
| gtaacgctgc tggcagggtt cactaaagat attcgcaaaa aaattgccct agattggtat | 360 |
| caatggttaa acacccagat tgtagagaaa tattttagta atcgtgccta ttataaaatt | 420 |
| aactttcaat ctgacattga taaccccgat caacgtctag cccaggaaat tgaaccgatc | 480 |
| gccacaaacg ccattagttt ctcggccact tttttggaaa aagtttgga atgctaact | 540 |
| ttttagtgg tagtttggtc aatttctcga cagattgcta ttccgctaat gttttacacg | 600 |
| attatcggta attttattgc cgcctatcta aatcaagaat taagcaagat caatcaggca | 660 |
| caactgcaat caaaagcaga ttataactat gccttaaccc atgttcggac tcatgcggaa | 720 |
| tctattgctt ttttcgggg agaaaaagag aacaaaata ttattcagcg acgttttcag | 780 |
| gaagttatca atgatacgaa aaataaaatt aactgggaaa aagggaatga aattttagt | 840 |
| cggggctatc gttccgtcat tcagtttttt ccttttttag tccttggccc tttgtatatt | 900 |
| aaaggagaaa ttgattatgg acaagttgag caagcttcat tagctagttt tatgtttgca | 960 |
| tcggccctgg gagaattaat tacagaattt ggtacttcag acgtttttc tagttatgta | 1020 |
| gaacgtttaa atgaatttc taatgcctta gaaactgtga ctaaacaagc cgagaatgtc | 1080 |
| agcacaatta caaccataga agaaaatcat tttgcctttg aacacgtcac cctagaaacc | 1140 |
| cctgactatg aaaaggtgat tgttgaggat ttatctctta ctgttcaaaa aggtgaagga | 1200 |
| ttattgatt tcgggcccag tggtcgaggt aaaagttctt tattaagggc gatcgccggt | 1260 |
| ttatggaatg ctggcactgg gcgtttagtg cgtcctcccc tagaagaaat tctcttttg | 1320 |
| ccccaacgtc cctacattat tttgggaacc ttacgcgaac aattgctgta tcctctaacc | 1380 |
| aatagtgaga tgagcaatac cgaacttcaa gcagtattac aacaagtcaa tttgcaaaat | 1440 |
| gtgctaaatc gggtggatga ctttgactcc gaaaaaccct gggaaaacat tctctcccc | 1500 |
| ggtgaacaac aacgcctagc ctttgctcga ttgttagtga attctccgag ttttaccatt | 1560 |
| ttagatgagg cgaccagtgc cttagattta acaaatgagg ggattttata cgagcaatta | 1620 |
| caaactcgca agacaacctt tattagtgtg ggtcatcgag aaagtttgtt taattaccat | 1680 |
| caatgggttt tagaactttc tgctgactct agttgggaac tcttaagcgt tcaagattat | 1740 |
| cgccttaaaa agcgggaga aatgtttact aatgcttcga gtaacaattc cataacaccc | 1800 |
| gatattacta tcgataatgg atcagaacca gaaatagtct attctcttga aggattttcc | 1860 |
| catcaggaaa tgaaactatt aacagaccta tcactctcta gcattcggag taaagccagt | 1920 |
| cgagggaagg tgattacagc caaggatggt tttacctacc tttatgacaa aaatcctcag | 1980 |
| atattaaagt ggctcagaac ttaa | 2004 |

<210> SEQ ID NO 61
<211> LENGTH: 27260
<212> TYPE: DNA
<213> ORGANISM: Microcystis aeruginosa

<400> SEQUENCE: 61

| | |
|---|---|
| atgactatta actatggtga tctgcaagaa ccctttaata aattctcaac cctagttgaa | 60 |
| ttactccgtt atcgggcaag cagtcaaccg gaacgcctcg cctatatttt tctgcgagac | 120 |
| ggagaaatcg aagaagctcg tttaacctat ggggaactgg atcaaaaggc tagggcgatc | 180 |

-continued

| | |
|---|---|
| gccgcttatc tacaatcctt agaagccgag ggcgaaaggg gtttactgct ctatccccca | 240 |
| ggactagatt ttatttcagc ttttttttggt tgtttatatg cgggagtcgt tgccattccc | 300 |
| gcctatccac cccgacggaa tcaaaacctt ttgcgtttac aggcgattat tgccgattct | 360 |
| caagcccgat ttaccttcac caatgccgct ctatttccca gtttaaaaaa ccaatgggct | 420 |
| aaagaccctg aattaggagc aatggaatgg attgttaccg atgaaattga ccatcacctc | 480 |
| agggaggatt ggctagaacc aaccctcgaa aaaacagtc tcgcttttct acaatacacc | 540 |
| tctggttcaa cgggaactcc aaagggagta atggtcagtc accataattt gttgattaat | 600 |
| tcagccgatt tagatcgtgg ttggggccat gatcaagata gcgtaatggt cacttggcta | 660 |
| ccgaccttcc atgatatggg tctgatttat ggggttattc agcctttgta caaaggattt | 720 |
| cttttgttaca tgatgtcccc tgccagcttt atggaacgac cgttacgttg gttacaggcc | 780 |
| cttctctgata aaaagcaac ccatagtgcg gccccaact ttgcctacga tctttgtgtg | 840 |
| cggaaaattc cccctgaaaa acgggctacg ttagacttaa gccattggtg catggcctta | 900 |
| aatgggccg aacccgtcag agcggaggta cttaaaaagt ttgcggaggc ttttcaagtt | 960 |
| tctggtttca aagccacagc cctttgtcct ggctacggtt tagcagaagc caccctgaaa | 1020 |
| gttacggcgg ttagttatga cagtccccct tactttatc ccgttcaggc taatgcttta | 1080 |
| gaaaaaaata agattgtggg agccactgaa accgatacca atgtgcagac cctcgtgggc | 1140 |
| tgcggctgga caacgattga tactcaaatc gtcattgtca atcctgaaac cctgaaacct | 1200 |
| tgctcccctg aaattgtcgg cgaaatttgg gtatcaggtt caacaatcgc ccaaggctat | 1260 |
| tgggaaaaac ctcaagagac tcaggaaacc tttcaagctt atttggcaga tacaggagcc | 1320 |
| gggccttttc tgcgaacagg agacttgggc ttcattaaag atggtgaatt gtttatcaca | 1380 |
| ggtcggctca aggaaattat tctgattcga ggacgcaata attatcccca ggatattgaa | 1440 |
| ttaaccgtcc aaaatagtca tcccgctctg cgtcccagtt gtggggctgc ttttaccgtt | 1500 |
| gaaaataagg gcgaagaaaa gctcgtggtc gttcaggaag tggagcgcac ctggctccgt | 1560 |
| aaggtagata tagatgaggt aaaaagagcc attcgtaaag ctgttgtcca ggaatatgat | 1620 |
| ttacaggttt atgcgatcgc gctgatcagg actggcagtt taccaaaaac ctctagcggt | 1680 |
| aaaattcagc gtcgtagctg tcgggccaaa tttttagagg gaagcctgga aattttgggc | 1740 |
| taagaaaatt tctcgatcgg cacttaatgt gttaaattcg tatgtcgatt gaaacttcga | 1800 |
| ccaattcttt ctctccccctt aagtccatgt ctctggattt gaaaattcct taaactttaa | 1860 |
| ctacatttct caagaaagca aattgaatct aatgtccaca gaaatcccaa acgacaaaaa | 1920 |
| acaaccgacc ctaacgaaaa ttcaaaactg ttagtggct tacatgacag agatgatgga | 1980 |
| agtggacgaa gatgagattg atctgagcgt tcccttttgat gaatatggtc tcgattcttc | 2040 |
| tatgcagtt gctttgatcg ctgatctaga ggattggtta cgacgagatt tacatcgcac | 2100 |
| cctgatctac gattatccaa ctctagaaaa gttggctaaa caggttagtg aaccctgaca | 2160 |
| ttttttataaa gttgtgcttt aaaaattttg aggaagttct aaaatgacaa attatggcaa | 2220 |
| atctatgtct cattactatg atctagtggt aggacataaa ggttataaca agattacgc | 2280 |
| cactgaagta gaattcattc acaatttagt tgagacttac acaactgaag ccaaatctat | 2340 |
| cctatacttg ggctgtggta cgggttatca tgccgctctt ttagcacaga aagggtattc | 2400 |
| tgtacatggt gttgatctca gtgctgaaat gttagagcag gctaaaactc gcattgaaga | 2460 |
| tgaaacaata gcttctaatc tgagttttc tcaaggaaat atttgtgaaa tccgtttaaa | 2520 |

```
tcgtcagttt aatgttgttc ttgctctatt tcatgtggtt aactatcaaa cgaccaatca   2580
aaatttactg gcaacgtttg caacggttaa aaaccattta aaagctgggg ggatttttat   2640
ttgtgatgtg tcctatgggt cttacgtact gggggaattt aagagtcggc ctacggcatc   2700
aatattgcgt ttagaggata attccaatgg taacgaagta acctatatta gtgaactaaa   2760
ttttttaacc catgaaaata tagtggaagt tactcacaat ttatgggtaa caaatcaaga   2820
aaatcaactt ctagagaatt cacgggaaac acatcttcag cgctatcttt tcaagcctga   2880
agttgaattg ttggctgatg cttgtgaact aactgttctt gatgcgatgc cctggcttga   2940
acaacgtcct ttgacaaaca ttccttgtcc ttcagtttgt tttgttattg ggcataaaac   3000
aacccattca gcttaaattc tgctaaaaaa aatccaactt accttattct ctgaaaccac   3060
acaagccatg aatacaattc aagatgccaa gaccgaaaat tactcaatct taaatcagtc   3120
aattccaaga cctctcaaac tgagtaatat cctattacga taagattttg cgttctcctt   3180
tgtttggaat gtcagcagag gagtctctat attggctaga gaaatgttta tgtcaagagc   3240
atcagggctt cgatgtacaa gttaagtatc atcaaaaaat gctgaagaat atgttacgtt   3300
tgaccgatag tttggattat ctatggccag ttaaccgtga aatgcggctc atgaaagctg   3360
gggggtcaat tgaacgggcg atcaccaata acattaaagc ttttcttcaa tttaaagaaa   3420
ctgtaaccgt attaaattag aaaaaccgca gtgaggaatt tgaatggaac ccatcgcaat   3480
tattggtctt gcttgccgct ttccaggggc tgacaatcca gaagctttct ggcaactcat   3540
gcgaaatggg gtggatgcga tcgccgatat tcctcctgaa cgttgggata ttgagcgttt   3600
ctacgatccc acacctgcca ctgccaagaa gatgtatagt cgccagggcg ttttctaaa   3660 aaatgtcgat caatttgacc ctcaattttt ccgaatttct cccctagaag ccacctatct   3720
agatcctcaa caaagactgc tactggaagt cacctgggaa gccttagaaa atgctgccat   3780
tgtgcctgaa accttagctg gtagccaatc aggggttttt attggtatca gtgatgtgga   3840
ttatcatcgt ttggcttatc aaagtcctac taacttgacc gccatatgtgg gtacaggcaa   3900 cagcaccagt attgcggcta accgtttatc atatctgttt gatttgcgtg gccccagttt   3960
ggccgtagat accgcttgct cttcttccct cgtcgccgtt cacttggcct gtcagagttt   4020
gcaaagtcaa gaatcgaacc tctgcttagt gggggggagtt aatctcattt tgtcgccaga   4080
gacaaccgtt gttttttccc aagcgagaat gatcgccccc gacagtcgtt gtaaaacctt   4140
tgacgcgagg gccgatggtt atgtgcgctc ggaaggctgt ggagtagtcg tacttaaacg   4200
tcttagggat gccattcagg acggcgatcg cattttagca gtgattgaag gttccgcggt   4260
gaatcaggat ggtttaagta atggactcac ggccctaat ggccctgctc aacaggcggt   4320
gattcgtcag gccctggcaa atgcccaggt aaaaccggcc cagattagct atgtcgaagc   4380
ccatggcacg gggacagaat tggggatcc gatcgaagtt aaatctctga agcggttttt   4440
gggtgaaaag cgatcgctcg atcaaacctg ttggctcggt tctgtgaaaa ccaacattgg   4500
tcatttagaa gcggcggcgg gaatggcggg tctgattaaa gtcgttctct gcctacaaca   4560
ccaagaaatt ccccctaatc tccactttca aacccttaat ccctatattt ccctagctga   4620
cacagctttt gcgattccca ctcaggctca accctggcgg accaaacccc ctaagtctgg   4680
tgaaaacggt gtcgaacgac gtttagcagg actcagttcc tttgggtttg ggggacaaa   4740 ttcccatgtg attctcagcg aagcccctgt caccgttaaa aacaatcaac aaaatgggca   4800
gaagttgata gaacgtccct ggcatttgct gactttatct gccaagaatg aagaagcctt   4860
aaaagcctta gtccattgtt atcaaaagta tttagctgat catcatgaaa ttcctctcgc   4920
```

```
tgatgtttgt tttacggcca atagtcggcg atcgcacttt aatcatcgtt taggagtagt    4980
ggctagagat cgcttagaaa tgttgcagaa gttagagaac tttagtaacc aagaaaggat    5040
gagagaaccg aagagtatta acaaaaagaa aaaacctaaa attgttttc tatttgccgg    5100 tcaaggttct caatatgtag gtatgggtcg tcaactgtac gaaacccaac ccatctttcg    5160
ccaaaccttg gatcgctgtg ctgaaatcct gcgaccccat ttagatcaac ccctcttaga    5220
aattctttat cctgctgacc cagaagccga aacagcgagt ttttacctag agcagactgc    5280
ctatacccaa cccactttat tcgcattcga gtatgcccta gcacagttat ggcgttcctg    5340
gggaatagaa ccggcggcag taattggtca cagtgtcggt gaatatgtgg cggccaccgt    5400
tgccggagcc ttaagtctag aagaaggatt aacgctaatt gccaaacggg caaaactgat    5460
gcagtctctc cccaagaatg gacaatgat cgccgttttt gccgcagaag agcgggttaa    5520
agctgttatt gagccttata ggactgatgt agcgatcgct gctgttaatg gaccagaaaa    5580
ttttgttatt tcaggaaaag cgccgattat tgctgagatt atcattcatt taacggcagc    5640
aggaatagaa gttcgtcctc tcaaagtttc ccatgctttt cactcgcacc tgttggagcc    5700
aattttagat tccttagaac aggaagctgc tgctatttcc taccaacccc tgcaaattcc    5760
cttagttgct aatttaacgg gggaagttct accagaagga gcaacgattg aggctcgtta    5820
ctggcgaaat catgcacgca accctgtaca attttatggg agtatccaaa cgctgatcga    5880
gcagaaattc agtctttttt tagaagttag ccctaaaccg actttatctc gattgggtca    5940
acaatgttgt ccagaaagat cgaccacttg gctattttcc ctcgcccctc tcaagaaga    6000 agaacaaagc ctactaaata gtttggcgat tctctatgat tcccaaggag ccgaaataaa    6060
ctgggaaggg tttaatcaaa attatcccca ccatttactg gctctaccga cctatccttt    6120
tcaacgtcaa cgctattggc ttgaaaccgg taaaccgact tctgaagaaa caaccatgac    6180
gaccaatgcc actaatgtcc aagctatctc cagccatcaa aaacaacagg agattctaat    6240
cacattgcaa accctagtgg gaaatttact gcaattgtcc cctgctgatg tcaatgttca    6300 tcacctttc ctggagatgg gggcagattc cattgtcatg gttgaggcgg tcagacggat    6360
tgagaatacc tataacgtta aaattgctat gcgtcagtta tttgaggagt tatctacttt    6420
agatgcttta gctacttatt tagctcaaaa tccggctact gattgccaaa ctgctcaaat    6480
taataccgag gtgttttctg cgcccattgc ctgctcaaat aaccgatcgc ccaatgtcgt    6540
gctgagttct aataccaacg gctttcaacg tcaaacagct tctccaggtt tttcggcgat    6600
cgcccccctt gcaggaatgg gaggagcagg ggaaatggga ggagttgaag tgcctcaagt    6660
ttctgtgcca caaaccagtg cggtaacagc ctcaggttca accgtttcta gttctgccct    6720
ggaaaacatt atgggtcaac agttacaact gatggccaaa cagttagaag tcttgcaaac    6780
ggccaatttt gccccgacga ctccccgaac cacagaaaat tccccatctt ccgtcagtca    6840
aaataggtca aacggactta cacaacagtt aattcccccc cagcaattag cggcgaacct    6900
agagccaata gccagtcgca cccgtcaaac cagcaatcaa gcttctgctc ctaaaccgac    6960
agtaacagcc actccctggg ggcgaaaaa accacccaca ggtggattca ctccccaaca    7020
acagcaacat ctagaggcat taattgctcg ctttacggaa cgtaccaaaa cctctaagca    7080
aattgtgcaa agcgatcgcc tgcgtttagc agatagtcga gcctcggtcg gattccgtat    7140
gtctattaaa gagatgcttt atcccattgt ggcccaacgt tctcaaggat caagaatttg    7200
ggatgtggac ggtaatgaat atattgatat gacgatgggg caaggggtaa cgctgtttgg    7260
```

```
gcatcaacca gacttcatta tgtcggccct acaaagccaa ctcactgaag gcattcatct   7320
caatccgcga tcgccaattg tgggagaagt ggccgcctta atttgtgaac taacaggagc   7380
cgaacgagct tgttttttgca actctggaac cgaagccgta atggccgcta ttcgtatcgc   7440
cagggcaaca acaggtcgga gtaaaattgc cctctttgaa ggctcctatc atggacatgc   7500
ggacggaacc cttttaggaa accaaattat tgataaccaa ctccactctt ttcccctagc   7560
tctaggcgtt ccccccagcc ttagttccga tgtggtggta ttggactatg gcagtgcgga   7620
agctctgaac tatttacaaa cccaggggca ggatttagcg gcggtcttag tagaaccaat   7680
tcaaagtggc aatcctctac tccaaccccca acaatttctc caaagtctgc gacaaattac   7740
cagtcaaatg gcattgccc tgattttttga tgaaatgatt acgggttttc gatcgcaccc   7800
agggggagcg caagctttat ttggagtaca ggcggatatt gccacctatg gcaaagtagt   7860
tgcgggagga atgcccattg gagttattgc aggtaaggcc cattatctgg acagcattga   7920
cgggggaatg tggcgttatg gcgataaatc ctatcctggg gtggacagaa ccttttttgg   7980
gggaaccttt aatcagcatc cgttagcaat ggtagcggct agggctgtcc tgacccattt   8040
aaaggagcag gggccaggtc tgcaacaaca attaactgaa cgcactgcgg ccttagccga   8100
tacactgaat cattattttc aagccgaaga agttcctatt aaaatcgaac agtttagttc   8160
tttcttccgg tttgccctct ctggcaattt ggatttactt ttctatcaca tggtagaaaa   8220
aggtatttat gtctgggaat ggcgtaaaca ttttctttca accgcccata cggaagccga   8280
tcttgcccaa tttgtccaag cggttaagga tagcatcaca gaattgcgtc agggaggttt   8340
tatccccgca aaaagccctt cctggccagt gccaacgcct caaattgatc ccccccctaac   8400 cccccttgat aagggattg atccccccct aaccccccctt gataagggga ttgatccccc   8460
cctaaccccc cttgataagg gggagatgt tgatgtcgcg cttgataagg gaggaaattc   8520
tcattctgtt agggacagta agttagggaa agggagcggg tctcaagacc aaaaaacgat   8580
acagtttagc ctctactact ttggtagcta tgaagcggaa tttaacccga ataaatataa   8640
cttactgttt gaaggagcta aatttggcga tcgcgctggt tttacggccc tttggattcc   8700
tgaacgtcat ttccacgctt ttggtggttt ttctcccaat ccttcggttt tggcggcggc   8760
tttagcacgg gaaccaaac agattcaact gcgatcaggc agtgtggttt taccgctaca   8820
taattccatc cgagtcgccg aagaatgggc agtggtggac aatctttccc agggccgcgt   8880
tggtattgct tttgcatcgg gttggcatcc ccaggatttt gtcttggctc cccagtcctt   8940
tggccaacat cgggaattga tgttccaaga aattgaaacc gtccagaaac tttggcgagg   9000
ggaagcgatc accgtgccag acggaaaggg tcaaagggta gaggttaaaa cctatcccca   9060
accgatgcag tcccagttac ccagctggat tactattgtc aataatcccg ataccatat   9120 cagagcaggg gcgatcggtg ctaatatcct taccaatctg atggggcaaa gcgtggaaga   9180
tttagcccgt aatattgcgc tatatcgtca atctttggca gagcatggtt atgatcccgc   9240
gtcgggaacg gtgacagttc tcctgcatac ttttgttggc aaggatttag aacaagttcg   9300
agaacaggct cgccaacccct ttgggcaata cctcacctcc tctgtcggac tcttgcagaa   9360
catggtcaag agccagggca tgaaagtgga ttttgaacaa ttaagagacg aagatcggga   9420
cttttcctcc gcttctgcct ataaacgcta tacagaaacc agtgctttaa ttggcacacc   9480
cgaatcctgt cgtcaaatta ttgatcattt gcagtccatc ggtgtggatg aagtggcttg   9540
ttttattgat tttgggggtag atgaacaaac agttttggcc aatttaccct atctccagtc   9600
cctaaaagac ttatatcaac ctcatctccc cccttatcaa gggggttag ggggggatca   9660
```

```
atccccttat caaggggggt tagggggggga tcaatcccct tatcaagggg ggttaggggg      9720
tgatcaatcc ccttatcaag ggggttaggg gggtgatcaa tcccttatc aaggggggtt      9780
agggggggat caatcccctt atcaaggaga gttagggggg gatcaatccc cttatcaagg     9840
ggggttaggg ggggatcaag tccctctcac cgaagcccaa cgacaactgt ggattttggc     9900
tcaattagga gacaacggct ctgtggccta aaccaatca gtgacattgc aattaagtgg      9960
cccattaaat cccgtcgcaa tgaatcaagc tattcaacaa atcagcgatc gccatgaagc    10020
gttacgaacc aaaattaatg cccagggaga tagtcaagaa atcctgcccc aggtcgaaat    10080
taactgccct atcttagact tcagtcttga ccaagcttcg gcccaacagc aagcagaaca    10140
atggttaaag gaagaaagtg aaaaacccctt tgatttgagc cagggttctc tcgtgcgttg   10200
gcatctactc aaattagaac cagaattaca tttgttagta ttaacggccc atcacattat    10260
cagtgacggt tggtcaatgg gggtaatcct tcgggaatta ggagagttat attcagccaa    10320
atgtcagggt gttacggcta atcttaaaac cccaaaacag tttcgagaat tgattgaatg    10380
gcaaagccag ccaagccaag gggaagaact gaaaaaacag caagcctatt ggttagcaac    10440
ccttgccgat ccccctgttt tgaatttacc cactgacaaa cctcgtccag ctttacccag    10500
ttaccaagct aatcgtcgaa gtctaacttt agatagccaa tttacagaaa aactaaagca    10560
atttagtcgt aaacagggct gtaccttgct gatgaccctg ttatcggttt ataacattct    10620
cgttcatcgt ttgacgggac aggatgatat tctggtgggt ctgccagcct ctggacgggg    10680
gcttttagat agtgaaggta tggtgggtta ttgcacccat ttttaccaa ttcgcagtca     10740
attagcaggt aatcccactt ttgctgaata tctcaaacaa atgcgggggg ttttgttgtc    10800
ggcttatgaa catcaggact atcccttttgc tcttttgctc aatcagttag atttaccgcg   10860
taataccagt cgctctcctt taattgatgt cagtttcaat ttagaaccag ttattaacct    10920
acccaaaatg aaaggattag agattagttt gttgcctcaa agtgtaagtt ttaaggatcg    10980
agatttgcat tggaatgtga cagaaatggg tggagaagct ctgattgatt gtgactacaa    11040
tacagactta tttaaagatg aaacgattca gcgttggtta ggccattttc aaaccttact    11100
tgaggcagtt attaatgatt cgcaacaaaa tctgcgggaa ttacccttat taagttctgc    11160
tgaacgacaa cagttattag tggattggaa tcaaaccaag accgactatc cccaagatca    11220
gtgtattcat caattatttg aagcgcaagt tgaacggact cccgatgcga ttgcggtggt    11280
atttgaaact caacaattaa cttacagtga attaaattgt cgagccaatc agttagcaca    11340
ttatttacaa aaattaggag ttgggccaga ggtcttagtc ggtatttttgg tcgaacgttc   11400
tttagaaatg attgtcggat tgttagggat tctcaaggct gggggagcct atgtacctct    11460
tgatcctgac tatccccctg aacgtcttca atttatgtta aagatagtc aatttttttct   11520
cctcttaacc caacagcatt tactggaatc ttttgctcag tcttcagaaa cggctactcc    11580
caagattatt tgtttggata cgactacca aattatttcc caggcaaaga atattaatcc     11640
cgaaaattca gtcacaacga gtaatcttgc ctatgtaatt tatacctctg gttcgacagg    11700
taaaccgaag ggcgtgatga ataatcatgt tgctattagt aataaattgt tatgggtaca    11760
agacacttat cctctaacca cagaagactg tattttacaa aaaactcccct ttagttttga   11820
tgtttcagtg tgggaattat tctggcccct actaaacgga gcgcgtttgg ttttttgccaa   11880
gccgaatggc cataaagatg ccagttactt agtcaatctg attcaagagc aacaagtaac    11940
aacgctacat tttgtgtctt ctatgctaca gctttttctg acagaaaaag acgtagaaaa    12000
```

```
atgtaatagt cttaaacgag tcatttgtag tggtgaagcc ctttcttag  agcttcaaga   12060
acgtttttt  gctcgtttag tctgtgaatt acacaatctt tatggaccga cagaagccgc   12120
tattcatgtc acattttggc aatgtcaatc agatagcaat ttgaaaacag tacccattgg   12180
tcggccgatc gctaatatcc aaatttacat tttagactct catcttcagc cagtacctat   12240
tggagtaatc ggagaattgc acattggtgg ggttggtttg gcgcgggtt  atttaaacag   12300
gcctgagtta acggcggaga aatttattgc aaatccgttt gcttcccttg atccccccct   12360
aaccccctt  gataagggg  gagatgagag ctataaaact tttaaaaagg ggagagca     12420
accatcaaga ttgtataaaa cgggagattt agctcgttat ttacccgatg caagattga    12480
gtatctaggg cgcattgata atcaggtaaa aattcgcggt ttccggattg aattggggga   12540
aattgaagcg gttttgctat cccatcccca ggtacgagaa gcggtcgttt tggtgagcga   12600
aagcgatcgc tctgaaaatc gggctttggt cgcttatatt gtccctaatg atcctgcttg   12660
tacgactcaa tcattacgag agtttgttaa acggcagctt cctgactata tgatcccagc   12720
ttattggctg atccttgaca atttaccgtt aaccagcaat ggcaaaattg atcgtcgggc   12780
tttaccgtta cctaatccag agttaaatcg ttcgatagac tatgtggctc ccaaaaatcc   12840
tacccaggag gcgatcgccg ctattttggg tcaagtttta aaactggaaa agtgggaat    12900
ttatgataac ttttttgaga tcggcggtaa ttctttgcaa gccactcaag ttatttcacg   12960
cttacgagaa agttttgccc tagagttgcc cttgcgtcgc ctgtttgaac aaccgactgt   13020
ggcggatttg gctttagccg taacggacat tcatgccact ttacaaaaat tacaaacccc   13080
tattgatgat ttatcaggcg atcgcgagga gattgaacta tgaaatctat tgaaaccttt   13140
ttgtcagatt tagccaatca agatattaaa ctctggatgg acggcgatcg cctgcgttgt   13200
aatgcacccc agggcctatt aaccccagag attcaaacag aactgaaaaa ccgtaaagca   13260
gaaatcattc actttctcaa tcaactgggt tcagaggagc aaattaatcc tagaacgatt   13320
cttcccattc ctcgtgatgg ccaattaccc ctctcctttg cccagtcgcg actctggttc   13380
ttgtatcaat tagaaggagc cacgggaacc tataacatga caggggcctt gagtttaagc   13440
gggcctcttc aggtcgaagc cctcaaacaa gccctaagaa ctatcattca acgccatgag   13500
ccattgcgta ccagtttcca atcggttgac ggggttccag tgcaggtgat taatccctat   13560
cctgtttggg aattagcgat ggttgatttg acaggaaagg agacagaagc agaaaaattg   13620
gcctatcagg aatcccaaac cccgtttgat ttgaccaata gtcctttgtt gagggtaacg   13680
ctcctcaaat tacagccaga aaagcatatt ttattaatta atatgcacca tattatttcc   13740
gatggctgtc aatcggtgt  tttttgttcgt gaattgtccc atctctatag ggcttttgtg   13800
gcgggtaaag aaccaacttt accgatttta ccaattcagt atgcggattt tgccgttgg    13860
cagcgagagt ggttacaggg taaggtttta gcggctcaat tggaatattg gaagcgacaa   13920
ttggcagatg ctcctcctct gctggaactg cccactgatc gccctcgtcc cgcaatccaa   13980
acctttcaag gcaagacaga aagatttgag ctagatagga aactgaccca agaattaaag   14040
gcattaagtc aacagtcggg ttgtacttta tttatgactt tgttggccgc ttttggggtg   14100
gttttatccc gttatagtgg ccagactgat atcgtcattg gttcggcgat cgccaaccgt   14160
aatcgccaag acattgaggg gttaattggc ttttttgtta acactttggc gttgaggtta   14220
gatttatcag aaaaacccag ctttgccgct ttttaaaaac aagtacagga agtcactcag   14280
gatgcctatg agcatcaaga cttgcccttt gaaatgttag tggaagaatt acaactagag   14340
cgcaaattag accgaaatcc tttggtacag gtgatgtttg ccctacaaaa tgcggccaat   14400
```

```
gaaacctgga atttacctgg gttgaccatt gaagaaatgt cttgggaact tgaacctgcc   14460
cgttttgacc tagaggttca tttatcagaa gttaacgccg gcatagctgg attctgttgc   14520
tacaccattg atctatttga tgatgcaacg atcgcccgtc tattggaaca ttttcagaat   14580
cttctcaggg caattattgt taatcctcaa gaatcggtaa gtttattacc cttgttgtca   14640
gaacaggaag aaaagcaact tttagttgat tggaatcaaa cccaagccga ttatccccaa   14700
gataagcttg tccatcagtt atttgaagtt caagcagcca gtcagccaga agcgatcgct   14760
ctaatctttg aaaatcaggt tttgacctat ggagaattaa accatcgcgc caatcaatta   14820
gctcactatc ttcagtcgtt aggagtcacc aaagaacaaa tcgtcggggt ttatctggaa   14880
cgttcccttg aaatggcgat cggatttta ggtattctca aagcaggagc cgcctatctc   14940
cccattgatc ctgaatatcc ctcagtacgc acccaattta ttctcgaaga tacccaactt   15000
tcgcttctct taactcaggc agaactggca gaaaaactgc cccagactca aaacaaaatt   15060
atctgtctag atcgggactg gccagaaatt acctcccaac cccagacaaa cctagaccta   15120
aagatagaac ctaataaccct agcctattgc atctatactt ctggttccac aggacaaccc   15180
aaaggagtac tgatttccca tcaagcccta ctcaacttaa ttttctggca tcaacaagcg   15240
tttgagattg gccccttaca taaagcgacc caagtggcag gcattgcttt cgatgcaacg   15300
gtttgggaat tgtggcccta tctgaccaca ggagcctgta ttaatctggt tccccaaaat   15360
attctgctct caccgacgga tttacgggat tggttgctta accgagaaat taccatgagt   15420
tttgtgccaa ctcctttagc tgaaaaatta ttatccttgg attggcctaa ccattcttgt   15480
ctaaaaaccc tgttactggg aggtgacaaa cttcatttt atcctgctgc gtcccttccc   15540
tttcaggtca ttaacaacta tggcccaacg gaaaatacag tggttgcgac ctctggactg   15600
gtcaaatcat cttcatctca tcactttgga actccgacta ttggtcgtcc cattgccaac   15660
gtccaaatct atttattaga ccaaaaccta caacctgtcc ccattggtgt accaggagaa   15720
ttacatttag gtgggggcggg tttagcgcag ggctatctca atcgtcctga gttaacggct   15780
gaaaaattta ttgccaatcc ctttgatccc cccctaaccc cccttgataa ggggggagaa   15840
gaaccctcaa aactctataa aacgggagac ttagcccgtt atttacccga tggcaatgta   15900 gaattttgg gacgtattga caatcaggta aaaattcggg gttttcgcat cgaaactggg   15960
gaaatcgaag ccgttttaag tcaatatttc ctattagctg aaagtgtagt cgttgccaag   16020
gaagataata ctgggggataa acgcctcgtg gcttatttgg ttcccgcctt gcaaaatgag   16080
gccctaccag agcaattagc ccaatggcaa agtgaataca tcagtgattg gcaaagtctc   16140
tatgaaagaa cctatagtca agggcaagac agcctagctg atctcacttt taatatcacg   16200
ggttggaata gcagttatac tcgtcaaccc cttcctgctt cagaaatgcg agagtgggtc   16260
gaaaacactg ttagtcgcat cttggctttc caaccagaac gcggtttaga aattggttgt   16320
ggtacaggtt tgttactctc cagggtagca aagcattgtc ttgaatattg gcaacggat   16380 tattcccaag gggcgatcca gtatgttgaa cgggtttgca atgccgttga aggtttagaa   16440
caggttaaat tacgctgtca aatggcagat aatttgaag gtattgccct acatcaattt   16500
gataccgtcg tcttaaattc gattattcag tattttccca gtgtggatta tctgttacag   16560
gtgcttgaag gggcgatcaa cgtcattggc gagcgaggtc agattttgt cggggatgtg   16620 cggagtttac ccctattaga gccatatcat gcggctgtgc aattagccca agcttctgac   16680
tcgaaaactg ttgaacaatg gcaacaacag gtgcgtcaaa gtgtagcagg tgaagaagaa   16740
```

```
ctggtcattg atcccacatt gttcctggct ttaaaacaac attttccgca aattagctgg    16800
gtagaaattc aaccgaaacg gggtgtggct cacaatgagt taactcaatt tcgctatgat    16860
gtcactctcc atttagagac tatcaataat caagcattat tgagcggcaa tccaacggta    16920
attacctggt taaattggca acttgaccaa ctgtctttaa cacaaattaa agataaatta    16980
ttaacagaca aacctgaatt gtggggaatt cgtggtattc ctaatcagcg agttgaagag    17040
gctctaaaaa tttgggaatg ggtggaaaat gcccctgatg ttgaaacggt tgaacaactc    17100
aaaaaacttc tcaaacaaca agtagatact ggtattaatc ctgaacaggt ttggcaatta    17160
gctgagtctc tcggttacac cgctcacctt agttggtggg aaagtagtca agacggttcc    17220
tttgatgtca tttttcagcg gaattcagaa gcggaggact caaaaaaatt aacccttttca   17280
aaacttgctt tctgggatga aaaacccttt aaaataaagc cctggagtga ctatactaac    17340
aaccctctgc gcggtaagtt agtccaaaaa ttaattccta agtacgaga atttctgcaa     17400
gaaaaactac ccagttatat ggttccccag gcgtttgtgc tgcttgattc ccttcctttg    17460
accccccaatg gtaaggtgga tcgtaaggcg ttaccttctc ctgatgcggc gactcgtgat   17520
ttagcgaaca gttttgtctt accccgcaat ccgattgaag ctcaactgac tcaaatttgg    17580
agtgaagttt gggactgga acgcattggc gttaaggaca acttttttga attgggagga     17640
cattctcttt tggctaccca ggttttatca agaattaatt cagcctttgg acttgatctt    17700
tctgtgcaaa ttatgtttga atcaccaacg atcgcgggca ttgcgggtta tattcaagcg    17760
gtagattggg tcgcccagga tcaagccgat agctcgttaa atcatgaaaa tactgaggta    17820
gtggagttct aagttatgac gaaaaagatt gttgaatttg tctgttatct acgggattta    17880
ggcattactt tagaagctga tgaaaaccgc ttacgctgtc aggctcccga aggaattttg    17940
accccagcac tccgtcaaga aattggcgat cacaaactgg aattattaca atttttacaa    18000
tgggtcaaac agtctaaaag taccgctcat ttgcctatta aacctgtcgc tagagacggt    18060
catttacccc tgtcttttgc tcaacaacgt ttatggtttt tacattatct ttcccctgat    18120
agtcgttcct acaataccct ggaaatattg caaattgatg ggaatctcaa tctgactgtg    18180
ctagagcaga gtttggggga attaattaac cgccatgaaa ttttagaac aacattcccc     18240
actgtttcag gggaaccgat tcagaaaatt gcacttccta gtcgttttca gttaaaagtt    18300
gataattatc aagatttaga cgaaaatgaa caatcagcta aaattcaaca agtagcagaa    18360
ttggaagcag acaagctttt tgatttaacg gtggggccac tgattcagtt taagctattg    18420
caattgagtc cccagaagtc ggtgctgctg ttgaaaatgc accatattat ctatgatggc    18480
tggtcttttg ggattctgat tcgggaatta tcggctctat acgaagcatt tttaaagaac    18540
ttagccaatc ctctccctgc gttgtctatt cagtatgcag attttgcggt ttggcaacgt    18600
caatatctct caggtgaggt cttagataaa caactcaatt attggcaaga acagttagca    18660
acagtctctc ctgttcttac tttaccaacg gatagacccc gtccggcgat acaaactttt    18720
cagggaggag ttgagcgttt tcaactggat caaaatgtca ctcaaggtct taaaaagtta    18780
ggtcaagatc aggttgcaac cctgtttatg acgttgttgg ccggtttcgg cgttttgcta    18840
tctcgttata gtggtcaatc tgatctgatg gtgggttctc cgatcgctaa tcgtaatcaa    18900
gcagcgatcg aacctttaat tggctttttt gctaacactt tggctttaag aattaattta    18960
tcagaaaatc ccagttttttt agaattatta gaacaagtta acagacaac tttagagggt    19020
tatgctcacc aagacctacc ctttgagatg ttagtagaaa agctacaact tgaccgtgat    19080
ttgagcagaa atcctttagt acaagtcatg tttgcgctac aaaatacctc tcaagatact    19140
```

```
tggaatctttt cgggtttaag tattgaaagt ttatctttat cagtggaaga aactgtcaga   19200
tttgatctag aagtaaactg ctggcaaaat tcagaaggtt tagcaataga ttggatttac   19260
agcagagatt tatttgacac tgcaacaatt gcaagaatgg gagaacattt tcaaaattta   19320
gttcaggcaa tcatactcaa tccaaaagct acagttaaag aacttccttt attaacaccc   19380
aaggaacgtg agcaattatt aatatcttgg aataatagca agactgatta tcctcaagag   19440
cagtgtattt atcaattatt tgaagcacaa gttgaacgga ctccaaaggc gatcgcagtg   19500
gtatttgagg agcaatcatt aacatacact gaattaaacc atcgcgctaa tcagttagcc   19560
cattatttac aaactttagg cgtgggagca gaagtcttag tcggtatttc cctagaacgt   19620
tctttagaga tgattatcgg cttattaggg attctcaagg taggtggtgc ttatcttcct   19680
cttgatccag actatcccac tgagcgtctt cagttgatgt tagaagacag tcaagttcct   19740
tttttgatta cccacagttc tttattagca aaattgcctc cctctcaagc aactctgatt   19800
tgtttagatc atatccaaga gcagatttct caatattctc cagataatct tcaatgtcag   19860
ttaactcctg ccaatttagc taacgttatt tatacctctg gctctacggg taagcctaaa   19920
ggggtgatgg ttgaacataa aggtttagtt aacttagctc ttgctcaaat tcaatctttt   19980
gcagtcaacc ataacagtcg tgtgctgcaa tttgcttctt ttagttttga tgcttgtatt   20040
tcagaaattt tgatgacctt tggttctgga gcgacgcttt atcttgcaca aaaagatgct   20100
ttattgccag gtcagccatt aattgaacgg ttagtaaaga atggaattac tcatgtgact   20160
ttgccgcctt cagctttagt ggttttaccc caggaaccgt tacgcaactt agaaaccttta  20220 attgtggcgg gtgaggcttg ttctcttgat ttagtgaaac aatggtcaat cgatagaaac   20280
tttttcaatg cctatgggcc aacggaagcg agtgtttgtg ccactattgg acaatgttat   20340
caagatgatt taaaggtgac gattggtaag gcgatcgcca atgtccaaat ttatattta   20400 gatgcctttt tacagccggt gccggtggga gtgtcaggag agttatacat tggtggagtt   20460
ggggtggcaa ggggctattt aaatcgtcct gaattaaccc aagaaaaatt tattgctaat   20520
ccttttagta acgacccaga ttctcggctc tataaaactg gcgacttagc gcgttattta   20580
cccgatggta atattgaata tttaggacgc attgacaatc aggtaaaaat tcgcggtttt   20640
cgcattgagt taggagaaat tgaagcggtt ctgagtcaat gtcccgatgt gcaaaatacg   20700
gcggtgattg tccgcgaaga tactcctggc gataagcgct tagttgccta tgtggttctt   20760
acttctgact cccagataac tactagcgaa ctgcgtcaat ttttggcgaa tcaattaccc   20820
gcctatcttg ttcctaatac ctttgttatt ttagatgatt tgccccctaac ccccagtggc   20880 aaatgcgatc gccgttcctt acctataccc gaaacacaag cgttatcaaa tgactatatt   20940
gcccctaaat ctcccactga agaaattctg gctcaaatat gggggcaagt tctcaagata   21000
gaaagagtca gcagagaaga taatttcttt gaattggggg ggcattccct tttagctacc   21060
caggtaatgt cccgtctgcg tgaaactttt caagtcgaat taccctttgcg tagtctcttt   21120 accgctccca ctattgctga attggcccta acaattgagc aatctcagca aaccattgct   21180 gctccccccca tcctaaccag aaacgacagt gctaacctcc cgttatcttt tgctcaacaa   21240
cgtttatggt ttctggatca attagaacct aacagcgcct tttatcatgt aggggggagcc   21300 gtaagactag aaggaacatt aaatattact gccttagagc aaagcttaaa agaaattatt   21360
aatcgtcatg aagctttacg cacaaatttt ataacgattg atggtcaagc cactcaaatt   21420
attcacccta ctattaattg gcgattgtct gttgttgatt gtcaaaattt aaccgacact   21480
```

```
caatctctgg aaattgcgga agctgaaaag ccctttaatc ttgctcaaga ttgcttattt    21540
cgtgctactt tattcgtgcg atcaccgcta gaatatcatc tactcgtgac catgcaccat    21600
attgttagcg atggctggtc aattggagta tttttcaag aactaactca tctttacgct     21660
gtctataatc agggtttacc ctcatcttta acgcctatta aaatacaata tgctgatttt    21720
gcggtctggc aacggaattg gttacaaggt gaaattttaa gtaatcaatt gaattattgg    21780
cgcgaacaat tagcaaatgc tcctgctttt ttacctttac cgacagatag acctaggccc    21840
gcaatccaaa cttttattgg ttctcatcaa gaatttaaac tttctcagcc attaagccaa    21900
aaattgaatc aactaagtca gaagcatgga gtgactttat ttatgactct cctggctgct    21960
tttgctacct tactttaccg ttatacagga caagcagata ttttagttgg ttctcctatt    22020
gctaaccgta atcgtaagga aattgaggga ttaatcggct tttttgttaa tacattagtt    22080
ctgagattga gtttagataa tgatttaagt tttcaaaatt tgctaaacca tgttagagag    22140
gtttctttag cagcctacgc ccatcaagat ttaccttttg aaatgttagt agaagcacta    22200
caccctcaac gagatctcag tcatacccct ttatttcagg taatgtttgt tttgcaaaat    22260
acaccagtgg ctgatctaga acttaaaaat gtaaaggttt gtcctctacc gatggaaaat    22320
aagactgcta aatttgattt aaccttatca atggagaatc tagaggaagg attgattggg    22380
gtttgggaat ataacaccga tctatttaat ggctcaacca ttgagcgaat gagtggacat    22440
tttgtcactt tgttagaaga tattgttgcc gctccaacga agtcagtttt acggttgtct    22500
ttgctgacgc aagaggaaaa actgcaatta ttgattaaaa atcagggtgt tcaagttgat    22560
tattctcaag agcagtgcat ccatcaatta tttgaagcgc aagttgaacg gactcccgat    22620
gcgattgcgg tggtatttga ggagcaatca ttaacctatg ctgaattaaa tcatcaagct    22680
aatcagttag tccattactt acaaacttta ggaattgggc cagaggtctt agtcgctatt    22740
tcagtagaac gttctttaga aatgattatc ggcttattag ccattctcaa ggcgtgtggt    22800
gcttatctcc ctcttgctcc tgactatccc actgagcgtc ttcagttcat gttagaagat    22860
agtcaagctt ctttttgat tacccacagt tctttattag aaaaattgcc ttcttctcaa     22920
gcgactctaa tttgtttaga tcacatccaa gagcagattt ctcaatattc tcccgataat    22980
cttcaaagtg agttaactcc ttccaatttg gctaacgtta tttacacctc tggctctacg    23040
ggtaagccta aaggggtgat ggttgaacat cggggcttag ttaacttagc gagttctcaa    23100
attcaatctt ttgcagtcaa aaataacagt cgtgtactgc aatttgcttc ctttagtttt    23160
gatgcttgta tttcagaaat tttgatgacc tttggttctg gagcgactct ttatcttgct    23220
caaaaaaatg atttattgcc aggtcagcca ttaatggaaa ggttagaaaa gaataaaatt    23280
acccatgtta ctttaccccc ttcagcttta gctgttttac caaaaaaacc gttacccaac    23340
ttacaaactt taattgtggc gggtgaggct tgtcctctgg atttagtcaa acaatggtca    23400
gtcggtagaa acttttcaa tgcctatggc ccgacagaaa cgagtgtttg tgccacgatt     23460
ggacaatgtt atcaagatga tttaaaggtc acgattggta aggcgatcgc taatgtccaa    23520
atttatattt tggatgcctt tttacaacca gtacccatcg gagtaccagg ggaattatac    23580
attggtggag tcggagttgc gaggggttat ctaaatcgtc ctgaattaac ggcggaaaga    23640
tttattccta atccttttga tccccccta accccccctta aaaggggggg agataagagc     23700
tatgaaactt ttaaaaaggg ggaagagcaa ccatcaaaac tctataaaac gggagattta    23760
gctcgttatt tacccgatgg caatattgaa tatttaggac gcattgacaa tcaggtaaaa    23820
attcgcggtt ttcgcattga gttaggagaa attgaagcgg ttctgagtca atgtcccgat    23880
```

```
gtgcaaaata cggcggtgat tgtccgtgaa gatactcctg gcgataaacg tttagttgcc    23940
tatgtggttc ttacttctga ctcccagata actactagcg aactgcgtca attcttggct    24000
aatcaattac ctgcctatct cgttcccaat acctttgtta ttttagatga tttgccccta    24060
accccaatg gtaaatgcga tcgccgttcc ttaccgcttc ctgatgatca gaccagaaaa     24120
aatattccta aaattggccc gcgtaattta gtggaattac aattagctca atctggtca     24180
gagattttag gcattaataa tattggtatt caggaaaact tctttgaatt aggcggtcat    24240
tctttattag cagtcagtct gatcaatcgt attgaacaaa agttagataa acgtttacca    24300
ttaaccagtc ttttttcaaaa tggaaccata gcaagtctag ctcaattact agcgcaagaa   24360
acaactcagc cagcctcttc accgttgatt gctatccagt ctcaaggtga taaaactcca    24420
tttttttgctg ttcatcccat tggtggtaat gtgctatgtt atgccgattt agctcgtaat  24480
ttaggaacga aacagccgtt ttatggatta caatcattag ggctaagtga attagaaaaa   24540
actgtagcct ctattgaaga aatggcgatg atttatattg aagcaataca aactgttcaa    24600
gcctctggtc cctactattt aggaggttgg tcaatgggag gagtgatagc ttttgaaatc    24660
gcccaacaat tattgaccca aggtcaagaa gttgctttac tggctttaat agatagttat    24720
tctcccagtt tacttaattc agttaatagg gagaaaaatt ctgctaattc cctgacagaa    24780
gaatttaatg aagatatcaa tattgcctat tctttcatca gagacttagc aagtatattt    24840
aatcaagaaa tctctttctc tgggagtgaa cttgctcatt ttacatcaga cgaattacta    24900
gacaagttta ttacttggag tcaagagacg aatcttttgc cgtcagattt tgggaagcag    24960
caggttaaaa cctggtttaa agttttccag attaatcacc aagctttgag cagctattct    25020
cccaagacgt atctgggtag aagtgttttc ttaggagcgg aagacagttc tattaaaaat    25080
cctggttggc atcaagtaat caatgacttg caatctcaat ggattagcgg cgatcactac    25140
ggtttaatta aaaatccagt cctcgctgaa aaactcaata gctacctagc ctaaaactttt  25200
caaaaagcct gattattgtt taaaatgaat gatcgttcac cggtcagagg acaagtatga    25260
caacccaaac agcttctagt gccaatgccc ttgcttcctt taaccaattt ttaagggatg   25320
taaaggcgat cgcccaaccc tattggtatc ccactgtatc aaataaaaga agcttttctg    25380
aggttattcg ttcctgggga atgctatcac tgcttatctt tttgattgtg ggattagtcg    25440
ccgtcacggc tttttaatagt tttgttaatc gtcgtttaat tgatgtcatt attcaagaaa   25500
aagatgcgtc tcaatttgcc agtacattaa ctgtctatgc gatcggatta atctgtgtaa    25560
cgctgctggc agggttcact aaagatattc gcaaaaaaat tgccctagat tggtatcaat    25620
ggttaaacac ccagattgta gagaaatatt ttagtaatcg tgcctattat aaaattaact    25680
ttcaatctga cattgataac cccgatcaac gtctagccca ggaaattgaa ccgatcgcca    25740
caaacgccat tagtttctcg gccactttt tggaaaaaag tttggaaatg ctaactttt     25800
tagtggtagt ttggtcaatt tctcgacaga ttgctattcc gctaatgttt tacacgatta    25860
tcggtaattt tattgccgcc tatctaaatc aagaattaag caagatcaat caggcacaac    25920
tgcaatcaaa agcagattat aactatgcct taacccatgt tcggactcat gcggaatcta   25980
ttgctttttt tcggggagaa aaagaggaac aaaaatattat tcagcgacgt tttcaggaag  26040
ttatcaatga tacgaaaaat aaaattaact gggaaaaagg gaatgaaatt tttagtcggg   26100
gctatcgttc cgtcattcag ttttttcctt tttagtcct tggcccttg tatattaaag    26160
gagaaattga ttatggacaa gttgagcaag cttcattagc tagttttatg tttgcatcgg   26220
```

-continued

```
ccctgggaga attaattaca gaatttggta cttcaggacg tttttctagt tatgtagaac   26280
gtttaaatga attttctaat gccttagaaa ctgtgactaa acaagccgag aatgtcagca   26340
caattacaac catagaagaa aatcattttg cctttgaaca cgtcaccta gaaacccctg    26400
actatgaaaa ggtgattgtt gaggatttat ctcttactgt tcaaaaaggt gaaggattat   26460
tgattgtcgg gcccagtggt cgaggtaaaa gttctttatt aagggcgatc gccggtttat   26520
ggaatgctgg cactgggcgt ttagtgcgtc ctcccctaga agaaattctc tttttgcccc   26580
aacgtcccta cattattttg ggaaccttac gcgaacaatt gctgtatcct ctaaccaata   26640
gtgagatgag caataccgaa cttcaagcag tattacaaca agtcaatttg caaaatgtgc   26700
taaatcgggt ggatgacttt gactccgaaa aaccctggga aaacattctc tccctcggtg   26760
aacaacaacg cctagccttt gctcgattgt tagtgaattc tccgagtttt accattttag   26820
atgaggcgac cagtgcctta gatttaacaa atgaggggat tttatacgag caattacaaa   26880
ctcgcaagac aacctttatt agtgtgggtc atcgagaaag tttgtttaat taccatcaat   26940
gggttttaga actttctgct gactctagtt gggaactctt aagcgttcaa gattatcgcc   27000
ttaaaaaagc gggagaaatg tttactaatg cttcgagtaa caattccata acacccgata   27060
ttactatcga taatggatca gaaccagaaa tagtctattc tcttgaagga ttttcccatc   27120
aggaaatgaa actattaaca gacctatcac tctctagcat tcggagtaaa gccagtcgag   27180
ggaaggtgat tacagccaag gatggtttta cctaccttta tgacaaaaat cctcagatat   27240
taaagtggct cagaacttaa                                              27260
```